(12) United States Patent
Ho et al.

(10) Patent No.: US 9,005,649 B2
(45) Date of Patent: *Apr. 14, 2015

(54) METHODS FOR MAKING CONTROLLED DELIVERY DEVICES HAVING ZERO ORDER KINETICS

(75) Inventors: Paul S. Ho, Austin, TX (US); Salomon Stavchansky, Austin, TX (US); Phillip Bowman, San Antonio, TX (US); Zhiquan Luo, Chandler, AZ (US); Zhuojie Wu, Austin, TX (US); Ashish Rastogi, San Antonio, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 317 days.

This patent is subject to a terminal disclaimer.

(21) Appl. No.: 13/383,820

(22) PCT Filed: Jul. 14, 2010

(86) PCT No.: PCT/US2010/042030
§ 371 (c)(1),
(2), (4) Date: Mar. 20, 2012

(87) PCT Pub. No.: WO2011/008897
PCT Pub. Date: Jan. 20, 2011

(65) Prior Publication Data
US 2012/0177716 A1 Jul. 12, 2012

Related U.S. Application Data

(60) Provisional application No. 61/225,309, filed on Jul. 14, 2009, provisional application No. 61/225,352, filed on Jul. 14, 2009.

(51) Int. Cl.
*A61F 2/00* (2006.01)
*A61F 2/82* (2013.01)
(Continued)

(52) U.S. Cl.
CPC ... *A61F 2/82* (2013.01); *A61F 2/91* (2013.01); *A61F 2/915* (2013.01); *A61L 17/005* (2013.01);
(Continued)

(58) Field of Classification Search
None
See application file for complete search history.

(56) References Cited

U.S. PATENT DOCUMENTS 3,618,604 A 11/1971 Ness
3,993,073 A 11/1976 Zaffaroni
(Continued)

FOREIGN PATENT DOCUMENTS

| WO | 2008/018024 A2 | 2/2008 |
| WO | 2011008896 | 1/2011 |
| WO | 2011008897 | 1/2011 |

OTHER PUBLICATIONS

Ukil, A., et al., "Curcumin, the Major Component of Food Flavour Turmeric, Reduces Mucusal Injury in Trinitrobenzene Sulphonic Adic Induced Colitis," British Journal of Pharmacology, (2003), 139:209-218.
(Continued)

*Primary Examiner* — Brian Gulledge
(74) *Attorney, Agent, or Firm* — Parker Highlander PLLC

(57) ABSTRACT

A method of making an injectable or implantable active agent delivery device capable of delivering a diagnostic, therapeutic, and/or prophylactic agent to a desired targeted site having orifice(s) on the surface is disclosed herein providing unidirectional release of the agent at a controlled desirable rate. The agent may include, but is not limited to, drugs, proteins, peptides, biomarkers, bioanalytes, and/or genetic material. The technology of the invention is based on parallel processing to fabricate micro-holes on tubes employing photo-lithography and reactive ion etching techniques and also incorporates a simple molding method to form the micro-holes on flexible polymer tubes, including bio-degradable tubes. The parallel processing method of the instant invention is fast, economical and well suited for mass production. The developed device, due to its composite structure, has the ability to combine several release mechanisms, leading to zero-order release kinetics for most of the time.

19 Claims, 16 Drawing Sheets

(51) Int. Cl.
| | |
|---|---|
| *A61F 2/91* | (2013.01) |
| *A61F 2/915* | (2013.01) |
| *A61L 17/00* | (2006.01) |
| *A61L 27/54* | (2006.01) |
| *A61L 29/16* | (2006.01) |
| *A61L 31/16* | (2006.01) |
| *A61M 25/00* | (2006.01) |

(52) U.S. Cl.
CPC ............... *A61L 27/54* (2013.01); *A61L 29/16* (2013.01); *A61L 31/16* (2013.01); *A61F 2250/0002* (2013.01); *A61F 2250/0068* (2013.01); *A61L 2300/602* (2013.01); *A61M 2025/0057* (2013.01); *A61F 2220/005* (2013.01); *A61F 2230/0013* (2013.01); *A61F 2230/0054* (2013.01)

(56) References Cited

U.S. PATENT DOCUMENTS

| | | | |
|---|---|---|---|
| 4,014,335 | A | 3/1977 | Arnold |
| 5,622,498 | A | 4/1997 | Brizzolara et al. |
| 5,660,848 | A | 8/1997 | Moo-Young |
| 6,217,895 | B1 | 4/2001 | Guo et al. |
| 6,375,972 | B1 | 4/2002 | Guo et al. |
| 6,537,459 | B1* | 3/2003 | Dufresne et al. ............ 216/8 |
| 6,540,698 | B1 | 4/2003 | Ishii |
| 6,942,695 | B1 | 9/2005 | Chapoy et al. |
| 8,197,839 | B2 | 6/2012 | Martinrod et al. |
| 2002/0082680 | A1* | 6/2002 | Shanley et al. .......... 623/1.16 |
| 2002/0098278 | A1 | 7/2002 | Bates et al. |
| 2003/0004563 | A1* | 1/2003 | Jackson et al. ........... 623/1.15 |
| 2003/0199969 | A1* | 10/2003 | Steinke et al. ........... 623/1.16 |
| 2004/0039343 | A1 | 2/2004 | Eppstein et al. |
| 2005/0065593 | A1 | 3/2005 | Chu et al. |
| 2005/0196424 | A1 | 9/2005 | Chappa |
| 2008/0125848 | A1 | 5/2008 | Kusleika et al. |
| 2008/0243049 | A1 | 10/2008 | Hardy |
| 2008/0319375 | A1 | 12/2008 | Hardy |
| 2012/0130300 | A1 | 5/2012 | Stavchansky et al. |

OTHER PUBLICATIONS

Vijayalakshmi, P., et al., "Development of Extended Zero-Order Release Gliclazide Tablets by Central Composite Design," Drug Development and Industrial Pharmacy, (2008), 34:33-45.

Virmani, Renu, et al., "Mechanism of Late In-Stent Restenosis After Implantation of a Paclitaxel Derivate-Eluting Polymer Stent System in Humans," Circulation, (2002), 106:2649-2651.

Waksman, Ron, et al., "Optimal Dosing and Duration of Oral Everolimus to Inhibit In-Stent Neointimal Growth in Rabbit Iliac Arteries," Cardiovascular Revascularization Medicine, (2006), 7:179-184.

Wang, Xinkang, et al., "Enhanced Leucocyte Adhesion to Interleukin-1B Stimulated Vascular Smooth Muscle Cells is Mainly Through Intercellular Adhesion Molecule-1," Cardiovascular Research, (1994), 28:1808-1814.

Yasuda, Satoshi, et al., "Local Delivery of Low-Dose Docetaxel, a Novel Microtubule Polymerizing Agent, Reduces Neointimal Hyperplasia in a Balloon-Injured Rabbit Iliac Artery Model," Cardiovascular Research, (2002), 53:481-486.

International Preliminary Report on Patentability for PCT/US2010/042030, dated Jan. 26, 2012, 6 pages.

International Search Report for PCT/US2010/042030, dated Apr. 28, 2011, 5 pages.

International Search Report and Written Opinion for PCT/US2010/042029, dated Mar. 10, 2011, 9 pages.

Aziz, Shahid, et al., "Late Stent Thrombosis Associated with Coronary Aneurysm Formation after Sirolimus-Eluting Stent Implantation," J. Invasive Cardiol., (Apr. 2007), 19:E96-E98.

Baffour, Richard, et al., "Enhanced Angiogenesis and Growth of Collaterals by in Vivo Administration of Recombinant Basic Fibroblast Growth Factor in a Rabbit Model of Acute Lower Limb Ischemia: Dose-Response Effect of Basic Fibroblast Growth Factor," J. Vasc. Surg., (1992), 16:181-191.

Camenzind, Edoardo, et al., "Stent Thrombosis Late After Implantation of First-Generation Drug-Eluting Stents. A Cause for Concern," Circulation, Mar. 20, 2007, pp. 1440-1455.

Camenzind, Edoardo, "Treatment of In-Stent Restenosis—Back to the Future?" N. Engl. J. Med., Nov. 16, 2006, pp. 2149-2151.

Chevalier, Bernard, et al., "Randomised Comparison of Nobri, Biolimus A9-Eluting Coronary Sent with a Taxus, Paclitaxel-Eluting Coronary Stent in Patients with Stenosis in Native Coronary Arteries: the Nobri 1 Trial," EuroIntervention, (2007), 2:426-434.

Clarke, Stephen J., et al., "Clinical Pharmacokinetics of Docetaxel," Clinical Pharmacokine, Feb. 1999, 36 (2):99-114.

Costa, Ricardo A., et al., "Angiographic Results of the First Human Experience with the Biolimus A9 Drug-Eluting Stent for De Novo Coronary Lesions," Am. J. Cardiol., (2006), 98:443-446.

Docherty, John J., et al., "Resveratrol Inhibition of Herpes Simplex Virus Replication," Antiviral Research, (1999), 43:135-145.

Docherty, John J., et al., "Resveratrol Selectively Inhibits *Neisseria gonorrhoeae* and *Neisseria meningitidis*," Journal of Antimicrobial Chemotherapy, (2001), 47:239-246.

Dorai, Thambi, et al., "Role of Chemopreventive Agents in Cancer Therapy," Cancer Letters, Nov. 25, 2004, vol. 215, Issue 2, pp. 129-140.

Duan, Xueyan, et al., "Development of Monolithic Osmotic Pump Tablet System for Isosorbide-5-Mononitrate Delivery and Evaluation of it In Vitro and In Vivo," Drug Development and Industrial Pharmacy, (2009), 35:499-507.

El-Malah, Yasser, et al., "D-Optimal Mixture Design: Optimization of Ternary Matrix Blends for Controlled Zero-Order Drug Release from Oral Dosage Forms," Drug Development and Industrial Pharmacy, (2006), 32:1207-1218.

Elmali, N., et al., "Effects of Resveratrol in Inflammatory Arthritis," Inflammation, (Apr. 2007), vol. 30, Nos. 1-2, 6 pages.

Farb, Andrew, et al., "Oral Everolimus Inhibits in-Stent Neointimal Growth," Circulation, (2002), 106:2379-2384.

Geerts, A.M., et al., "Angiogenesis in Portal Hypertension: Involvement in Increased Splanchnic Blood Flow and Collaterals?" Acta Clinica Belgica, (2007), 62, 5 pages.

Golino, Paolo, et al., "Inhibition of Leucocyte and Platelet Adhesion Reduces Neointimal Hyperplasia after Arterial Injury," ThrombHaemost, (1997), 77:783-788.

Goto, T., et al., "Discovery of FK-506, a Novel Immunosuppressant Isolated from *Streptomyces tsukubaensis*," Transplantation Proceedings, Oct. 1987, vol. XIX, No. 5, pp. 4-8.

Gottschalk, Alexander R., et al., "Apoptosis in B Lymphocytes: The WEHI-231 Perspective," Immunology and Cell Biology, (1995), 73:8-16.

Green, M.R., et al., "Abrazane, a Novel Cremophor-Free, Albumin-Bound Particle Form of Paclitaxel for the Treatment of Advanced Non-Small-Cell Lung Cancer," Annals of Oncology, Jun. 1, 2006, 17:1263-1268.

Grube, Eberhard, et al., "Everolimus for Stent-Based Intracoronary Applications," Rev. Cardiovasc. Med., (2004), 5: S3-S8J.

Gupta, Kamlesh K., et al., "Dietary Antioxidant Curcumin Inhibits Microtubule Assembly through Tubulin Binding," FEBS Journal, (2006), 273:5320-5332.

Holmes, Jr., David R., "Incidence of Late Stent Thrombosis with Bare-Metal, Sirolimus, and Paclitaxel Stents," Rev. Cardiovasc. Med., (2007), 8:S11-S18.

Huang, Mou-Tuan, et al., "Inhibitory Effects of Dietary Curcumin on Forestomach, Duodenal, and Colon Carcinogenesis in Mice," Cancer Research, (1994), 54:5841-5847.

Jin, Xinghua, et al., "Optimization of Extended Zero-Order Release Gliclazide Tablets Using D-Optimal Mixture Design," Yakugaku Zassshi, (2008), 128:1475-1483.

Kasdallah-Grissa, Abir, et al., "Resveratrol, a Red Wine Polyphenol, Attenuates Ethanol-Induced Oxidative Stress in Rat Liver," Life Sciences, (2007), 80:1033-1039.

Kim, Hack-Lyoung, et al., "Stent-Related Cardiac Events After Non-Cardiac Surgery: Drug-Eluting Stent vs. Bare metal Stent," International Journal of Cardiology, (2008), 123:353-3543.

(56) References Cited

OTHER PUBLICATIONS

Kopp, Peter, Resveratrol, a Phytoestrogen Found in Red Wine. A Possible Explanation for the Conundrum of the French Paradox,? European Journal of Endocinology, (1998), 138:619-620.

Lagerqvist, Bo., et al., "Long-Term Outcomes with Drug-Eluting Stents Versus Bare-Metal Stents in Sweden," The New England Journal of Medicine, (2007), 356:1009-10019.

Li, Jian-Jun, et al., "Is Inflammation a Contributor for Coronary Stent Restenosis?" Medical Hypotheses, (2007), 68:945-951.

Liu, Quan, et al., "Zero-Order Delivery of a Highly Soluble, Low Dose Drug Alfuzosin Hydrochloride via Gastro-Retentive System," International Journal of Pharmaceutics, (2008), 348:27-34.

Margolis, James, et al., "Systemic Nanoparticle Paclitaxel (nab-Paclitaxel) for In-Stent Restenosis I (SNAPIST-I): A First-in-Human Safety and Dose-Finding Study," Clin. CardioL, (2007), 30:165-170.

Meredith, I., et al., "Nobori 1 Clinical Trial—Results at One Year," Heart, Lung and Circulation, (2007), 16:S149.

Mnjoyan, Zakar H., et al., "Profound Negative Regulatory Effects by Resveratrol on Vascular Smooth Muscle Cells: a Role of p53-p21 WAF1/CIP1 Pathway," Biochemical and Biophysical Research Communications, (2003), 311:546-552.

Moses, Jeffrey W., et al., "Sirolimus-Eluting Stents Versus Standard Stents in Patients with Stenosis in a Native Coronary Artery," The New England Journal of Medicine, Oct. 2, 2003, vol. 349, No. 14, pp. 1315-1323.

Ng, E.Y.K., et al., "Optimization of Nanoparticle Drug Microcarrier on the Pharmacokinetics of Drug Release: A Preliminary Study," J. Med. Syst., (2008), 32:85-92.

Olas, Beata, et al., "Resveratrol, a Phenolic Antioxidant with Effects on Blood Patelet Functions," Platelets, Aug. 2005, 5:251-260.

Pace-Asciak, Cecil R., et al., "The Red Wine Phenolics Trans-Resveratrol and Quercetin Block Human Platelet Aggregation and Eisosanoid Synthesis: Implications for Protection Against Coronary Heart Disease," Clinica Chimica Acta, (1995), 235:207-219.

Park, SJ., et al., "A Paclitaxel-Eluting Stent for the Prevention of Coronary Restenosis," New England Journal of Medicine, (2003), vol. 348, No. 16, pp. 1537-1545.

Patel, Jignesh, et al., "Everolimus: An Immunosuppressive Agent in Transplantation," Expert Opin. Pharmacother, (2006), 7(10):1347-1355.

Pfisterer, M.E., et al., "Die Basket-Late-Studie, Basel Stent Cost-Effectiveness Trial-Late Thrombotic Events Trial," Herz, (2006), 31:259, 1 page.

Poussier, Bertrand, et al., "Resveratrol Inhibits Vascular Smooth Muscle Cell Proliferation and Induces Apoptosis," Journal of Vascular Surgery, (Dec. 2005), vol. 42 No. 6, pp. 1190-1197.

Rahman, Irfan, et al., "Regulation of Inflammation and Redox Signaling by Dietary Polyphenols," BioChemical Pharmacology 72, (2006), pp. 1439-1452.

Sainani, Gurmukh, et al., "The Endothelial Leukocyte Adhesion Molecule. Role in Coronary Artery Disease," Acta Cardiol., (2005), 60(5):501-507.

Sankalia, Jolly M., et al., "Drug Release and Swelling Kinetics of Directly Compressed Glipizide Sustained-Release Matrices: Establishment of Level A IVIVC," Journal of Controlled Release, (2008), 129:49-58.

Seabra-Gomes, Ricardo, "Percutaneous Coronary Interventions with Drug Eluting Stents for Diabetic Patients," Heart, (2006), 92:410-419.

Silvestrini, Rosella, et al., "In Vitro Cytotoxic Activity of Taxol and Taxotere on Primary Cultures and Established Cell Lines of Human Ovarian Cancer," Stem Cells, (1993), 11:528-535.

Steinberg, Daniel H., et al., "Drug-Eluting Stent Thrombosis vs Bare Metal Stent Restenosis: Finding the Lesser of Two Evils," Am. Heart Hosp. J., (2007), 5:151-154.

\* cited by examiner

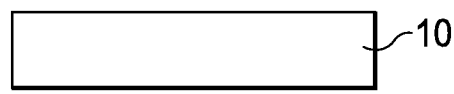
FIG. 12A
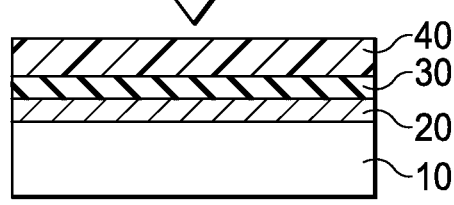
FIG. 12B
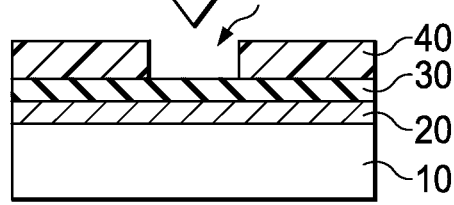
FIG. 12C
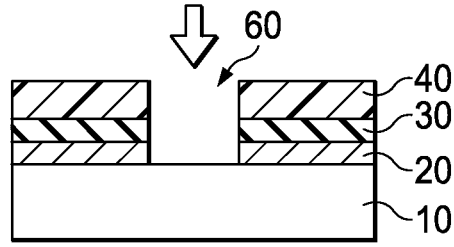
FIG. 12D
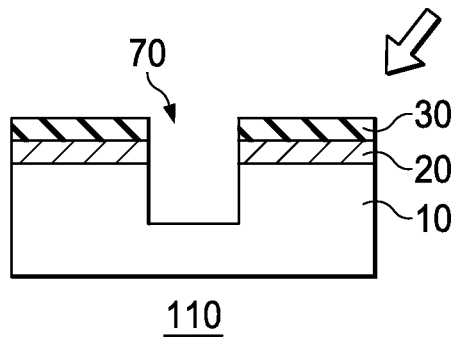
FIG. 12E
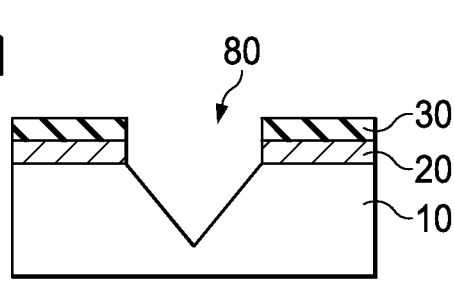
FIG. 12F

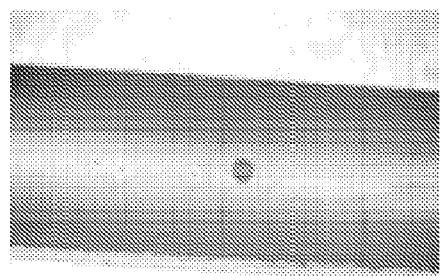
FIG. 13E
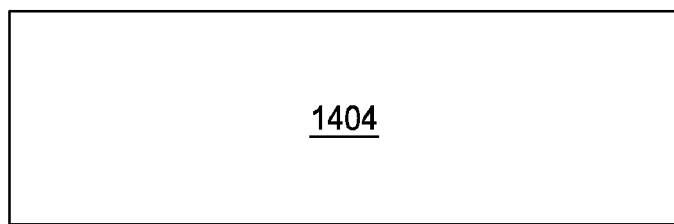
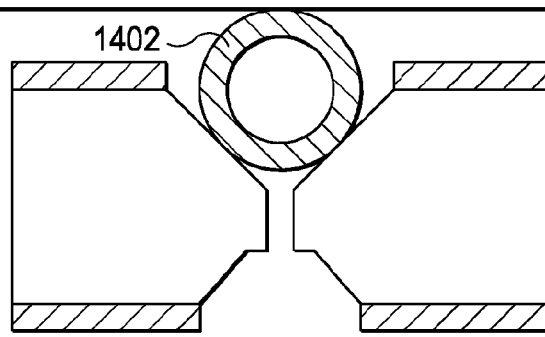
FIG. 14A
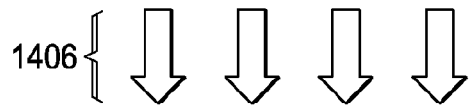
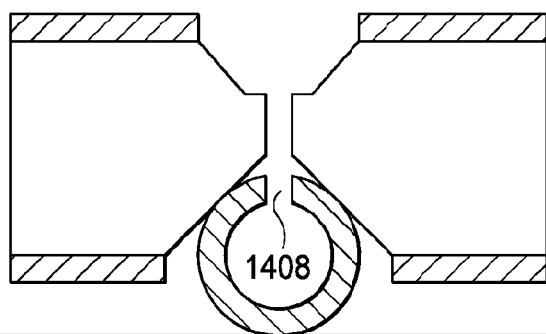
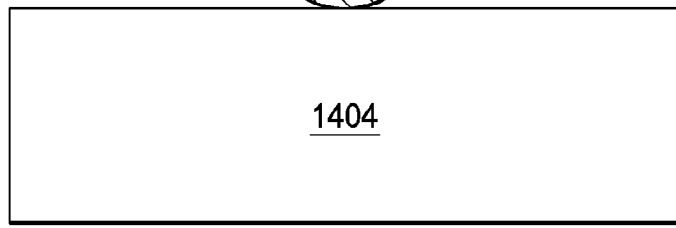
FIG. 14B

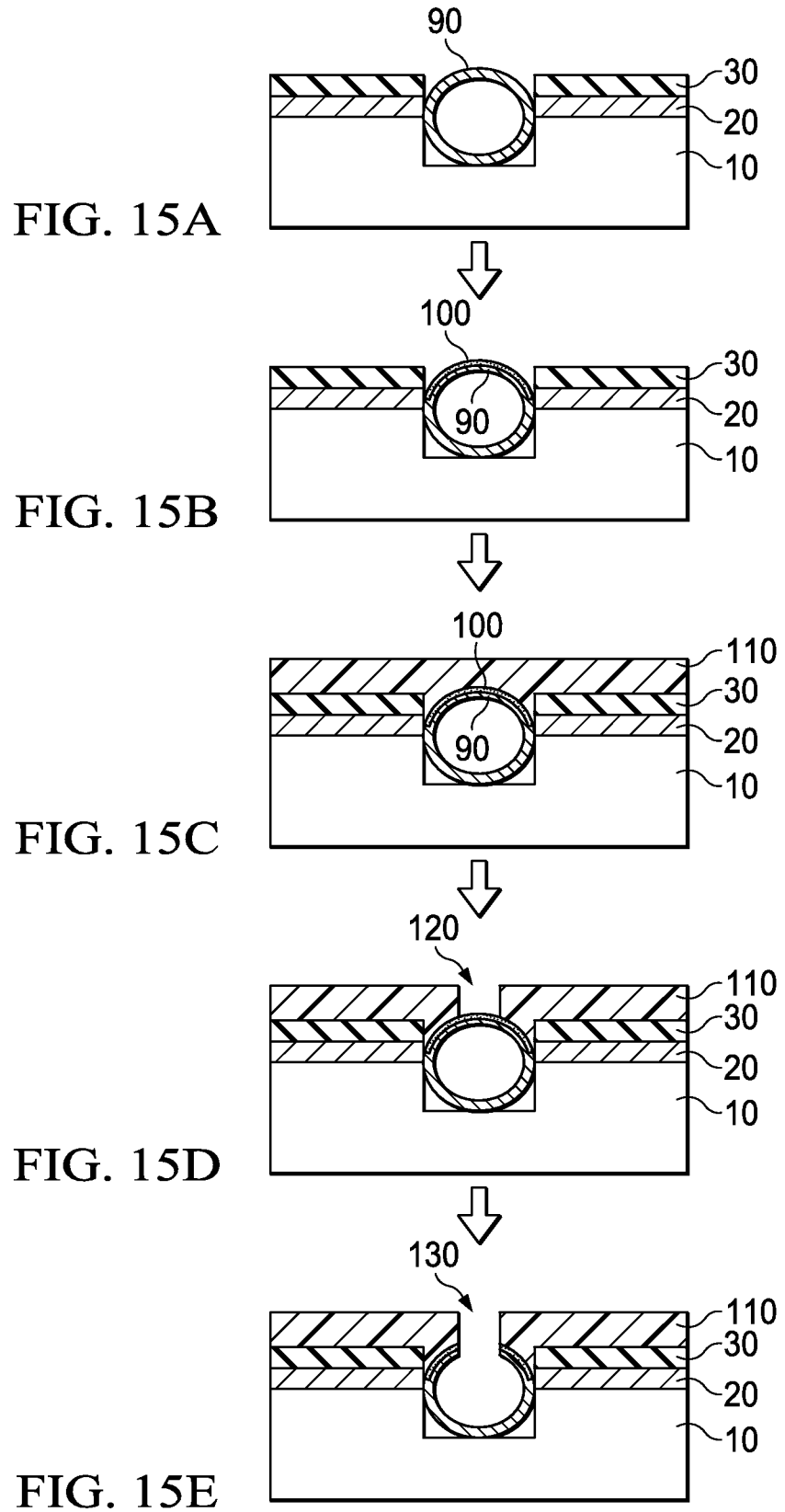

METHODS FOR MAKING CONTROLLED DELIVERY DEVICES HAVING ZERO ORDER KINETICS

CROSS-REFERENCE TO RELATED APPLICATIONS

This application is a National Stage of International Application No. PCT/US2010/042030, filed Jul. 14, 2010 which claims the benefit of U.S. Provisional Application Nos. 61/225,309 and 61/225,352, both filed Jul. 14, 2009. The contents of each of which are incorporated by reference in their entirety.

TECHNICAL FIELD OF THE INVENTION

This invention relates to methods for making a therapeutic agent delivery device that is capable of delivering a diagnostic, therapeutic, and/or prophylactic agent. Optionally, the delivery device may monitor bodily fluid analytes by incorporation of microelectronics. Additionally, the release of the agent from the device is unidirectional and at a controlled desirable rate. For example, the agent may include, but is not limited to, drugs, proteins, peptides, biomarkers, bioanalytes, and/or genetic material.

BACKGROUND ART

A number of implantable drug delivery devices have been suggested to be capable of delivering the drug to the body lumen. One universal advantage to implanted drug delivery devices is related to the local administration of a drug that inherently improves efficacy and decreases side effects, when compared to other routes of administration such as oral, rectal, topical, or systemic.

Nonetheless, a problem with the known implantable drug delivery devices is that the delivery rate cannot be controlled during all operational phases of the devices (i.e., drug delivery rates may change thereby resulting in, for example, first order delivery kinetics or second order delivery kinetics). Such problems result in a drug delivery device that administers drugs in an unpredictable pattern, thereby resulting in poor therapeutic benefit.

For example, a popular drug delivery device is a drug eluting stent. Stents are mesh-like steel or plastic tubes that are used to open up a clogged atherosclerotic coronary artery or a blood vessel undergoing stenosis. A drug may be attached onto, or impregnated into, the stent that is believed to prevent re-clogging or restenosis a blood vessel. However, the initial release of the drug may be very rapid releasing 20-40% of the total drug in a single day. Such high concentrations of the drug have been reported to result in cytotoxicity at the targeted site.

As a result of these problems, there is a need for a drug delivery device, which can be optimized to deliver any therapeutic, diagnostic, or prophylactic agent for any time period up to several years maintaining a controlled and desired rate.

SUMMARY OF THE INVENTION

This invention relates to methods of making a therapeutic agent delivery device that is capable of delivering a diagnostic, therapeutic, and/or prophylactic agent to a desired targeted site. Optionally, the delivery device may monitor bodily fluid analytes. Additionally, the release of the agent from the device is unidirectional and at a controlled and desirable rate. For example, the agent may include, but is not limited to, drugs, proteins, peptides, biomarkers, bioanalytes, and/or genetic material.

In one embodiment the present invention discloses a method for making a device for delivery of one or more active agents with zero-order kinetics comprising the steps of: providing a mold comprising a first surface and a second surface, wherein the first surface comprises one or more trenches, cavities or depressions, wherein each of the one or more trenches, cavities or depressions comprise one or more holes or perforations, placing a first substrate in the trenches, cavities or depressions, wherein the substrate may optionally be held in place in the trench by using an adhesive, and transferring a shape of the holes or the perforations in the one or more trenches, cavities or depressions to the first substrate by one or more microfabrication techniques to make the device for the delivery of the one or more active agents. The shape of the one or more holes or perforations as described in the instant invention is selected from the group consisting of a triangle, a polygon, an undecagon, a trapezium or trapezoid, a quadrilateral, an icosagon, a star polygon, an annulus, a circle, a crescent, an ellipse, an oval, an arbelos, a Reuleaux triangle, a semicircle, a sphere, an Archimedean spiral, an astroid, a deltoid, a super ellipse, and a tomahawk. The one or more microfabrication techniques listed hereinabove are selected from the group consisting of physical etching, chemical etching, reactive ion etching, physical vapor deposition, chemical vapor deposition, liftoff, electroplating, electroless plating, ion milling, laser ablation, plasma torch cutting, lithography, and combinations and modifications thereof.

The method of the present invention further comprises two optional steps: (i) pushing the substrate to the bottom of the trench by using a second substrate, wherein the second substrate is selected from the group consisting of silicon, glass, polymer, stainless steel, metals, alloys, ceramics, semiconductors, dielectrics, and combinations and modifications thereof and (ii) flipping the mold prior to the step of transferring the shape, wherein the flipping results in the second surface facing the one or more microfabrication or etching sources, wherein the etching sources are selected from the group consisting of ions, etching gases, plasma, laser beams, and combinations or modifications thereof. In one aspect the first substrate material is selected from the group consisting of a polymer, a rubber, a metal, a semiconductor, a dielectric, a mineral, a ceramic, and a glass. In another aspect the method further comprises the step of loading an active agent supply in the device by a method selected from the group consisting of capillary action, dipping, injecting, and pressure loading using positive or negative pressures. In another aspect the one or more active agents comprise a solid, a liquid dosage, a semi-solid, a powder, or a hydrogel. In yet another aspect the device may optionally be attached to a medical device or a microelectronic circuit, wherein the microelectronic circuit comprises at least one of a sensor, a transmitter, a receiver, a transceiver, a switch, a power supply or a light and the medical device is selected from the group consisting of a stent, an urinary catheter, an intravascular catheter, a dialysis shunt, a wound drain tube, a skin suture, a vascular graft, an implantable mesh, an intraocular device, an eye buckle, a heart valve, and combinations and modifications thereof.

In a specific aspects of the method described hereinabove the one or more holes or perforations are circular with ranges from 1 nanometer-1 centimeter, 100 nanometers-100 microns, 1 micron-50 microns, 10-30 microns, 15-25 microns or 20 microns, the first substrate is a polymer tube and the microfabrication technique is reactive ion etching using a plasma.

The method of the present invention may further comprise the optional step of polymer coating the device to prevent a release of the one or more active agents until the coating is removed, which then causes release of the one or more active agents at a substantially constant rate, wherein the polymer coating is selected from the group consisting of polysaccharides, proteins, poly(ethylene glycol), poly(methacrylates), poly(ethylene-co-vinyl acetate), poly(DL-lactide), poly(glycolide), copolymers of lactide and glycolide, polyanhydride copolymers, and combinations and modifications thereof. In other related aspects the one or more active agents are selected from the group consisting of drugs, proteins, vitamins, minerals, saccharides, lipids, nucleic acid, peptides, manure, plant nutrients, chemicals, perfumes, fragrances, flavoring agents, animal feed, effervescent gas releasing agents, and combinations and modifications thereof, wherein the drugs are selected from the group consisting of an analgesic agent, an antiinflammatory agent, an antihistaminic agent, an antiallergic agent, a central nervous system drug, an antipyretic agent, a respiratory agent, a steroid, a local anesthetic, a sympathomimetic agent, an antihypertensive agent, an antipsychotic agent, a calcium antagonist, a muscle relaxant, a vitamin, a cholinergic agonist, an antidepressant, an antispasmodic agent, a mydriatic agent, an anti-diabetic agent, an anorectic agent, an antiulcerative agent, an anti-tumor agent, or combinations modifications thereof, the proteins are selected from the group consisting of an immunoglobulin or fragments thereof, a hormone, an enzyme, a cytokine, a biomolecule, and combinations and modifications thereof.

The device of the present invention is adapted for implantation, ingestion or placement in or on a living organism, attachment to the medical device, placement in soil, water or food, attachment to an aquarium feeder, and combinations and modifications thereof. In one embodiment the method further includes steps for making the mold used hereinabove, comprising the steps of: (i) providing a substrate comprising a first surface and a second surface, (ii) forming one or more trenches on the first surface or on the second surface by one or more microfabrication techniques, and (iii) forming one or more holes or perforations on the one or more trenches by one or more microfabrication techniques. In one aspect the substrate comprises a material selected from the group consisting of semiconductors, metals, dielectrics, polymers, rubbers, minerals, and ceramics. In related aspects the first and the second surfaces can either be planar or non-planar surfaces.

In one aspect the one or more trenches are made by one or more microfabrication techniques selected from the group consisting of physical etching, chemical etching, reactive ion etching, physical vapor deposition, chemical vapor deposition, liftoff, electroplating, electroless plating, ion milling, laser ablation, plasma torch cutting, thin film deposition, lithography, mechanical drilling, sand blasting, and combinations and modifications thereof. In a specific aspect the substrate is a silicon wafer. In another aspect the one or more microfabrication techniques are selected from the group consisting of thin film deposition, photolithography, wet anisotropic etching, reactive ion-etching, and combinations and modifications thereof.

In another embodiment the instant invention provides for a method for making one or more trenches comprising the steps of: depositing at least one layer on the first surface of the substrate, wherein the layer serve as etching mask layer, wherein the deposition is done by physical vapor deposition, coating a photo-resist layer onto the etching mask layer, creating a trench structure on the photo-resist layer by using photolithography, aligning a desired trench direction and creating one or more alignment marks on the substrate, transferring the trench structure through the etching mask layer to the substrate or substrate layer by using one or more microfabrication techniques, and removing any residual substrate or substrate-layer materials from the formed trenches. In related aspects the etching mask layer is selected from the group consisting of silicon dioxide, silicon nitride, chromium, nickel, aluminum, $Al_2O_3$, and combinations and modifications thereof, the photo-resist layer is selected from the group consisting of Poly(methyl methacrylate) (PMMA), Poly(methyl glutarimide) (PMGI), Phenol formaldehyde resin, SU-8, and combinations and modifications thereof and the microfabrication techniques are selected from the group consisting of photolithography, wet anisotropic etching, physical etching, chemical etching, reactive ion etching, physical vapor deposition, chemical vapor deposition, liftoff, electroplating, electroless plating, ion milling, laser ablation, plasma torch cutting, thin film deposition, lithography, mechanical drilling, sand blasting, and combinations and modifications thereof.

The method described hereinabove further comprises the additional step of forming one or more holes or perforations on the one or more trenches comprising the steps of: depositing at least one etching mask layer on the second surface of the substrate or the substrate layer, defining a window pattern by photolithography on the second surface of the substrate or the substrate layer, aligning the window pattern to the trench on the first surface of the substrate or the substrate layer using the one or more alignment marks, transferring the window pattern onto the substrate or the substrate layer by a combination of reactive ion and wet anisotropic etching, defining the hole or perforation structure by lithography, and forming the hole or the perforation by reactive ion etching. In one aspect the method further comprises the step of hardening the mold structure. In one embodiment the present invention relates to a device for delivery of one or more active agents with zero-order kinetics made by the method described hereinabove.

Yet another embodiment of the instant invention relates to a method for making a device for delivery of one or more active agents with zero-order kinetics by a reactive ion etching technique comprising the steps of: (i) providing a silicon-wafer mold comprising a first surface and a second surface, wherein the first surface comprises one or more trenches, cavities or depressions, wherein each of the one or more trenches, cavities or depressions comprise one or more holes, perforations or patterns, (ii) placing a first substrate in the trenches, cavities or depressions, wherein the substrate may optionally be held in place in the trench by using an adhesive, and (iii) transferring a shape of the holes, the perforations or the patterns in the one or more trenches, cavities or depressions to the first substrate by using a reactive plasma to make the device for the delivery of the one or more active agents.

The method as described above further comprises the optional steps of pushing the first substrate to the bottom of the trenches, cavities or depressions by using a second substrate, wherein the second substrate is selected from the group consisting of silicon, glass, polymer, stainless steel, metals, alloys, ceramics, semiconductors, dielectrics, and combinations and modifications thereof and of flipping the mold prior to the step of transferring the shape, wherein the flipping results in the second surface facing the reactive plasma. In a specific aspect the first substrate is a planar or a non-planar substrate more specifically a cylindrical polymer tube of polyimide.

In one embodiment the silicon-wafer mold is made by a method comprising the steps of: providing the silicon-wafer substrate comprising a first surface and a second surface, forming one or more trenches on the first surface or on the second surface, and forming one or more holes, perforations or patterns on the one or more trenches. The step of making the one or more trenches further comprises the steps of: (i) depositing at least one etching mask layer on the silicon-wafer substrate by a physical vapor deposition, wherein the etching mask layer comprises a silicon nitride layer and a chromium layer, (ii) spin-coating a photo-resist layer onto the etching mask layer, (iii) creating a trench structure on the photo-resist layer by using a photolithographic technique, (iv) aligning a desired trench direction and creating of one or more alignment marks on the substrate, wherein the alignment marks are used to position the first substrate, (v) transferring the trench structure through the one or more etching mask layers to the silicon-wafer substrate by the reactive ion etching technique using a reactive plasma, and (vi) fabricating the trench structure by removal of any residual substrate or substrate-layer materials from the formed trenches by a wet anisotropic etching step.

The one or more one or more holes, perforations or patterns on the one or more trenches are made by: (i) defining a window pattern by a photolithographic technique aligned to the formed trenches on the surface of the silicon-wafer not containing the formed trench structures, (ii) transferring the window pattern onto the trench structure by a combination of reactive ion etching and wet anisotropic etching, and (iii) forming one or more holes, perforations or patterns on the one or more trenches by a combination of lithography and reactive ion etching. In related aspects the selection of the silicon-wafer substrate is dependent on the shape of the trench structure to be transferred and the depth and the width of the trench structure is dependent on a geometry of the photo-resist layer and a duration of the anisotropic etching step. In another aspect the method comprises an optional step of hardening the silicon-wafer mold by an application of a silicon-nitride layer to the surface. In one embodiment the present invention discloses a device for delivery of one or more active agents with zero-order kinetics made by the method described above.

Yet another embodiment of the instant invention discloses a method for making a device for delivery of one or more active agents with zero-order kinetics by a combination of photolithography and reactive ion etching techniques comprising the steps of: (i) providing a platform comprising a first surface and a second surface, wherein the first surface comprises one or more trenches, cavities or depressions, wherein each of the one or more trenches, cavities or depressions comprise one or more holes, perforations or patterns, (ii) placing a first substrate in the trenches, cavities or depressions, wherein the substrate may optionally be held in place in the trench by using an adhesive (iii) depositing at least one masking layer on the platform and the first substrate, (iv) depositing at least one photo-resist layer on the first substrate, (v) defining one or more holes, perforations or patterns on the photo-resist layer by lithography, (vi) performing a first reactive ion etching step using a reactive plasma to transfer the holes, perforations or patterns through the masking layer, and (vii) performing a second reactive ion etching step using the reactive plasma to transfer the holes, perforations or patterns through a wall of the first substrate to form the device for delivery of one or more active agents with zero-order kinetics. In specific aspects the first substrate is a planar or a non-planar substrate and is a cylindrical polymer tube of polyimide. In one aspect a platform material is selected from the group consisting of a polymer, a rubber, a metal, a semiconductor, a dielectric, a mineral, a ceramic, and a glass. In a specific aspect the platform material is silicon. In another aspect a mask material is selected from the group consisting of a polymer, a rubber, a metal, a semiconductor, a dielectric, a mineral, a ceramic, and a glass. In another aspect the mask material is selected from the group consisting of chromium, aluminum, titanium, silicon dioxide, silicon nitride, and diamond like glass. In yet another aspect the lithography is selected from the group consisting of photolithography, imprint lithography, electron beam lithography, scanning probe lithography, nanosphere lithography, and combinations and modifications thereof.

The silicon-wafer mold used in the method described above is made by a process comprising the steps of: (i) providing the silicon-wafer substrate comprising a first surface and a second surface, (ii) forming one or more trenches on the first surface or on the second surface by a method comprising the steps of: (a) depositing at least one etching mask layer on the silicon-wafer substrate; (b) spin-coating a photo-resist layer onto the etching mask layer; (c) creating a trench structure on the photo-resist layer by using a photolithographic technique; (d) aligning a desired trench direction and creating of one or more alignment marks on the substrate, wherein the alignment marks are used to position the first substrate; (d) transferring the trench structure through the one or more etching mask layers to the silicon-wafer substrate by the reactive ion etching technique using a reactive plasma, and (e) fabricating the trench structure by removal of any residual substrate or substrate-layer materials from the formed trenches by a wet anisotropic etching step.

In one aspect a selection of the silicon-wafer substrate is dependent on the shape of the trench structure to be transferred. In another aspect a depth and a width of the trench structure is dependent on a geometry of the photo-resist layer and a duration of the anisotropic etching step. In yet another aspect the etching mask layer is a silicon nitride layer. In one embodiment the method provides a device for delivery of one or more active agents with zero-order kinetics made by the method described hereinabove.

In one embodiment the instant invention discloses a method for making a cylindrical device for delivery of one or more active agents with zero-order kinetics comprising the steps of: providing a silicon wafer mold comprising a first and a second surface, wherein the first surface comprises one or more cylindrical trenches, wherein the one or more cylindrical trenches comprise one or more circular holes or perforations, placing a polyimide tube in the trench, wherein the tube may optionally be held in place in the trench by using an adhesive, performing an optional step of pushing the tube to the bottom of the trench by using a substrate, and transferring the circular holes or the perforations in the one or more trenches to the polyimide tube by reactive ion etching using plasma to make the cylindrical device for the delivery of the one or more active agents.

In one aspect the method further comprises the step of loading an active agent supply in the delivery device by a method selected from the group consisting of capillary action, dipping, injecting, and pressure loading using positive or negative pressures. In another aspect the method further comprises the optional step of flipping the silicon wafer prior to the step of transferring the circular holes, wherein the flipping results in the second surface facing the etching sources, wherein the etching sources are selected from the group consisting of, ions, etching gases, plasma, laser beams. In another aspect the one or more active agents comprise a solid, a liquid dosage, a semi-solid, a powder or a hydrogel. In another aspect the device may optionally be attached to a medical device or a microelectronic circuit, wherein the microelectronic circuit comprises at least one of a sensor, a transmitter, a receiver, a transceiver, a switch, a power supply, or a light. In yet another aspect the circular holes or the perforations range from 1 nanometers-1 centimeter, 100 nanometers-100 microns, 1 micron-50 microns, 10-30 microns, 15-25 microns or 20 microns In another aspect the method comprises the optional step of polymer coating the device thereby preventing a release of the one or more active agents until the coating is removed, which then causes release of the one or more active agents at a substantially constant rate. In another aspect the one or more active agents are selected from the group consisting of drugs, proteins, vitamins, minerals, saccharides, lipids, nucleic acid, peptides, manure, plant nutrients, chemicals, perfumes, fragrances, flavoring agents, animal feed, effervescent gas releasing agents, and combinations and modifications thereof. In one embodiment the present invention discloses a cylindrical delivery device for one or more active agents made by the method described above.

In another embodiment the present invention provides for a method for treating a medical condition in a patient comprising the steps of: identifying the a patient exhibiting at least one symptom of the medical condition and implanting an impermeable therapeutic agent delivery device comprising a therapeutic agent supply capable of providing an effective dose for the medical condition symptom, wherein the delivery device releases the therapeutic agent with zero-order kinetics. In one aspect the medical condition is selected from the group consisting of a cardiovascular disease, diabetes, epilepsy, Parkinson's disease, pain, cancer, ocular disease, and a fungal infection, wherein the cardiovascular disease is selected from the group consisting of stenosis, restenosis, late stent thrombosis, stroke, myocardial infarction, congestive heart disease, high blood pressure, angina, atherosclerosis or thrombosis. The diabetes is selected from the group consisting of type 1 diabetes, type 2 diabetes, juvenile diabetes, and gestational diabetes. The epilepsy is selected from the group consisting of generalized epilepsy, and partial epilepsy. The pain condition may result from an anatomical site selected from the group consisting of abdomen, ankle, anal, back, bones, breast, ear, elbow, eye, finger, foot, groin, head, heel, hip, joints, knee, leg, muscles, neck, rib cage, shins, shoulder, flank, teeth, wrist or somatoform. The ocular disease comprises macular degeneration, glaucoma, uveitis, retinitis, corneal ulcer or endophthalmitis. The cancer is selected from the group comprising lung cancer, brain cancer, cervical cancer, uterine cancer, liver cancer, leukemia, Hodgkin's lymphoma, Non-Hodgkin's lymphoma, kidney cancer, ovarian cancer, skin cancer, testicular cancer, and thyroid cancer. The fungal infection comprises a toenail infection or a fingernail infection.

In one aspect the therapeutic agent delivery device is made by the method comprising the steps of: providing a mold comprising a first surface and a second surface, wherein the first surface comprises one or more trenches, cavities or depressions, wherein a shape of the trench is selected from the group consisting of a cylinder, an oval, a cone, a sphere, and a cuboid, wherein each of the one or more trenches comprise one or more holes or perforations, placing a first substrate in the trench, wherein the substrate may optionally be held in place in the trench by using an adhesive, and transferring a shape of the holes or the perforations in the one or more trenches to the first substrate by one or more microfabrication techniques to make the device for the delivery of the therapeutic agent. In another aspect the shape of the one or more holes or perforations is selected from the group consisting of a triangle, a polygon, an undecagon, a trapezium or trapezoid, a quadrilateral, an icosagon, a star polygon, an annulus, a circle, a crescent, an ellipse, an oval, an arbelos, a Reuleaux triangle, a semicircle, a sphere, an Archimedean spiral, an astroid, a deltoid, a super ellipse, and a tomahawk.

The drug delivery device of the present invention is biodegradable and bioresorbable. The therapeutic agent supply comprises a pharmaceutically acceptable formulation. The drug delivery device comprises a surface that is configured for a controlled release of drug supply into an anatomical site, wherein the controlled release is maintained at a substantially constant rate thereby resulting in zero-order kinetics. The device disclosed herein is capable of releasing drugs into a body lumen for a time period ranging from days to several years, wherein the rate and extent of release is dependent on the drug solubility, dimensions of the device and passageway, and density of drug(s) loaded inside the device. The drugs can be in a form selected from the group comprising a liquid form, a solid form, or any other form known in the art. In one embodiment, the drug comprises a class of the biopharmaceutical classification system (BCS). In one embodiment, a BCS class is selected from the group consisting of Class I (High permeability, High solubility); Class II (Low solubility, Low Permeability); Class III (High Solubility, Low Permeability); or Class IV (Low solubility, Low permeability). The device of the present invention can comprise a single unit or a plurality of units.

DESCRIPTION OF THE DRAWINGS

A more complete understanding of embodiments of the disclosure will be apparent from the detailed description taken in conjunction with the accompanying drawings in which:

FIG. 12A-12F illustrates one embodiment of a method for fabricating "U" or "V" shaped trenches on a silicon wafer. All images show cross-sectional views;

FIG. 13A is the top side of the mold; FIG. 13B is the backside of the mold; FIG. 13C is a single window structure;

FIGS. 13D-13E shows several steps to fabricate one embodiment of an impermeable therapeutic drug delivery device: FIG. 13D presents a scanning electron microscopic image of a "U" shaped trench pattern; FIG. 13E presents an optical microscopic image of a circular passageway through a polyimide tube made by photolithographic technique;

FIGS. 14A and 14B is a schematic of a process flow for etching holes on tubes with the help of a silicon mold;

FIGS. 15A-15E shows one embodiment of a schematic for the process flow fabricating micro-holes on a polymer tube. All images show cross-sectional views;

DESCRIPTION OF THE INVENTION

Figure 1:
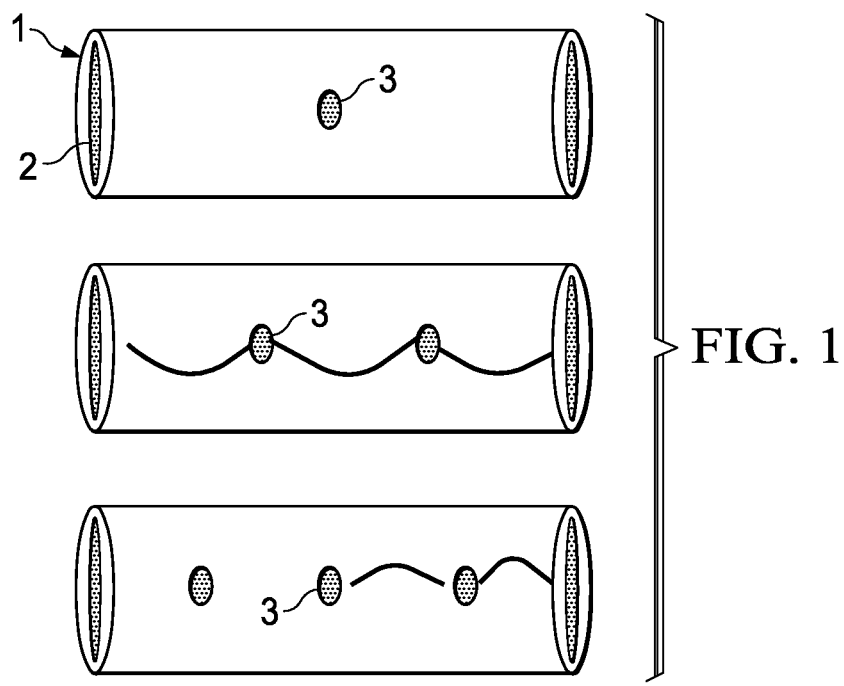
FIG. 1 is a tubular drug delivery device having an inner lumen that serves as drug reservoir and surface perforations that enable drug release from the device.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Before any embodiments of the invention are described in detail, it is to be understood that the invention is not limited in its application to the details of construction and the arrangement of components set forth in the following description. The invention is capable of other embodiments and of being practiced or of being carried out in various ways. Also it is to be understood that the phraseology and terminology used herein is for the purpose of description and should not be regarded as limiting. The use of "including," "comprising," or "having" and variations thereof herein is meant to encompass the items listed thereafter and equivalents thereof, as well as additional items.

As used herein the term "mold" refers to a solid support used to hold a substrate or material and to transfer a shape to the substrate. The substrate may have different desired shapes and sizes prior to being placed in the mold, or the mold may partially or completely reshape the substrate. The substrate is either placed, physically shaped, or poured into the mold to transfer a particular and/or contemplated opening, shape, structure or component by one or more techniques including but not limited to lithography, imprinting, thermal and pressure molding, laser ablation, etching (e.g., reactive ion etching), ion milling, and other microfabrication techniques. The term includes both stationary molds for processing a batch and moveable molds for continuous casting.

The term "therapeutic agent delivery device" or "unit" as used herein, refers to any device having a housing comprising an impermeable matrix material encompassing a therapeutic agent filled hollow core. The device may be constructed such that the impermeable matrix material contains at least one passageway capable of releasing the encompassed drug wherein the ends of the device is plugged using a bioglue (i.e., for example, a albumin-glutaraldehyde composition). Alternatively, the device may be constructed such that the hollow core comprises an open end (i.e., for example, an outlet port) wherein the housing is devoid of passageways.

The term "housing" as used herein, refers to any impermeable matrix material, of any shape or size, encompassing a hollow core that is capable of supporting the formation of at least one passageway. For example, the housing may be in the shape of a cylinder and comprise from one to three passageways extending between the housing surface and the encompassed hollow core.

The term "hollow core" as used herein, refers to any open space encompassed by a housing, configured to contain a therapeutic agent supply composition and/or formulation.

The term "passageway" or "channel" as used herein, refers to any means by which a drug molecule is transported from the hollow core, through and out of the housing. Such means may include but are not limited to, an aperture, orifice, bore, channel outlet, or hole. The number and size of the "passageway" may be selected to tailor make the rate and extent of release of the agents. For example, the diameter of a passageway may range from several nanometers to several centimeters. Preferably, the diameter of a passageway ranges between approximately 1 nanometers-1 centimeter. More preferably, the diameter of a passageway ranges between approximately 100 nanometers-750 microns. Even more preferably, the diameter of a passageway ranges between approximately 5 microns (i.e., micrometers)-500 microns (i.e., micrometers). Preferably, the diameter of a passageway ranges between approximately 20 microns-100 microns.

The term "outlet port" as used herein, refers to any open end of a hollow core.

The term "therapeutic agent" as used herein, refers to any pharmacologically active substance capable of being administered which achieves a desired effect. Such agents can be synthetic or naturally occurring, non-peptide, proteins or peptides, oligonucleotides or nucleotides, polysaccharides or sugars.

The term "administered" or "administering" a therapeutic agent, as used herein, refers to any method of providing an agent to a patient such that the agent has its intended effect on the patient. For example, administering may include but not limited to, local tissue administration (i.e., for example, via a drug delivery device), oral ingestion, transdermal patch, topical, inhalation, suppository etc.

The term "therapeutic agent supply" as used herein, refers to any drug depot or reservoir in a form including, but not limited to, a solid composition, a hydrogel, a colloid, a suspension, solution, or powder that is placed within a hollow core.

The term "drug" as used herein, refers to any therapeutically or prophylactically active agent, wherein the agent obtains a desired diagnostic, physiological, or pharmacological effect. For example, a drug may include, but is not limited to, any compound, composition of matter, or mixture thereof that may be natural or synthetic, organic or inorganic molecule or mixture thereof which may be used as a therapeutic, prophylactic, or diagnostic agent. Some examples include but are not limited to chemotherapeutic agents such as 5-fluorouracil, paclitaxel, sirolimus, adriamycin, and related compounds; antifungal agents such as fluconazole and related compounds; anti-viral agents such as trisodium phosphomonoformate, trifluorothymidine, acyclovir and related compounds; cell transport/mobility impending agents such as colchicine, vincristine, cytochalasin B and related compounds; antiglaucoma drugs such as beta blockers: timolol, betaxolol, atenolol, an related compounds; peptides and proteins such as insulin, growth hormones, insulin related growth factors, enzymes, and other compounds; steroids such as dexamethasone, prednisone, prednisolone, estradiol. ethinyl estradiol, and similar compounds; antihypertensives, anti-convulsants, blood glucose lowering agents, diuretics, painkillers, blood thinning agents, anesthetics, antibiotics, antihistaminics, immunosuppressants, anti-inflammatory agents, anti-oxidants, in vivo diagnostic agents (e.g., contrast agents), sugars, vitamins, toxin antidotes, and molecules developed by gene therapy.

The term "bodily fluid" as used herein refers to any liquid-like or semi-solid composition derived from an organism including but not limited to blood, serum, urine, gastric, and digestive juices, tears, saliva, stool, semen, and interstitial fluids derived from tumored tissues.

The term "analyte" as used herein, refers to any compound within a body fluid including, but not limited to, a small organic molecule, a mineral, an inorganic ion, a protein, or a hormone.

The term "biopharmaceutical classification system" or "BCS" as used herein, refers to a scientific classification framework for drug substances based on their aqueous solubility and intestinal permeability (US Dept. Health & Human Services, Food and Drug Administration Center for Drug Evaluation and Research (CDER) August 2000).

The term "permeability" as used herein, refers to any material that permits liquids or gases to pass through. The term "impermeable" as used herein, refers to any material that does not permit liquids or gases to pass through.

The term "solubility" as used herein, refers to the amount of a substance that will dissolve in a given amount of another substance. Typically solubility is expressed as the number of parts by weight dissolved by 100 parts of solvent at a specified temperature and pressure or as percent by weight or by volume.

The term "controlled release" as used herein, refers to a predictable dissolution of a therapeutic agent supply that may be described by mathematical relationships. For example, a controlled release may follow zero order kinetics.

The term "zero-order kinetics" as used herein, refers to a constant controlled release of a therapeutic agent wherein the release rate that does not change during the dissolution of a therapeutic drug supply (i.e., the release rate maintains linearity throughout the dissolution of the drug supply).

The term "substantially constant rate" as used herein, refers to a zero order kinetic release of a therapeutic agent wherein a regression coefficient is at least 0.90 (i.e., for example, $R^2$)

The term "long-term administration" as used herein, refers to any therapeutic agent that is given to a patient or subject at greater than a single dose equivalent. For example, such administration may comprise multiple doses on a single day or a single dose over several days. Alternatively, such administration may comprise a continuous substantially constant rate over the time period comprising hours, days, week or years.

The term "geometrical shape" as used herein, refers to any custom designed composition that is formulated for implantation into a specific anatomical site of a biological organism. For example, such compositions may include but are not limited to, a cuboid, a cube, a sphere, a cone, an oval, or a cylinder. In particular, a cube is shaped having six sides of equal area whereas a cuboid in the broadest sense includes, but is not limited to, polygonal, rhombus, trapezoid, rectangular, and square cross-sectional shapes with substantially squared or rounded corners and with perpendicular or angled sides.

The term "loading" or "loaded" as used herein, refers to the placement of a therapeutic agent supply within the hollow core of a drug delivery device. On the other hand, a device may be provided that is "preloaded" with a therapeutic agent supply, The term "body lumen" as used herein, refers to any cavity of a tubular body organ (i.e., for example, the interior of a blood vessel).

The term "biocompatible" as used herein, refers to any material does not elicit a substantial detrimental response in the host. There is always concern, when a foreign object is introduced into a living body, that the object will induce an immune reaction, such as an inflammatory response that will have negative effects on the host. In the context of this invention, biocompatibility is evaluated according to the application for which it was designed: for example; an implanted medical device (i.e., for example, an impermeable therapeutic agent delivery device) is regarded as biocompatible with the internal tissues of the body. Preferably, biocompatible materials include, but are not limited to, biodegradable and biostable materials.

The term "biodegradable" as used herein, refers to any material that can be acted upon biochemically by living cells or organisms, or processes thereof, including water, and broken down into lower molecular weight products such that the molecular structure has been altered.

The term "bioresabsorbable" as used herein, refers to any material that is assimilated into or across bodily tissues. The bioresorption process may utilize both biodegradation and/or bioerosin.

The term "non-biodegradable" as used herein, refers to any material that cannot be acted upon biochemically by living cells or organisms, or processes thereof, including water The term "non-bioreabsorbable" as used herein, refers to any material that cannot be assimilated into or across bodily tissues. The term "medical device" as used herein, refers broadly to any apparatus used in relation to a medical procedure and/or therapy. Specifically, any apparatus that contacts a patient during and/or after a medical procedure or therapy is contemplated herein as a medical device. Similarly, any apparatus that administers a compound or drug to a patient during or after a medical procedure and/or therapy is contemplated herein as a medical device. Such devices are usually implanted and may include, but are not limited to, urinary and intravascular catheters, dialysis shunts, wound drain tubes, skin sutures, vascular grafts and implantable meshes, intraocular devices, implantable drug delivery systems (i.e., for example, a stent or eye buckle) and heart valves, and the like. A medical device is "coated" when a medium (i.e., for example a polymer) comprising a therapeutic agent becomes attached to the surface of the medical device. This attachment may be permanent or temporary. When temporary, the attachment may result in a controlled release of a drug.

The term "attached" as used herein, refers to any interaction between a medium (or carrier) and a drug. Attachment may be reversible or irreversible. Such attachment includes, but is not limited to, covalent bonding, ionic bonding, Van der Waals forces or friction, and the like. A drug is attached to a medium (or carrier) if it is impregnated, incorporated, coated, in suspension with, in solution with, mixed with, etc.

The term "anatomical site" as used herein refers to any internal or external, deep or superficial body cavity, lumen, tissue, or organ of a mammalian organism. Some examples of anatomical sites where the medical device can be placed includes, but is not limited to, eyes, toenails, fingernails, epidermis (i.e., for example, skin), nasal cavity, gastro intestinal tract, valves, veins, and arteries such as coronary arteries, renal arteries, aorta, cerebral arteries, including for example, a cerebral arterial wall.

The terms "reduce," "inhibit" "diminish," "suppress," "decrease," "prevent" and grammatical equivalents (including "lower," "smaller," etc.) when in reference to the expression of any symptom in an untreated patient relative to a treated patient, mean that the quantity and/or magnitude of the symptoms in the treated patient is lower than in the untreated patient by any amount that is recognized as clinically relevant by any medically trained personnel. In one embodiment, the quantity and/or magnitude of the symptoms in the treated patient is at least 10% lower than, preferably, at least 25% lower than, more preferably at least 50% lower than, still more preferably at least 75% lower than, and/or most preferably at least 90% lower than the quantity and/or magnitude of the symptoms in the untreated patient.

The term "patient", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The term "derived from" as used herein, refers to the source of a compound or sequence. In one respect, a compound or sequence may be derived from an organism or particular species. In another respect, a compound or sequence may be derived from a larger complex or sequence.

The term "pharmaceutically" or "pharmacologically acceptable", as used herein, refer to molecular entities and compositions that for use in humans and other mammals that have been approved by a drug and medical device regulating authority or are under clinical development and have acceptable risk to benefit ratio.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term "formulation" as used herein, refers to any composition comprising a therapeutic agent intended for administration to a patient and/or subject. For example, a formulation may include, but not be limited to, a solid, a powder, a semisolid, or a gel.

This invention relates to methods of making a therapeutic agent delivery device which is capable of delivering a diagnostic, therapeutic, and/or prophylactic agent to a desired targeted site. Optionally, the delivery device may monitor bodily fluid analytes. Additionally, the method creates a device that can provide for the release of the agent from the device is unidirectional and at a controlled desirable rate. For example, the agent may include, but is not limited to, drugs, proteins, peptides, biomarkers, bioanalytes, and/or genetic material.

Miniature substrates, such as polymer micro-tubes, are finding increasing industrial and bio-medical applications. In many cases, the miniature substrates need further processing to fabricate specific structures to complete the desired devices. One example is to fabricate micro-holes on the surfaces of polymer tubes to form flexible drug release devices.

The method of laser ablation is commonly used to fabricate micro-holes on polymer tubes. It is a fast one-step process without using chemicals. However, the fabrication process is serial where the holes are made one by one limiting it to a low throughput manufacturing. For certain applications, a single device may require a large number of micro-holes on a tube. In this case, the manufacturing cost would be very high if the sequential laser ablation method is used.

To overcome the disadvantages of laser ablation, the present invention discloses a technology based on parallel processing to fabricate micro-holes on tubes employing lithography and reactive ion etching techniques. Such a parallel processing method is fast and low-cost and is well suited for mass production. In addition, the method has the potential to integrate electrical or electronic sensors and devices to control the drug delivery devices. However, the photo-resist and masking material used in the fabrication process may contaminate the tubes. The baking step used in photo-lithography and the chemicals used to clean the tubes after etching may change the properties of the polymer as well. It would be difficult to use this method to fabricate device structure using chemically unstable polymeric materials, e.g., bio-degradable tubes. Furthermore, due to the nonplanar surface of the tubes, the mask used for lithographic patterning may not protect tubes well during the etching process. As a result, cracks can develop on the tube surface, reducing the manufacturing yield. Since the method is based on a multi-step process: mask film deposition, photo-lithography, etching etc. to fabricate the device, an extensive facility equipped with the proper manufacturing tools is required, making the manufacturing method expensive.

The present invention discloses another method which retains the efficient approach of parallel processing but incorporates a simple molding method to form the micro-holes on flexible polymer tubes, including bio-degradable tubes. The process is fast, efficient, and low cost.

Although it is not necessary to understand the mechanism of an invention, it is believed that such a delivery device will eliminate the need for repeated dosing of a medicament thereby improving patient compliance. It is further believed that such a device would also decrease patient side effect risk, prolonged and unnecessary pain, and expense for many long term therapeutic regimens.

The instant invention uses a mold to fabricate micro-structures on miniature substrates such as micro-tubes. Trenches on the mold can hold tubes for convenient handling. The mold also has predefined configurations of through hole structures from the backside. These predefined through hole structures can be transferred to the desired positions on tubes in a single step of etching without any alignment and further manipulation. The mold can be reused for many batches. It is more efficient than laser ablation because it can process many tubes and fabricate many structures simultaneously. The process is simple and runs in a parallel manner. It is simpler than the micro-fabrication technique disclosed in U.S. Provisional Patent No. 61/225,352 because it requires no expensive processing steps, such as lithography, multiple thin film deposition and etching.

This invention simplifies significantly the process to fabricate microstructures on miniature substrates such as micro-tubes. Once the mold is formed, the fabrication process can be done in a single step. Except the parts exposed to the through holes of the mold, tubes under processing is intact. So the tubes are free of etching-induced cracks. Because it is a chemical-free process, it avoids any possible chemical contamination. It can also be easily applied to chemically unstable materials, e.g., bio-degradable tubes which are difficult to process by conventional micro-fabrication techniques without degrading the material properties of the tubes.

The disclosed invention combines the advantages of both laser ablation and micro-fabrication. Compared to laser ablation which is a serial process, the parallel nature of the present method enables a fast throughput thus reduces the manufacturing cost for mass production. The predefined structures on the mold make it free from any alignments and complex optics manipulating. Compared to the micro-fabrication technique disclosed in U.S. Provisional Patent No. 61/225,352 which is a multi-step process, it is a single-step process. This greatly shortens the manufacturing time and reduces both the material cost and investment on capital equipment. This crack-free process also improves the yield. Furthermore, the topside of the mold can also work as a template similar to the one in U.S. Provisional Patent No. 61/225,352. In another word, both sides of a tube can be processed by the mold technology disclosed herein. The polymer tubes or other substrates where the micro-holes are formed on can be integrated with microelectronics circuits and MEMS structures to form integrated devices for monitoring and controlled release of chemical agents or medications.

The present invention offers several advantages over existing drug delivery devices. One such advantage is to achieve zero order release kinetics without an initial burst effect such as is found in current designs that are known in the art. In its most basic form, the invention relates to a medical device which acts as a housing containing drug reservoir, and means for facilitating release of drug from the drug reservoir to an anatomical site. The device enables a mechanism in which the drug is released at equal increments from the reservoir per unit time.

One feature of the invention comprises simplicity of design and prolonged duration drug release capability up to, and including, several years. Further, drug release may be unidirectional is not subject to back transfer or build up of the drug as long as sink conditions are maintained. Although it is not necessary to understand the mechanism of an invention, it is believed that such a delivery device will eliminate the need for repeated dosing of a medicament thereby improving patient compliance. It is further believed that such a device would also decrease patient side effect risk, prolonged and unnecessary pain, and expense for many long term therapeutic regimens. In any drug treatment, it is desired to deliver a pharmaceutical agent directly at the targeted site for a sufficient duration in order to produce a required beneficial effect. Since the advent of time, man has sought means to find better cure. Oral, topical and inhalation are commonly used modes of drug administration. Modern era has witnessed development of alternate routes such as, systemic, intravitreal, and pulmonary delivery of drugs. However, age problems and disadvantages are associated with these conventional methods that restrict their effectiveness.

In most instances, drugs administered via these conventional routes result in the appearance of various deleterious side effects. For example, some drugs that are administered orally may not be properly absorbed through the stomach wall; may be degraded by the gastrointestinal tract; or may irritate the stomach causing an unwanted side effect. For example, insulin, which is a protein based drug, cannot be given orally since it would be degraded by proteolytic enzymes and therefore, must be given by injection. Further, Intravenous Ganciclovir (GCV) is effective in treatment of cytomegalovirus (CMV) retinitis in AIDS patients but 30-50% patients experience bone marrow toxicity resulting in neutropenia (neutrophil count <1000). Although an intravitreal administration of 200-400 µg/day of GCV twice a week has decreased the instances of neutropenia, this regimen requires repeated dosing thereby causing extreme discomfort to patients.

Some conventional routes of administration are problematic in maintaining a constant therapeutic level. For example, a drug concentration may either reach a toxic level or alternatively it may decrease as the drug is either metabolized (i.e., for example, by the liver) or eliminated (i.e., for example, by the kidney). Frequently, the drug levels may drop below the therapeutic levels and a second dose is needed.

One way to overcome this problem is to deliver drugs locally, that is, directly at the desired physiological site. A number of implantable drug delivery devices have been suggested to be capable of delivering a drug to a body lumen. One advantage of implanted drug delivery devices is related to local administration of a drug. Although it is not necessary to understand the mechanism of an invention, it is believed that local administration inherently improves efficacy and decreases side effects, as compared to other routes of administration such as oral, rectal, topical, or systemic. Nonetheless, one problem with the known implantable drug delivery devices is that the delivery rate cannot be controlled during all operational phases of the devices (i.e., for example, drug delivery rates may change thereby resulting in first order delivery kinetics or second order delivery kinetics).

Such problems result in a drug delivery device that administers drugs in an unpredictable pattern, thereby resulting in poor therapeutic benefit. For example, one popular drug delivery device is a drug eluting stent. Stents are mesh-like steel or plastic tubes that are used to open up a clogged atherosclerotic coronary artery or a blood vessel undergoing stenosis. A drug may be attached onto, or impregnated into, the stent that is believed to prevent re-clogging or restenosis a blood vessel. However, the initial release of the drug from a stent may be very rapid, thereby releasing 20-40% of the total drug in a single day. Such high concentrations of the drug have been reported to result in cytotoxicity at the targeted site. To maintain constant levels, a drug should be released from the delivery system at a rate which does not change with time (i.e., for example, zero order kinetics). In many systems however, the release rate is proportional to time (i.e., first order) or the square root of time (sometimes referred to as Fickian release kinetics).

A zero order drug controlled release system offers many advantages: i) Drug levels are continuously maintained at a desirable therapeutic range; ii) Adverse effects are reduced by targeting delivery to a specific site and avoiding distribution to unwanted tissues; iii) Dose of drug is decreased while mean residence time is increased; iv) Number of doses is decreased; v) Less invasive dosing decreases patient trauma and improves patient compliance; and vi) An inert and impermeable device protects the drug in the hostile environment.

Several implantable drug delivery systems have been reported which are capable of administering drugs at zero order rates. One of the earliest zero order devices was developed as an ocular insert as described in U.S. Pat. No. 3,618,604. The device was described as a sealed container having the drug in an anterior chamber. The device was capable of continuously releasing pilocarpine at a predetermined rate of 20-40 μg/hour for seven days for treating glaucoma. The ocular pressure level and pupil diameter were maintained throughout the 24-hour period of Ocusert placement. Nonetheless, as described in U.S. Pat. No. 4,014,335 certain problems have been identified with such devices such as the difficulty in sealing the margins to form a container. In addition, stresses and strains introduced into the membrane walls from deformation during manufacturing of the devices may cause the reservoir to rupture and leak.

Another such device, as described in U.S. Pat. No. 5,660,848 comprise a subdermal implant for uses as a contraceptive. This device was described as a central drug core; an intermediate polymeric layer controlling the rate of diffusion of drug; and the outer polymeric layer extending outwards from the intermediate layer. The device described in U.S. Pat. No. 5,660,848 does have problems. For example, the macroscopic size of the device releases significant amounts of the drug, progesterone, into the circulation causing problems of weight gain and vision loss in a small percentage of treated patients.

Osmotic minipumps have been reported as capable of providing zero-order drug release. One such device as described in U.S. Pat. No. 3,993,073 has a reservoir, which is formed of a drug carrier permeable to the passage of the drug and in which the drug has limited solubility. The wall is formed in at least a part of a drug release rate controlling material also permeable to the passage of the drug, but the rate of passage of the drug through the wall is lower than the rate passage of the drug through the drug carrier so that drug release by the wall is the drug release rate controlling step for releasing drug from the drug delivery device. Most of the osmotic pump devices are developed in form of a tablet or capsule, which can deliver drug up to a few hours or days and are not suitable for diseased conditions wherein, a constant amount of drug needs to be delivered for months and/or years.

Another minipump device, as described in U.S. Pat. Nos. 6,217,895 and 6,375, 972B1 comprises a sustained release device for the eye. This device is described as an inner core or reservoir including an effective agent; an impermeable tube which encloses the reservoir, at three sides; and a permeable membrane at the fourth side through which drug release takes place. The device is few hundred microns in dimensions and produces linear release. However, one drawback of the membrane based reservoir system is that the choice of the membrane is restricted by the solubility and diffusion coefficient of the drug. Consequently, a different membrane is required for each drug.

The problem of device size is extremely important in the design of devices as it dictates the variety of anatomical sites where it can be placed. A macro-sized device may be suitable for implantation in or near vertebrae but it may not be suitable for placement in an eye. Larger devices may also involve complex surgery both during implantation and removal. Furthermore, a larger device may also result in longer healing and recovery periods or device rejection by the body. Over the years, the dimensions of implantable drug delivery devices have decreased and the duration of release has increased. These reductions in size has improved immunological responses, biocompatibility, and reduced side effects associated with earlier devices. Hence, there remains a need for drug delivery device which can be optimized to deliver any therapeutic, diagnostic, or prophylactic agent for any time period up to several years maintaining a controlled and desired rate.

In some embodiment, the present invention contemplates methods and devices which comprise an injectable and/or implantable medical device having at least one orifice on the surface. Although it is not necessary to understand the mechanism of an invention, it is believed that the devices can be used to obtain a desired local or systemic physiological or pharmacological effect in mammals, e.g., humans. In one embodiment, the device comprises a hollow matrix of any size or shape, which can be made from materials including, but not limited to, metals and/or non metals. In one embodiment, the device comprises a reservoir capable of releasing at least one therapeutic, diagnostic, and/or prophylactic agent via the orifices to the desired anatomical site. In one embodiment, a perforated matrix can either be used individually, or as a set, which in turn can be either built as part of a device or mounted on a medical device, including, but not limited to, a stent. Although it is not necessary to understand the mechanism of an invention, it is believed that the presently contemplated device, due to its composite structure, has an ability to combine several release mechanisms, leading to controllable zero-order release kinetics. For example, such drug release may be dependent on factors including, but not limited to, drug solubility, dimensions of the matrix and orifice, and/or density of drug(s) loaded inside the device. It is further believed that, the composition provides zero-order kinetics, in part, because the diffusion rate of the drug from the device is slow which enables sink conditions. Hence, no back transfer or build up of drug occurs at anytime. Polymers are not required for controlled release.

I. Drug Release Kinetics: Over recent years, drug release/dissolution from solid pharmaceutical dosage forms has been of increasing interest. For example, whenever a new solid dosage form is developed or produced, drug dissolution studies are performed to determine the release characteristics (i.e., for example, kinetics) of the formulation. Sometimes, mathematic models are derived from a theoretical analysis of the observed kinetics. Usually, however, a theoretical concept is not applicable and empirical equations are applied instead. For example, drug dissolution from solid dosage forms has been described by kinetic models in which the dissolved amount of drug (Q) is a function of the test time, t or $Q=f(t)$. Some analytical definitions of the Q(t) function are commonly used, including, but not limited to, zero-order, first-order, Hixson-Crowell, Weibull, Higuchi, Baker-Lonsdale, Korsmeyer-Peppas and Hopfenberg models. Other release parameters, such as dissolution time (tx %), assay time (tx min), dissolution efficacy (ED), difference factor (f1), similarity factor (f2) and Rescigno index (xi1 and xi2) can be used to characterize drug dissolution/release profiles.

Much effort has been expended to develop zero-order drug release kinetics for various pharmaceutical drug formulations. Some having skill in the art believe that linear drug release provides a more stable therapeutic drug level over time and therefore provides a more predictable clinical response. Ideal drug delivery process would, therefore, be expected to exhibit zero-order kinetics. However, in practice, most conventional drug delivery processes follow first-order kinetics. Nonetheless, some mathematical models have determined that certain polymer shapes of drug micro-carriers that may support near zero-order release. Such mathematical models may be derived from the Carslaw and Jaeger equation of conduction of heat that models the relationship between carrier geometry shape and drug concentration. It has been suggested that by reducing the k value (i.e., for example, a ratio of volume of the fluid to that of the sphere) gives a near zero-order kinetics drug delivery response for most micro carrier geometry shapes that are roughly spherical in shape. On the other hand, tetrahedron shapes exhibits the best mathematical fit and tablets exhibit the worst mathematical fit. Ng et al., "*Optimization of Nanoparticle Drug Micro Carrier on the Pharmacokinetics of Drug Release: A Preliminary Study*" *J Med Syst.* 32:85-92 (2008).

Nonetheless, a tablet formulation with a zero-order drug release profile has been reported that is based on a balanced blend of three matrix ingredients. Specifically, matrices comprising Polyox®, Carbopol®, and lactose were evaluated for their effect on the release rate of theophylline. The tablets were prepared by direct compression and were subjected to an in vitro dissolution study. A balanced blend of these matrix ingredients could be used to attain a zero-order release profile. El-Malah et al., "*D-Optimal Mixture Design: Optimization of Ternary Matrix Blends for Controlled Zero-Order Drug Release from Oral Dosage Forms*" *Drug Dev Ind Pharm.* 32:1207-18 (2006). Other polymer based matrices have been produced that support zero-order delivery of the highly soluble drug alfuzosin hydrochloride. These matrices were reported to contain polyethylene oxide (PEO), hydroxypropylmethylcellulose (HPMC), sodium bicarbonate, citric acid and polyvinyl pyrrolidone. These drug release kinetics, matrix swelling and subsequent erosion during dissolution was suggested as suitable for a gastro-retentive drug delivery system in the proximal small intestine. Liu et al., "*Zero-Order Delivery of a Highly Soluble, Low Dose Drug Alfuzosin Hydrochloride Via Gastro-Retentive System*" *Int J Pharm* 348:27-34 (2008).

Zero-order extended release formulations have also been reported. For example, a gliclazide extended-release formulation was created using two hydrophilic polymers: HPMC K 15M and sodium alginate as retardant. Further, the effects of HPMC, lactose, and sodium alginate concentrations were studied for their effects on the gliclazide release rate. The drug release percent at 3, 6, 9 and 12 h were restricted to 20-30, 45-55, 70-80 and 90-100%, respectively. The mechanism of drug release from these extended-release matrix tablets was followed by a zero-order release pattern. Jin et al., "*Optimization of Extended Zero-Order Release Gliclazide Tablets Using D-Optimal Mixture Design*" *Yakugaku Zasshi* 128:1475-1483 (2008). An alternative extended release gliclazide tablet formulation was tested that had a central composite design with pH-dependent matrix forming polymers keltone-HVCR and eudragit-EPO. These tablets were evaluated for hardness, percent drug release after 1 hr, percent drug release after 6 hr, diffusion exponent and time required for 50% of drug release. One formulation, containing 8 mg of keltone-HVCR and 14.10 mg of eudragit-EPO, provides a sufficient hardness (>4.5 kg/cm2) and exhibited zero-order release properties. Vijayalakshmi et al., "*Development of Extended Zero-Order Release Gliclazide Tablets by Central Composite Design*" *Drug Dev Ind Pharm.* 34:33-45 (2008).

Glipizide hydrophilic sustained-release matrices have also been evaluated for in vitro-in vivo correlations (IVIVC) in the presence of a range of formulation/manufacturing changes. The effect of polymeric blends of ethyl cellulose, microcrystalline cellulose, hydroxypropylmethylcellulose, xanthan gum, guar gum, Starch 1500, and lactose on in vitro release profiles were studied and fitted to various release kinetics models. An IVIVC was established by comparing the pharmacokinetic parameters of M-24 and Glytop-2.5 SR formulations after single oral dose studies on white albino rabbits. The matrix M-19 (xanthan:MCC PH301 at 70:40) and M-24 (xanthan:HPMC K4M:Starch 1500 at 70:25:15) showed zero-order glipizide release. A Kopcha model analysis revealed that the xanthan gum has a determinative effect on the zero-order release profile. These data suggest that proper selection of rate-controlling polymers with release rate modifier excipients may determine overall release profile, duration and mechanism from directly compressed matrices. Sankalia et al., "*Drug Release and Swelling Kinetics of Directly Compressed Glipizide Sustained-Release Matrices: Establishment of Level A IVIVC*" *J Control Release* 129:49-58 (2008).

Osmotic minipumps have been reported as capable of providing zero-order drug release. For example, a monolithic osmotic pump tablet system (MOTS) containing isosorbide-5-mononitrate (5-ISMN) was evaluated for variations in tablet formulations such as, size and location of the delivery orifice, membrane variables, and pH value of the dissolution medium on 5-ISMN release from MOTS. These results demonstrated that the tablet core played a role in MOTS function, and membrane variables could also affect the 5-ISMN release rate. The optimal formulation of 5-ISMN MOTS was determined by a uniform design. Furthermore, the log pharmacokinetics and relative bioavailability of the test formulation (5-ISMN MOTS) have been compared with the reference formulation (Imdur(R): 60 mg/tablet, a sustained release, SR, tablet system) following an oral single dose of 60 mg given to each of six Beagle dogs. The mean drug fraction absorbed by each dog was calculated by the Wagner-Nelson technique. The results showed that drug concentration in plasma could be maintained more stable and longer after the administration of 5-ISMN MOTS as compared with the matrix tablets of Imdur(R), and a level A "in vitro/in vivo correlation" was observed between the percentage released in vitro and percentage absorbed in vivo. It was concluded that 5-ISMN MOTS is more feasible for a long-acting preparation than 5-ISMN SR tablet system as once-a-day treatment, and it is very simple in preparation, and can release 5-ISMN at the rate of approximately zero order for the combination of hydroxypropyl-methyl cellulose as retardant and NaCl as osmogent. Duan et al., "*Development of Monolithic Osmotic Pump Tablet System for Isosorbide-5-Mononitrate Delivery and Evaluation of it In Vitro and In Vivo*" *Drug Dev Ind Pharm* 31:1-9 (2008). Nonetheless, osmotic minipumps rely upon passage of analytes across semipermeable membranes that encompass a drug solution. Consequently, osmotic minipumps do not support zero order release kinetics using impermeable housing matrix materials.

II. Impermeable Drug Delivery Devices: Some embodiments of the present invention offer several advantages over existing drug delivery devices. One such advantage is to achieve stable zero order release kinetics without an initial burst effect such as is found in previously reported devices (supra). Although it is not necessary to understand the mechanism of an invention, it is believed that an impermeable housing encompassing a therapeutic agent supply plays a role in providing stable zero order release kinetics. Although it is not necessary to understand the mechanism of an invention, it is believed that a composition comprising a solid therapeutic agent supply plays a role in providing stable zero order release kinetics.

In one embodiment, the present invention contemplates a medical device comprising an impermeable housing encompassing a therapeutic agent (i.e., for example, a drug) supply (i.e., for example, a reservoir or depot). Some embodiments may also comprise at least one passageway or outlet port, thereby facilitating release of drug from the drug reservoir to an anatomical site. The device enables a mechanism in which the drug is released from the reservoir at equal increments per unit time (i.e., for example, a stable controlled desired release rate and/or zero order release kinetics). This capability allows embodiment of the present invention to release drugs for prolonged durations extending from several hours to several years.

Thus, the presently contemplated device presents an improved medical device which maintains its physical and chemical integrity in both the environments of use and in the presence of agent during the controlled and continuous dispensing of agent over a prolonged period of time. Additionally, due to composite design of the device, there is no need of any coating or polymers for controlled release of agents.

In one embodiment, the device may comprise a single housing, wherein the housing encompasses an agent supply comprising at least two therapeutic agents. In one embodiment, the device releases a first drug at a first release rate. In one embodiment, the device releases a second drug at a second release rate. Although it is not necessary to understand the mechanism of an invention, it is believed that the first and second agents are released at different rates because of differential solubility relative to the agent supply.

In one embodiment, the device may comprise at least two housings. In one embodiment, the first housing comprises large diameter passageways. In one embodiment, the second housing comprises small diameter passageways. In one embodiment, the first housing encompasses a first agent supply that is released at a first rate. In one embodiment, the second housing encompasses a second agent supply that is released at a second rate. Although it is not necessary to understand the mechanism of an invention, it is believed that the first agent is released at a faster rate than the second agent.

A. The Impermeable Housing: In some embodiments, the device housing comprises an impermeable composition, thereby providing unidirectional release. Although it is not necessary to understand the mechanism of an invention, it is believed that as long as the therapeutic agent supply does not disintegrate (i.e., for example, "sink conditions" are maintained), the device agent release function will not be compromised by agent back-transfer or build up of the agent within the passageways and/or outlet port.

The impermeable housing that encompasses a therapeutic agent supply with which the delivery device is made includes, but is not limited to, naturally occurring or synthetic materials that are biologically compatible with body fluids and tissues and are essentially insoluble and impermeable to the body fluid with which it will come in contact with. For example, these materials include, but are not limited to, glass, metal, ceramics, minerals, and polymers such as polyimides, polyamides, polyvinyl acetate, crosslinked polyvinyl alcohol, cross-linked polyvinyl butyrate, ethylene ethylacrylate, copolymer, polyethyl hexylacrylate, polyvinyl chloride, natural rubber, Teflon®, plasticized soft nylon, and silicone rubbers.

In one embodiment, the present invention contemplates a composition comprising a therapeutic agent supply, wherein the composition is impermeable to the passage of analytes that surround and/or encompass the agent supply. In one embodiment, the agent supply is in a form selected from the group consisting of a depot and/or reservoir. In one embodiment, the composition comprises a hollow cylindrical tube comprising at least one passageway on the surface of the composition. In one embodiment, the agent supply moves out of the reservoir through the hole at zero order. In one embodiment, the composition comprises at least one end that may be open or plugged using a biocompatible glue which may include, but is not limited to, cyanoacrylates, Bioglue®, epoxy resins, silastics, Teflon®, or polyimide adhesives.

In one embodiment, the present invention contemplates a method comprising releasing a therapeutic agent through the ends of the hollow core (i.e., for example, a cylindrical hollow tube) without any holes on the housing surface. In another embodiment, one of the ends is plugged using a biocompatible glue which may include, but is not limited to, cyanoacrylates, Bioglue®, epoxy resins, silastics, Teflon®, and polyimide adhesives.

B. The Therapeutic Agent Supply: In one embodiment, the present invention contemplates an impermeable therapeutic agent delivery device comprising a housing, wherein the housing encompasses a therapeutic agent supply. In one embodiment, the therapeutic agent supply comprises a solid. In one embodiment, the therapeutic agent supply comprises a semi-solid.

In one embodiment, the present invention contemplates a method of filling an impermeable therapeutic drug delivery device comprising a housing, wherein the housing is filled with a drug solution. In one embodiment, the method further comprises evaporating the solution to create a solid therapeutic agent supply. In one embodiment, the solid therapeutic agent supply comprises a powder. In one embodiment, the method further comprises evaporating the solution to create a semi-solid therapeutic agent supply. In one embodiment, the semi-solid agent supply comprises a gel. In one embodiment, the semi-solid agent supply comprises a hydrogel. In one embodiment, the semi-solid agent supply comprises a colloid.

The therapeutic agent enclosed in the impermeable matrix may include, but not limited to, ocular agents, anti-neoplastic and/or anti-mitotic agents, steroidal and non-steroidal anti-inflammatory agents, opioid analgesics and antagonists, anti-cholinergic drugs, adrenergic drugs, anti-adrenergic drugs, local anesthetics, respiratory system drugs, hormones and related drugs, anti-epileptic drugs, anti-parkinsonism drugs, drugs used in mental illness, cardiovascular drugs, and anti-microbial drugs.

Examples of such ocular agents for treatment of ocular diseases such as dry eye syndrome (DES), uveitis, and age related macular degeneration may include, but is not limited cyclosporine derivatives; doxycycline-induced protease inhibition; mucin secretion stimulants; adenosine receptor agonists; chloride channel stimulators; anti-TNF agents such as infliximab, adalimumab, and etanercept, anti-interleukin therapy such as daclizumab, and anakinra; interleukin 2 (IL-2) receptor antagonist, vascular endothelial growth factor (VEGF) inhibitors such as pegaptanib, ranibizumab, bevacizumab; and nuclear factor kappa B (NF-kB) inhibitors.

Examples of such antineoplastics and/or antimitotics may include, but not limited to paclitaxel, docetaxel, doxorubicin hydrochloride, methotrexate, azathioprine, vincristine, vinbiastine, and fluorouracil.

Examples of such steroidal and non-steroidal anti-inflammatory agents may include, but not limited to prednisone, dexamethasone, hydrocortisone, estradiol, triamcinolone, mometasone, fluticasone, clobetasol, and non-steroidal antiinflammatories, such as, for example, acetaminophen, ibuprofen, naproxen, adalimumab and sulindac.

Examples of such opioid analgesic may include, but not limited to morphine, codeine, thebaine, papaverine, noscapine. Examples of such opiod antagonist include naloxone and naltrexone.

Examples of such anti-cholinergic drugs may include, but not limited to atropine (e.g., for ophthalmic use as a cycloplegic; mydriatic), scopolamine (e.g., for ophthalmic use as in uveitis, iritis, and iridocyclitis), propantheline bromide (e.g., for treatment of enuresis).

Examples of such adrenergic drugs include, but not limited to noradrenaline, ephedrine, dopamine, phenylepherine, adrenaline, ephedrine, dobutamine, isoprenaline, adrenaline, isoprenaline, ephedrine, salbutamol, salbutamol, terbutaline, and nylidrine.

Examples of such anti-adrenergic drugs include, but not limited to phentolamine, tolazoline, prazosin, propanolol, timolol, oxprenolol, atenolol, oxprenolol, and alprenolol.

Examples of such local anesthetics include, but not limited to lidocaine, cocaine, tetracaine, benoxinate, benzocaine, butylaminobenzoate, and oxethazine.

Examples of such respiratory systems drugs include, but not limited to anti-tussives such as codeine, morphine, noscapine, oxeladin, and carbetapentane; antihistamines such as promethazine, diphenhydramine, chlorpheniramine; anti-asthmatic such as adrenaline, ephedrine, salbutamol, terbutaline, theophylline, atropine methonitrate, ketotifen, nedocromil, prednisolone, beclomethasone, and budesonide.

Examples of hormones and related drugs may include but not limited to propylthiouracil, carbimazole, cortisol, prednisolone, paramethasone, betamethasone, ethinyl estradiol, diethylstilbestrol, calcitonin, vitamin D, calcitriol. Examples of anti-epileptic drugs may include but not limited to phenobarbitone, primidone, phenytoin, mephenytoin, carbamazepine; trimethadione, cloanazepam, diazepam.

Examples of anti-parkinsonism drugs may include but not limited to, levodopa, bromocriptine, lisuride, apomorphine, carbidopa, benserazide, amantadine, deprenyl, trihexyphenidyl, and biperiden. Examples of drugs used in mental illness may include but not limited to, antipsychotics such as chlorpromazine, thioridiazine, haloperdol, droperidol, chlorprothixene, thiothixene; antianxiety drugs such as diazepam, lorazepam, alprazolam, propanolol, and anti-depressants such as phenelzine, tranylcypromine, deprenyl, and moclobimide.

Examples of cardiovascular drugs may include but not limited to, cardiac glycosides such as digitoxin, digoxin; anti-arrhythmic drugs such as quinidine, procainamide, propafenone, lidocaine, propanolol, verapamil, diltiazem; anti-anginal and anti-ischaemic drugs such as nitrogylcerine, isosorbide dinitrate; anti-hypertensives such as captopril, enalapril, thiazides, furosemide, spironolactone; anti-restenosis drugs such as pclitaxel, rapamycin, zotarolimus, and tacrolimus.

Examples of anti-microbial drugs may include but not limited to, antibacterial such as penicillins, aminoglycosides, and erythromycin; antifungal such as griseofulvin, ketoconazole; antiviral such as acyclovir, amantadine; antiprotozoal such as chloroquine, metronidazole; anthelmintic such as mebendazole, piperazine, and niclosamide.

Examples of such drugs undergoing clinical trials may include but not limited to, treatment of conditions such as prostate cancer (e.g., toremifene citrate, acapodene, flutamide, combination of docetaxel and estramustine, denosumab); brain tumors (e.g., karenitecin, topotecan) and eye diseases (e.g., valganciclovir for treatment of patients with CMV retinitis and AIDS; Celecoxib to treat macular degeneration).

C. The Release Passageways: In one embodiment, the delivery device comprises an impermeable matrix which has at least one passageway. Although it is not necessary to understand the mechanism of an invention, it is believed that the release of an agent is driven by diffusion and occurs through these passageways. For example, a hollow cylindrical tube is filled with the drug solution, which after evaporation of solvent changes to solid form. The ends of the tubes are sealed with a bioglue such that the passageways remain the only escape route for the drug. When the device comes in contact with the bodily fluid, the difference in concentrations of the drug inside and outside of the device causes the drug to diffuse into the bodily fluid having zero-order kinetics.

In one embodiment, the present invention contemplates a controlled release delivery device comprising a therapeutic agent supply, wherein the agent supply comprises a therapeutically effective amount of at least one agent effective in obtaining a diagnostic effect or effective in obtaining a desired physiological or pharmacological effect. In one embodiment, the delivery device comprises an impermeable housing.

In one embodiment, the present invention contemplates a stable controlled release delivery device configured to provide long-term therapeutic agent delivery. In one embodiment, the diameter the passageways range from the nanometer scale to the centimeter scale. In one embodiment, the diameter of the passageways range from approximately 5 nanometers-1 centimeter. In one embodiment, the diameter of the passageways range from approximately 100 nanometers-100 microns. In one embodiment, the diameter of the passageways range from approximately 1 micron-50 microns. In one embodiment, the diameter of the passageways range from approximately 10-30 microns. In one embodiment, the diameter of the passageways range from approximately 15-25 microns. In one embodiment, the diameter of the passageways are approximately 20 microns. The data presented herein show that release kinetics from a drug delivery device of the present invention having dimensions of approximately 20 mm long with a 125 micron inside diameter comprising 30 micron diameter passageways can be extrapolated to support long term stable controlled agent release for: i) approximately forty-three (43) years using a single passageway embodiment; ii) approximately twenty-two (22) years using double passageway embodiment; or iii) approximately fifteen (15) years using a triple passageway embodiment. See, FIG. 7.

Figure 6:
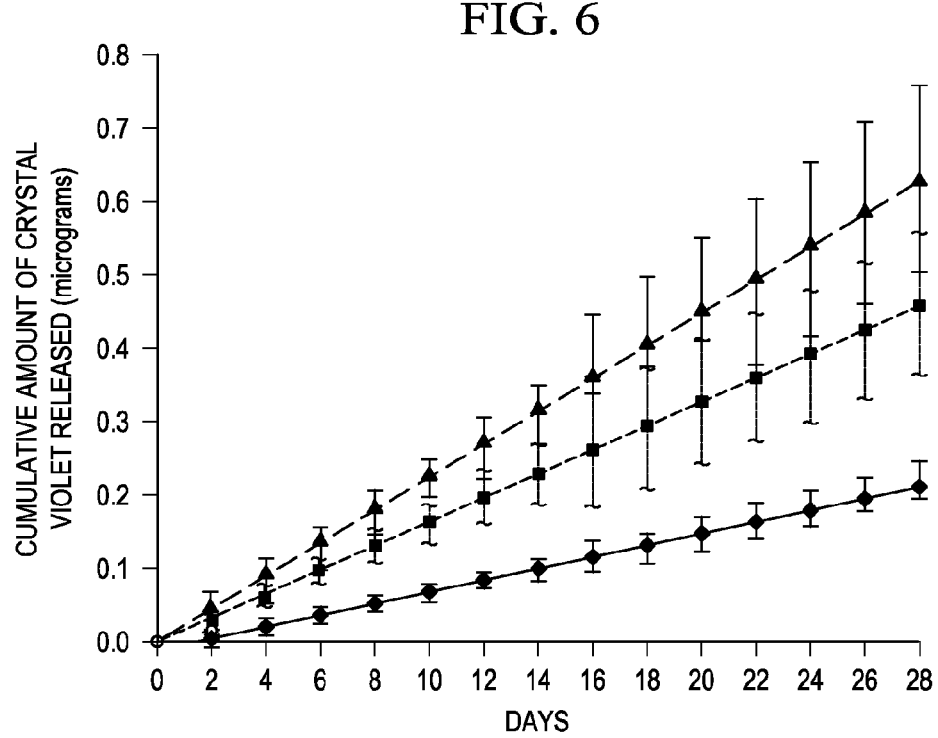
FIG. 6 is a graph illustrating cumulative zero order release of crystal violet from three types of drug delivery device that differ in the number of surface perforations.
Figure 7:
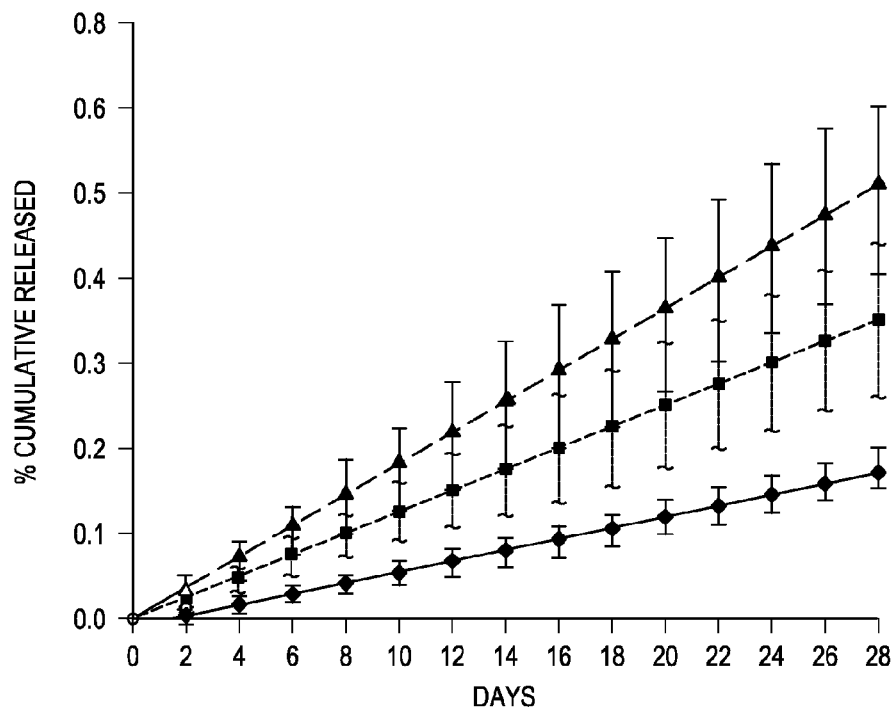
FIG. 7 is a graph illustrating cumulative percentage of crystal violet released from three types of drug delivery device that differ in the number of surface perforations.
Figure 8:
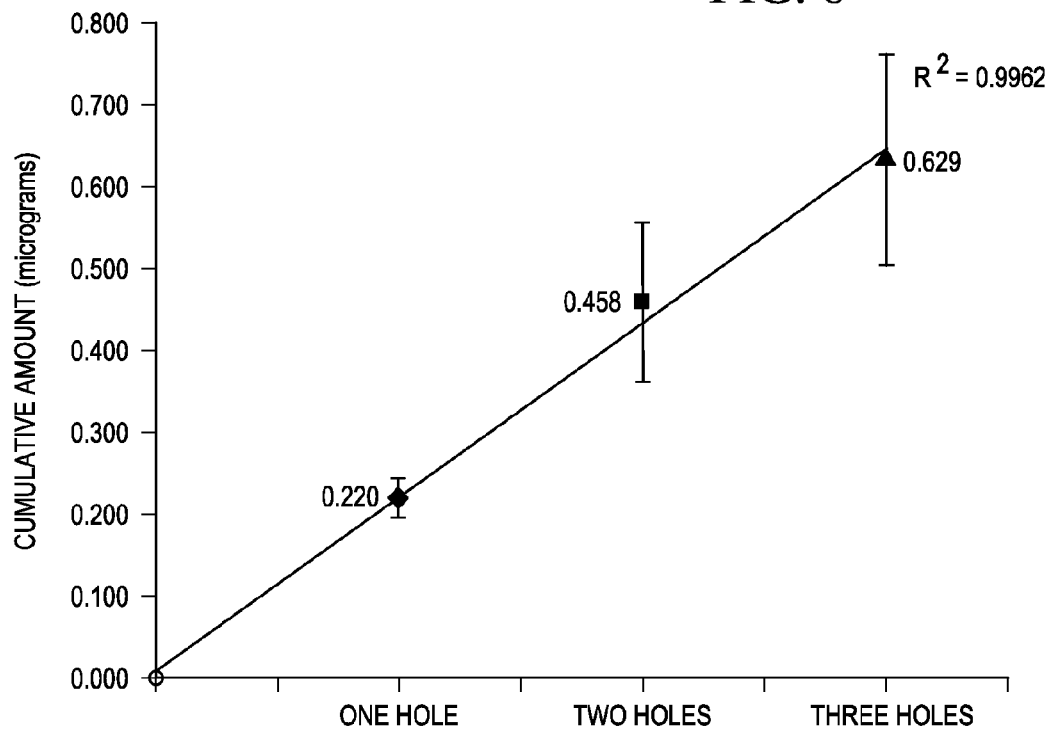
FIG. 8 is a graph illustrating the linearity of drug release from the drug delivery device in proportion to the number of holes.

A comparison of the release data from Examples II, IV, and VI shows that by increasing the number of similarly sized holes on a device, the agent release rate is a function of number of holes. Hence, an additive pattern in amount of drug released is observed. For example, the amount crystal violet released from a triple passageway impermeable delivery device and a double passageway impermeable device are approximately, three-fold and two-fold the amount released from a single passageway impermeable device, respectively, as shown in FIGS. 6-8.

D. The Release Outlet Ports: In another embodiment, the housing comprises a hollow core (i.e., for example, a cylindrical hollow tube) having at least one outlet port at the end of the core, but does not have any passageways on the housing surface (e.g., surface passageways). One end of the housing is sealed with a bioglue such that the other end is the only escape route for the therapeutic agent. On contact with a bodily fluid, the agent diffuses out having zero-order kinetics. Any biocompatible adhesive may be used to seal and plug unused outlet port(s) at the end of the tubes including, but is not limited to, mussel glue, frog glue, cyanoacrylates, Teflon® adhesive, polyimide adhesive, bioglue containing albumin and glutaraldehyde or similar compounds, silastic, epoxy resins and other commonly known glues and adhesives.

Figure 9:
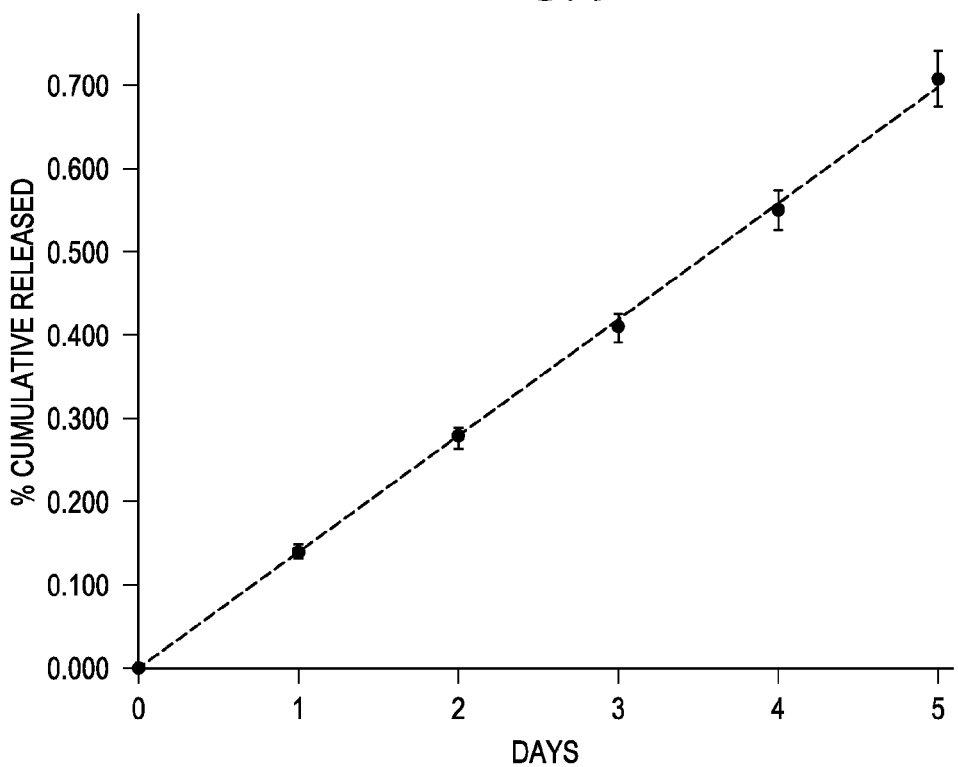
FIG. 9 is a cumulative percentage of crystal violet released from one open end of the drug delivery device with no perforations.

In one embodiment, the present invention contemplates a stable controlled release delivery device comprising at least one outlet port configured to provide long-term therapeutic agent delivery. In one embodiment, the diameter of the outlet port range from approximately 1-100 microns. In one embodiment, the diameter of the outlet port range from approximately 10-75 microns. In one embodiment, the diameter of the outlet port range from approximately 25-50 microns. In one embodiment, the diameter of the outlet port are approximately 30 microns. The data presented herein show that release kinetic from a drug delivery device of the present invention having dimensions of approximately 20 mm long with a 125 micro inside diameter comprising a 30 micron outlet port can be extrapolated to support long term stable controlled agent release for approximately two (2) years (FIG. 9).

A comparison of the crystal violet release data of Examples IX and II indicates that as the passageway diameter size increases, the release rate increases to an amount approximate to the square of ratio of the two radii (i.e., for example, $\{R_1/R_2\}^2$).

E. Medical Device Attachments: In some embodiments, the device can be incorporated (i.e., for example, attached) as part of any other drug delivery system including, but not limited to, bare metal stents, drug eluting stents, transdermal patches, retinal implants, cochlear implants, renal implants, grafts and transplants. In other embodiments, the device can be used as part of any medical procedure including, but not limited to, mechanical thrombectomy for treatment of stroke, drug eluting implants for cancer therapy, drug delivery device to deliver insulin, gene implant therapy, brain implants to reduce and prevent damage from Alzheimer's, Parkinson's syndrome, or epilepsia, and delivery of cholinesterase inhibitors, antiretroviral agents, and immunosuppressants to treat autoimmune disorders such as myasthenia gravis, and AIDS. Although it is not necessary to understand the mechanism of an invention, it is believed that optimizing therapeutic agent release from a device of the present invention utilize parameters including, but not limited to, the route of administration, targeted diseased condition, or desired release rate provide guidances as to the type of drug loaded, the amount of drug loaded, dimensions of the device, and dimensions and number of holes on the device surface.

In one embodiment, the present invention contemplates an impermeable drug delivery device attached to a stent. In one embodiment, the stent comprises a nondegradable polymer. In one embodiment, the non-degradable polymer stent may be selected from the group comprising Cypher Select® (sirolimus eluting, Cordis Johnson & Johnson) Taxus Liberti® (paclitaxel eluting, Boston Scientific) Endeavor® (zotarolimus eluting, Medtronic) ZoMaxx® (zotarolimus eluting, Abbott) Apollo® (paclitaxel eluting, InTek) Xience® (everolimus eluting, Abbott) or Promus® (everolimus eluting, Boston Scientific). In one embodiment, the stent comprises a degradable polymer. In one embodiment, the degradable polymer stent may be selected from the group comprising BioMatrix® (biolimus eluting, Biosensors) Infinnium® (paclitaxel eluting, SMT) Nobori® (biolimus eluting, Terumo) Champion® (everolimus eluting, Guidant), and CoStar® (paclitaxel eluting, Johnson & Johnson).

Despite the commercial availability, these drug eluting stents were designed and tested before the discovery of LST and its implications. Consequently, most FDA approved stents are still questionable for their long term usage. Hence, against the backdrop of these new complications, some embodiments of the present invention comprise therapeutic agent delivery devices that do not require a polymer to control agent release. Although it is not necessary to understand the mechanism of an invention, it is believed that such a device should be capable of delivering a combination of drugs at concentrations sufficient to inhibit restenosis without delaying the healing of the stent or inducing post-implantation complications including, but not limited to, LST or restenosis.

F. Microelectronic Integration: In one embodiment, the present invention contemplates an impermeable therapeutic agent delivery device, wherein the core, housing or other substrates can be integrated with microelectronics circuits and microelectromechanical systems (MEMS) structures. In one embodiment, the microelectronic circuit comprises a sensor. In one embodiment, the sensor comprises an analyte sensor. In one embodiment, the sensor comprises a transmitter, wherein the transmitter signal is received by a remote detector. In one embodiment, the analyte may be selected from the group including, but not limited to, an inorganic ion, a small organic molecule, a protein, a steroid hormone. In one embodiment, the protein comprises an insulin protein. In one embodiment, the device comprises an integrated solid circuit capable of monitoring and controlling the release of chemical agents or medications. In one embodiment, the device comprises an integrated solid circuit capable of monitoring body analytes and controlling the release of chemical agents or medications.

III. Preparation and Loading of a Therapeutic Agent Supply: In one embodiment, the present invention contemplates a method for loading a therapeutic agent supply comprising a drug delivery device and a therapeutic agent composition. In one embodiment, the composition comprises a solid. In one embodiment, the composition comprises a semi-solid. In one embodiment, the solid comprises a polymer matrix. In one embodiment, the semi-solid comprises a semi-solid. In one embodiment, the solid comprises a powder. In one embodiment, the loading means may be selected from the group comprising capillary (see, Example I), dipping, injecting, using positive or negative pressure, or other commonly known drug loading methods.

IV. Delivery Device Fabrication: In one embodiment, the present invention contemplates a process for fabricating a therapeutic device comprising micro-holes on non-planar substrates including, but not limited to, cylindrical polymer tubes.

In one embodiment, the present invention contemplates a process for fabrication of micro-holes on non-planar surfaces. In one embodiment, a micro-hole can be formed on a wide range of non-planar substrates, metal or non-metal, and with varying shapes, including cylindrical tubes. Depending on the application, a micro-hole can vary in size including, but not limited to, a fraction of a micron to hundreds of microns in diameter. In one embodiment, the present invention contemplates a fabrication process comprising photo-lithography and reactive ion etching. In another embodiment, the present invention contemplates a fabrication process using a mold. Devices containing micro-holes fabricated by the present invention can be used for a wide range of applications including, but not limited to, medical, bio-material, including implantable medical devices and controlled drug delivery systems. In one embodiment, the method is capable of fabricating micro-hole structures comprising complex geometries on non-planar substrates such as the micro electromechanical systems (MEMS) and microelectronics devices for a wide range of applications.

A. Background: The technology to fabricate micro-structures on planar silicon wafers is well developed and has led to the use of planar integrated circuits in everyday electrical and electronic devices. Planar technology can be extended to fabricate MEMS and nanotechnology devices for a wide range of applications in medicine and bio-materials. Nonetheless, planar microfabrication technology has many disadvantages when attempting to fabricate devices on non-planar substrates including, but not limited to, a cylindrical polymer tube.

For example, one common current method to fabricate micro-holes on a cylindrical tube is by laser ablation. Laser ablation is a serial process which is time consuming and difficult to be used for mass production. The laser ablation method has a number of limitations: i) the diameter of the micro-hole is normally larger than 15 microns; ii) it is difficult to control micro-hole shape; iii) it is difficult to control micro-hole depth; and iv) laser beam usually damages the material around the micro-hole.

Micro-structures or micro-devices on non-planar substrates can potentially be used for a wide range of applications for the pharmaceutical industry. The present invention describes a process of micro-fabrication to create micro-structures and micro-devices on non-planar substrates. The micro-structure fabricated by the disclosed method can be integrated into a support structure to form complex devices for a wide range of applications. In some embodiments, the present invention contemplates a process for fabricating micro-structures, and/or microdevices comprising micro-holes, wherein the microdevices comprise non-planar surfaces, comprising: 1) fabricating at least one trench on a planar substrate, such as a silicon wafer, to hold a micro-structure with a non-planar substrate such as a polymer tube; 2) fabricating a micro-hole on non-planar substrates using a combination of lithography, e.g., photolithography, reactive ion etching and/or chemical etching; 3) a non-planar substrate comprising either a metal or a non-metal having varying shapes capable of being placed into a planar support structure including, but not limited to, a silicon wafer trench: 4) micro-holes varying in size from a fraction of a micron to hundreds of microns, and 5) micro-holes varying in shape including, but not limited to, circular, rectangular, triangular, elliptical and square.

B. Delivery Device Fabrication Methods: The technologies to fabricate micro-structures on planar silicon wafers have been previously reported. But it is difficult to fabricate on non-planar substrate, including, but not limited to, a cylindrical polymer tube. Current methods to fabricate micro-holes on a cylindrical tube are usually performed by laser ablation. Laser ablation is a serial process which is time consuming and difficult to adopt for mass production. The micro-holes fabricated by laser ablation normally have diameters larger than 15 microns and it is difficult to control the shape and depth of the micro-hole. In addition, laser beam usually burns and damages the material around the micro-holes, which is not desirable for many medical applications.

The present invention contemplates a process for fabrication of passageways on non-planar surfaces. The passageway can be formed on a wide range of substrates, metal or non-metal, and shapes, such as tubes, depending on the application. The passageway varies in size from a fraction of a micron to hundreds of microns in diameter and can have a variety of shapes. In one embodiment, the fabrication process is based on lithography and reactive ion etching technologies.

In another embodiment, the process first fabricate a mold consisting of a substrate with trenches and through holes located in trenches, then a non-planar substrate is placed in the mold to form micro-hole structures by etching. Such devices containing the passageways of the present invention can be used for a wide range of medical and bio-materials applications, including the use for medical implantation and controlled drug delivery.

The modified lithographic technique described herein has many advantages over current techniques. For example, i) the process is a parallel process and suitable for mass production; ii) the process is associated with a lower cost; iii) the process greatly improves the capabilities and control in producing holes of non-circular shapes and varying sizes on non-planar surfaces; iv) the process can be integrated with MEMS and solid circuit sensors to form devices for a range of applications, including microelectronics, medical delivery and bio-materials.

The present invention discloses a process for fabrication of passageways on non-planar surfaces. Depending on the application, the passageways can be formed on a wide range of substrates, metal or non-metal, and with varying shapes including a tubular form. In some embodiments, passageway varies in size from a fraction of a micron (i.e., for example, approximately, 0.01 micron) to hundreds of microns (i.e., for example, 900 microns) in diameter.

Some embodiments of the present invention provide advantages over conventionally used microelectronic photolithographic processing technologies. For example, conventional photolithographic techniques are limited to planar surfaces, while the present invention has described photolithographic fabrication of non-planar surfaces (i.e., for example, metal or non-metal). In one embodiment, the fabrication comprises the etching of passageways (i.e., for example, micro-holes) on a non-planar surface. In one embodiment, a special structural element (i.e., for example, a trench pattern) is fabricated first on a silicon wafer to hold the non-planar surface material. The planar substrate can be any material other than a silicon wafer, depending on the structure and the application of interest. Accordingly, the process steps will have to be adjusted. Other trench structures with other shapes can be fabricated if desired, depending on the shape of the non-planar substrates.

This method provides significant advantages over current technology that fabricates micro-holes on a non-planar surfaces requiring laser ablation which is a time consuming serial process and expensive. On the other hand, the present invention discloses a process that can be performed in parallel and therefore is well-suited for mass production. This invention also provides another advantage by enabling the fabrication of a variety of passageways on many non-planar surfaces simultaneously, thus significantly reducing the manufacturing cost. In addition, the lithographic technique makes it possible to form individual passageways or a group of passageways having different sizes and shapes including, but not limited to, circular, elliptical, square and rectangular shapes.

FIG. 1 shows a top view of several embodiments of the invention. In each embodiment, a therapeutic agent delivery device 1 comprising a hollow cylindrical tube 2 is depicted which may be used as a reservoir for therapeutic agents (i.e., for example, a drug). The surface of the device comprises a plurality of passageways 3, wherein the holes on the device are equidistant from each other and from the end of the tube. Upper drawing: A device comprising a single passageway. Middle drawing: A device comprising two passageways. Lower drawing: A device comprising three passageways.

Figure 2:
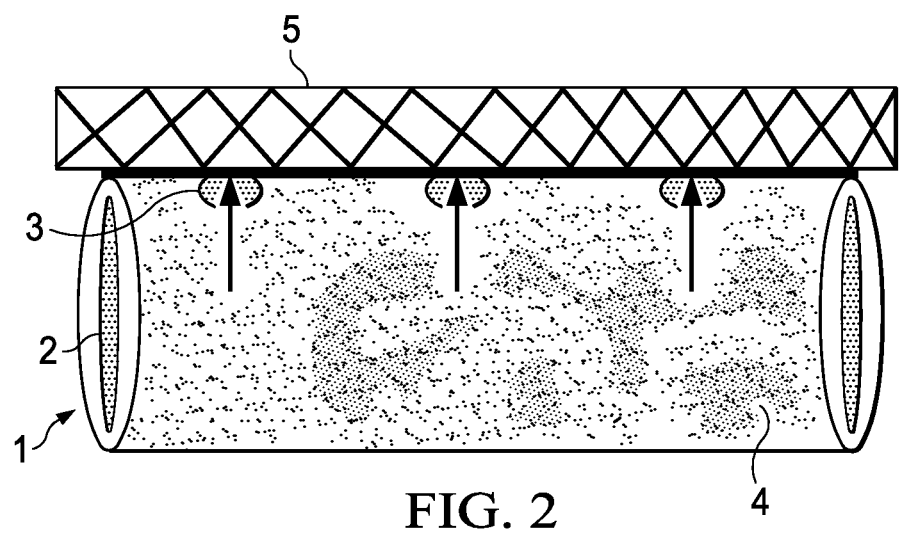
FIG. 2 is a cross-sectional view of the drug filled drug delivery device in contact with an anatomical site.
Figure 3:
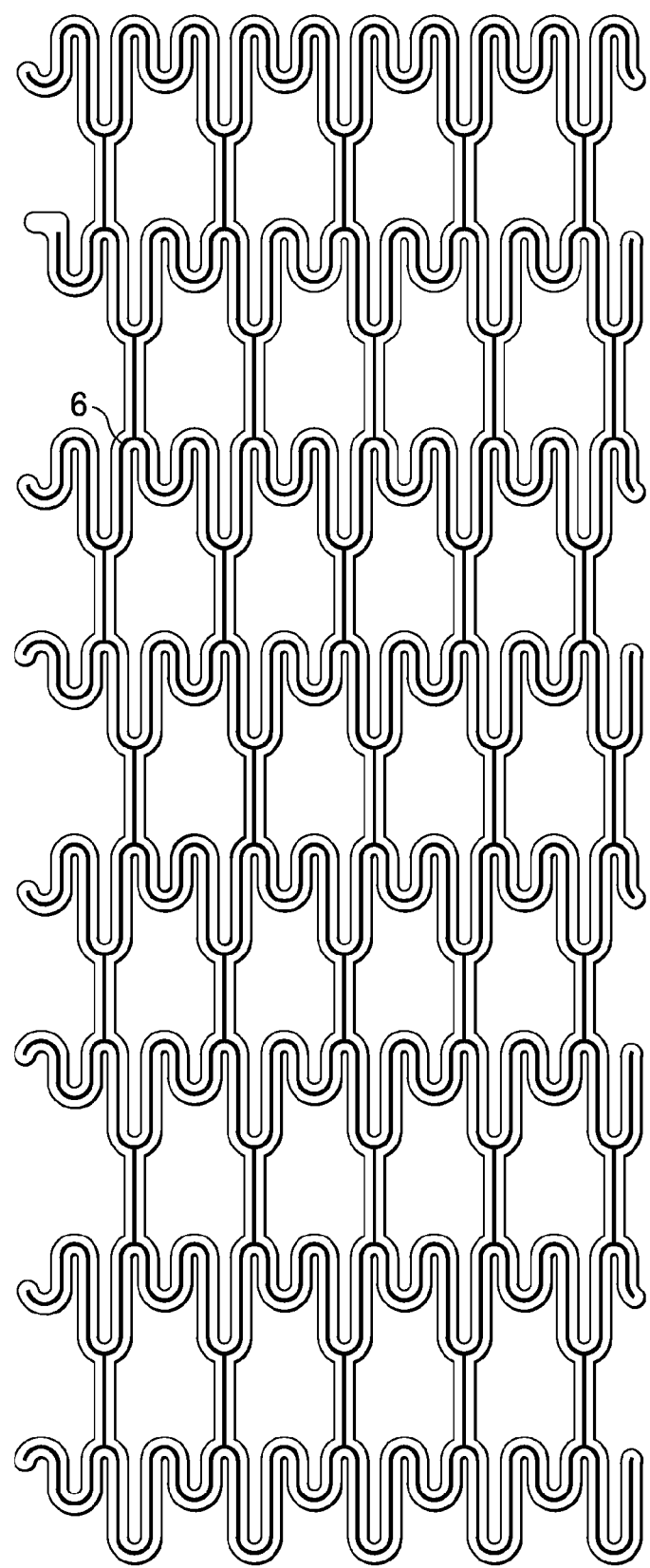
FIG. 3 is a carrier, for example, a stent structure to which the drug delivery device could be attached.
Figure 4:
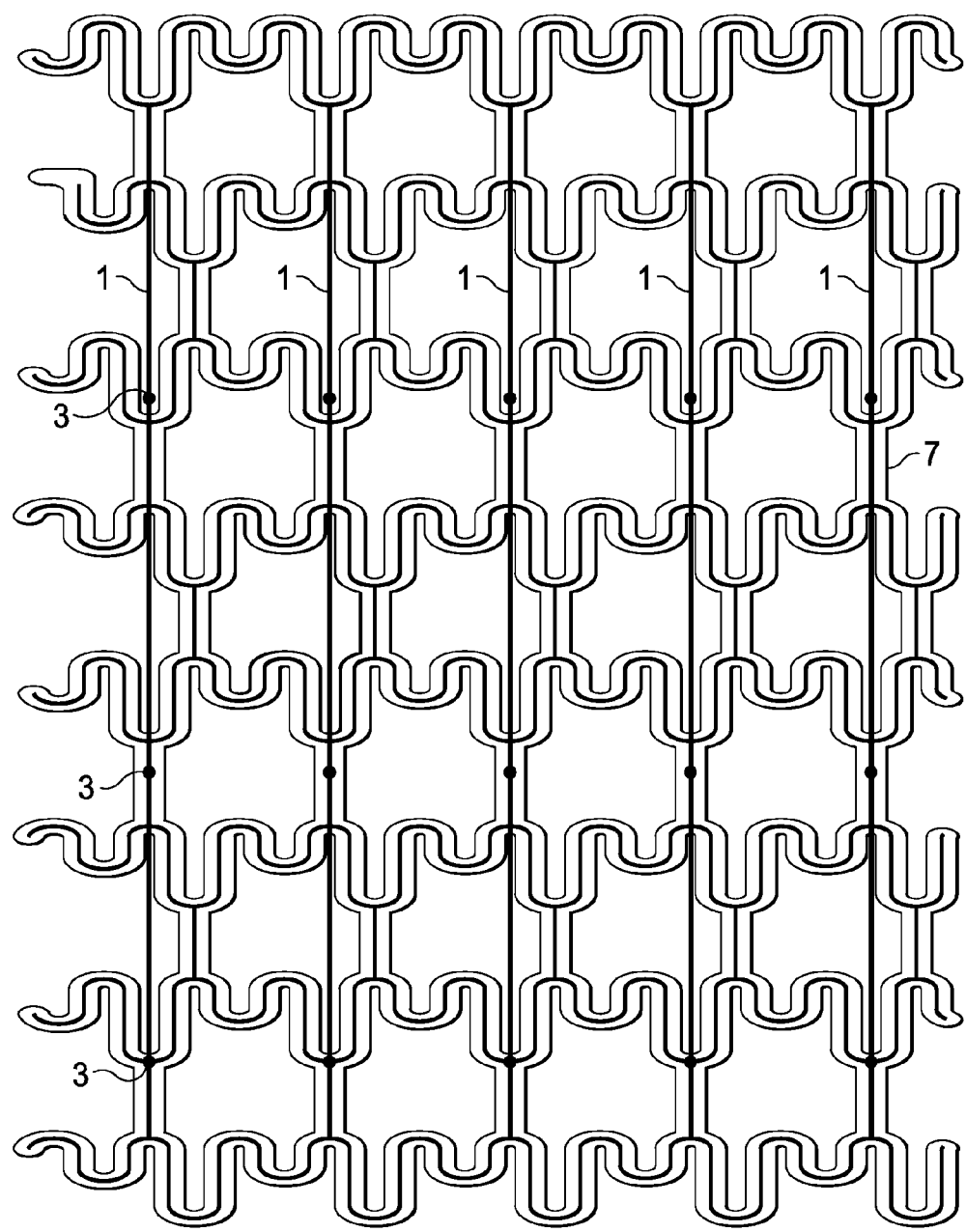
FIG. 4 is an example illustrating attachment of the drug delivery device to the carrier of FIG. 3.
Figure 5:
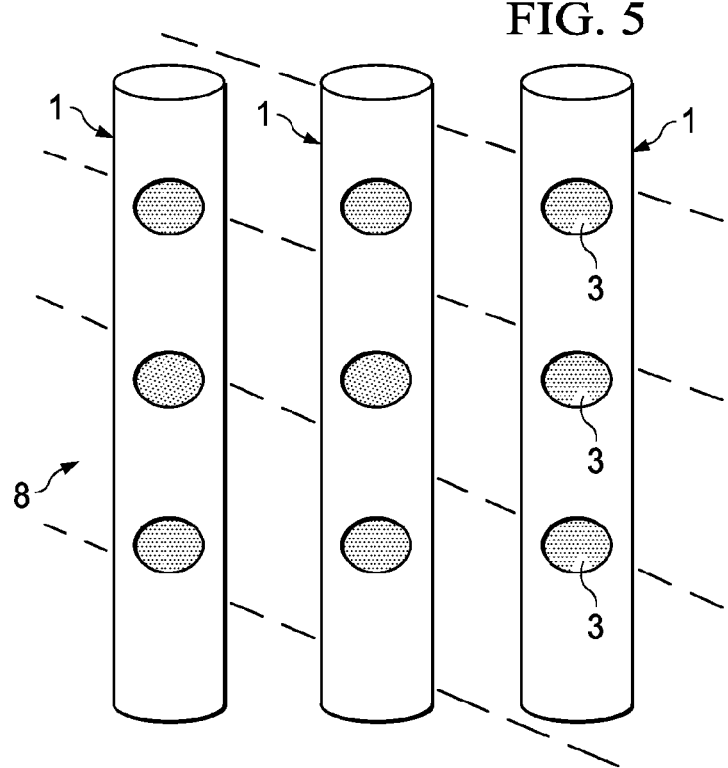
FIG. 5 is a singular adhesive patch attached with several drug delivery tubes for combination therapy.

FIG. 2 shows a cross-sectional view of one embodiment of the therapeutic agent delivery device during administration of the agent. The device 1 comprises a hollow cylindrical tube 2 and is filled with a diagnostic, therapeutic, or prophylactic agent 4 while being placed against an anatomical site 5. The device is positioned to release the agent is directly to the targeted anatomical site in an unidirectional manner through the passageways 3 (see arrows). FIG. 3 shows one embodiment of a carrier 6 to which a therapeutic agent delivery device may be attached. FIG. 4 shows one embodiment depicting five (5) therapeutic agent delivery devices 1, comprising three passageways 3 each, attached to a stent 7. FIG. 5 shows one embodiment depicting three (3) therapeutic agent delivery devices 1, comprising three (3) passageways 3 each, attached to an adhesive patch 8.

FIG. 6 shows exemplary data of zero order release kinetics of crystal violet (e.g., a dye, and anti-fungal agent) for twenty-eight (28) days from three embodiments of the therapeutic drug delivery device. Circles: A device with one surface passageway ($R^2=0.9945$). Squares: A device with two surface passageways ($R^2=0.9998$). Triangles: A device with three surface passageways ($R^2=0.9998$). FIG. 7 shows exemplary data of the percentage of crystal violet (dye, antifungal-agent) released at zero-order for twenty-eight (28) days from three different embodiments of the therapeutic drug delivery device. Circles: A device with one surface passageway ($R^2=0.9945$). Squares: A device with two surface passageways ($R^2=0.9999$). Triangles: A device with three surface passageways ($R^2=0.9998$). FIG. 8 shows exemplary data demonstrating the linearity of cumulative agent release between the three embodiments tested in FIGS. 6 and 7 after twenty-eight (28) days ($R^2=0.9962$). Circle: A device with one surface passageway. Square: A device with two surface passageways. Triangles: A device with three surface passageways. FIG. 9 shows exemplary data of zero order release kinetics of crystal violet for five (5) days from one embodiment of the therapeutic agent delivery device, wherein there are no holes on the device surface, but has a single outlet port on one end of the device ($R^2=0.9993$).

Figure 10:
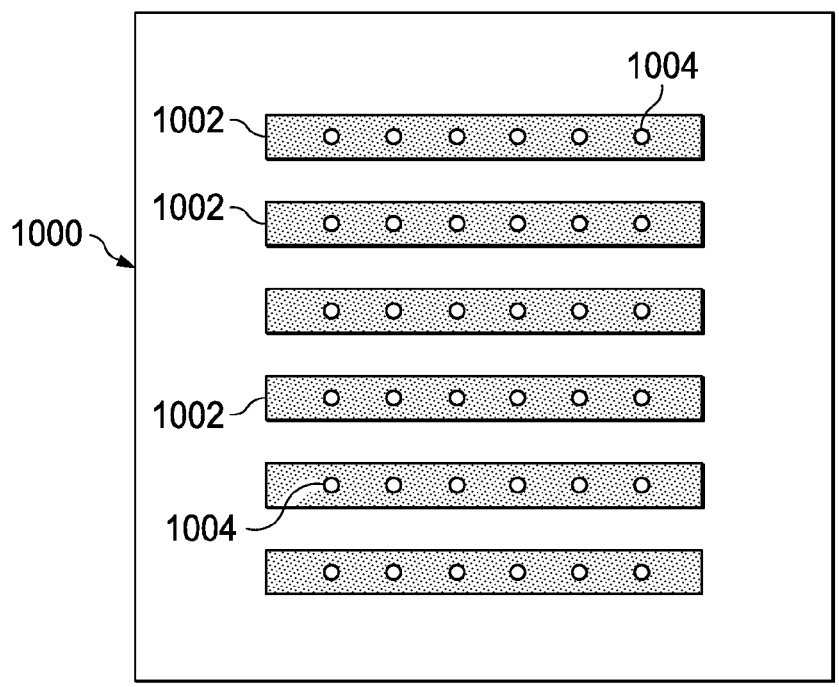
FIG. 10 is a schematic of a mold showing the trenches and the through holes.

In one embodiment, the process of forming micro-holes requires first the fabrication of a mold consisting of a planar substrate with trenches and through holes located in trenches as illustrated in FIG. 10. The trenches can hold the miniature substrates, such as polymer tubes. Then the whole assembly can be flipped over and then etched from the backside to produce through holes in the targets such as the wall of a biodegradable tube. In this way, the planar substrate works as a mold. The mold can be made from a variety of materials, including a silicon wafer, a glass substrate, and a metal plate. The etching technique can be chosen from a number of techniques including but not limited to physical etching, chemical etching, reactive ion etching, laser ablation, and cutting by plasma torches.

FIG. 10 shows a schematic drawing of a mold 1000 with trenches 1002 and through holes 1004. Although the through holes 1004 shown in the figure are circular, they can be formed in other shapes as desired.

Figure 11A:
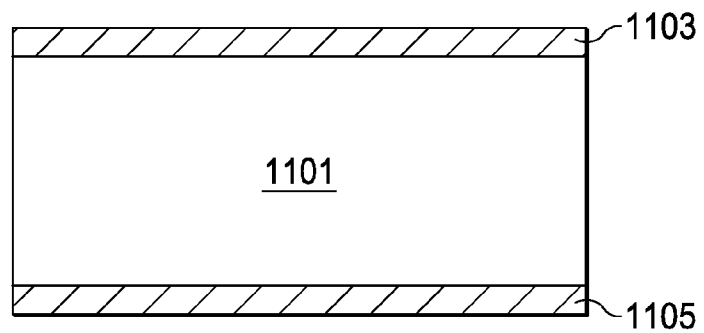
FIGS. 11A-11D shows a process flow chart for fabricating a silicon mold.
Figure 11B:
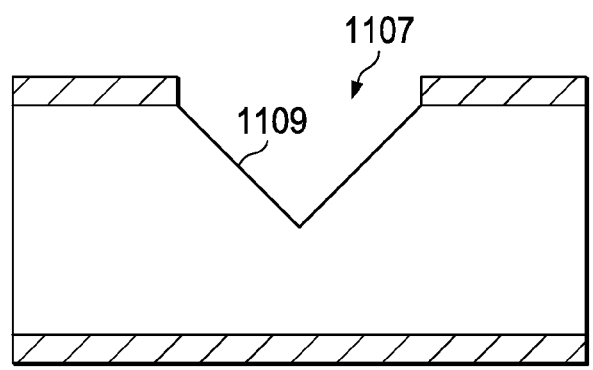
Figure 11C:
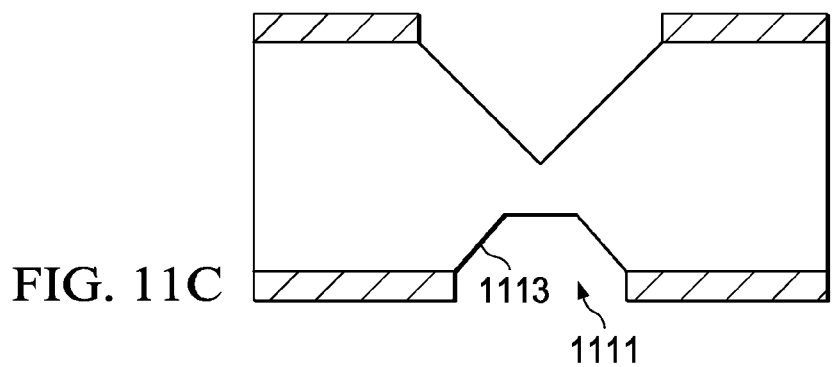
Figure 11D:
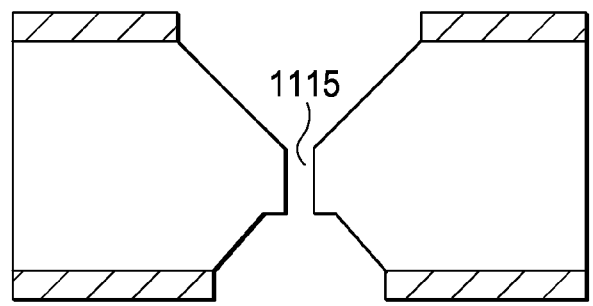

In one embodiment, the mold can be fabricated on a silicon wafer using micro-fabrication technology. An example of the process flow is shown in FIG. 11A-11D where all figures are shown in a cross-sectional view. To start, the silicon mold can be fabricated on a double side polished wafer 1101. The fabrication process begins with a deposition of masking layers 1103 and 1105 on the topside and the backside of the wafer respectively, as shown in FIG. 11A. Low stress silicon nitride formed by low pressure chemical vapor deposition (LPCVD) is a preferred material for masking layer 202 and 203. In FIG. 11B, a photolithography step is applied to define an opening on the topside which is further transferred through the silicon nitride layer by reactive ion etching (RIE). Alignment marks are fabricated in this step but not shown in the figure. Then a wet anisotropic etching using TMAH is applied to etch a trench 1107 in the silicon wafer with a silicon nitride layer as an etching mask. The trench sidewalls 1109 are smooth planes which work as etch stop layers. The V-groove trench 1107 will be used to hold the tubes. After that, the second photolithography step is applied to the backside of wafer to define a window pattern which is aligned to the trench on the topside with the help of alignment marks. RIE and wet anisotropic etching are used again to transfer the window 1111 pattern into the silicon wafer and expose the smooth planes 1113 as shown in FIG. 11C. In FIG. 11D, the third lithography step is applied to define the hole structure which is then etched into a through hole 1115 by RIE. An optional step to harden the mold surface is to apply a silicon nitride layer on the surface, which is not shown in the figure.

In one embodiment, the method comprises preparing a trench structure on a planar substrate, such as a silicon wafer 10 (FIG. 12A). In one embodiment, a trench structure on the silicon wafer was fabricated by a combination of photolithography and anisotropic etching wherein a silicon dioxide layer 20 was deposited on a silicon wafer 10, followed by the deposition of a chromium layer 30 by physical vapor deposition (FIG. 12B). The silicon dioxide 20 and chromium 30 layers serve as etching mask layers for the subsequent process steps. The silicon wafer can be either a (110, FIG. 12E) or a (100, FIG. 12F) wafer, depending on the choice of "U" shaped or "V" shaped trenches to be fabricated by wet anisotropic etching. After spin-coating of a photo-resist 40 layer, a trench structure 50 was created by photolithography on the photo-resist layer 40 as shown in FIG. 12C. The trench direction is aligned to the wafer flat. Alignment marks 140 were also created in this step. See, FIG. 11A. The alignment marks were designed to position future patterns, e.g., micro-holes, to the desired places of non-planar substrates, such as polymer tubes, which would placed into trenches on the silicon wafer. The trench structure was then transferred through the chromium layer to the silicon oxide layer by reactive ion etching (FIG. 12D). This was followed by a second reactive ion etching step transferring the trench structure through the oxide layer to the silicon substrate using the chromium layer as the etching mask. This step produced the trench structures 60. The final step to fabricate the trench structure was a wet anisotropic etching step, which was used to remove the unwanted silicon materials. The processing sequence as described produced a "U" shaped trench 70 in a (110) wafer, or a "V" shaped trench 80 in a (100) wafer as shown in FIGS. 12E and 12F, respectively. The depth and width of the trench structures can be controlled by the geometry of the photomask and the anisotropic etching time. The depth and width of trenches should be slightly larger than the dimension of the non-planar substrate. The structures with the U shape or the V shape trench can also be used as to form a mold. An example of a V shape trench is shown in FIG. 11B.

Figure 13A:
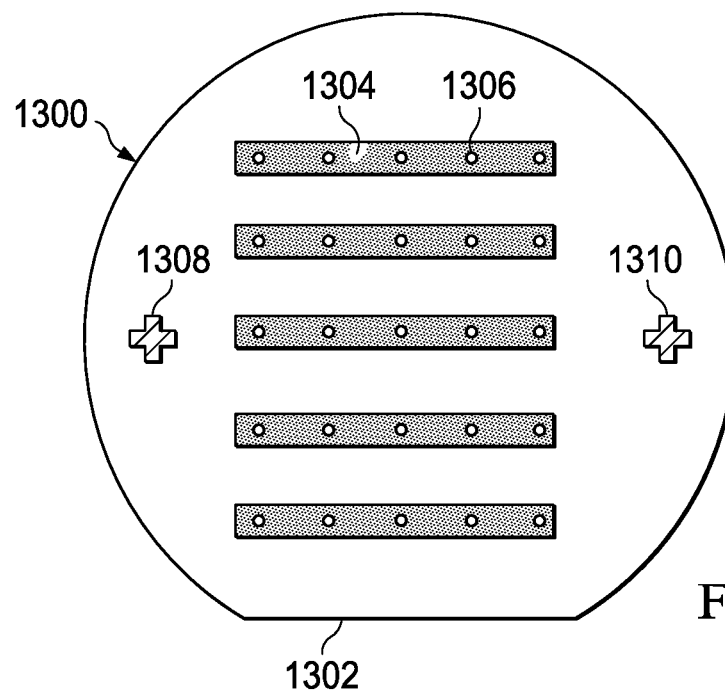
FIGS. 13A-13C shows a plain view of a silicon mold fabricated using the process shown in FIG. 11.
Figure 13B:
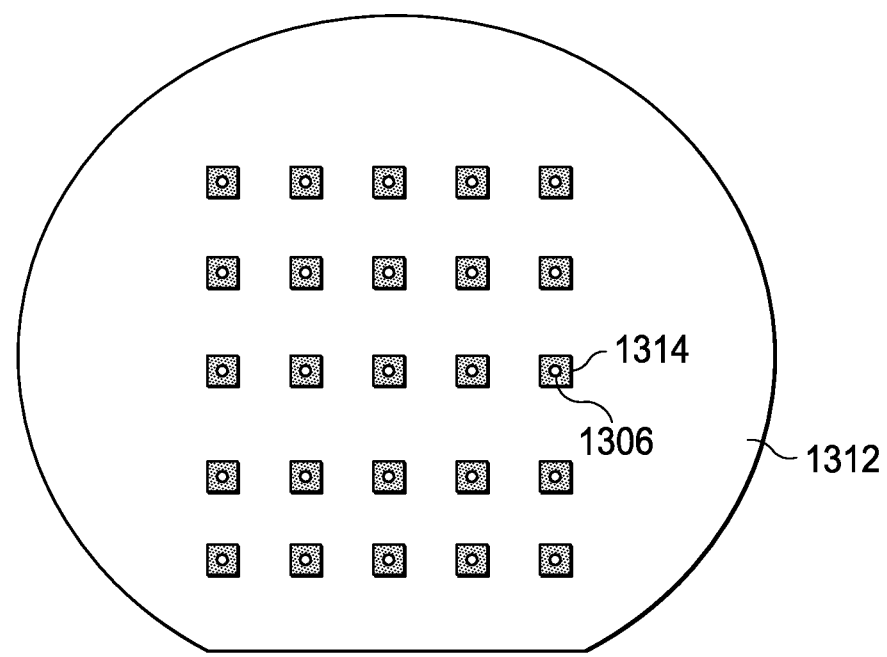
Figure 13C:
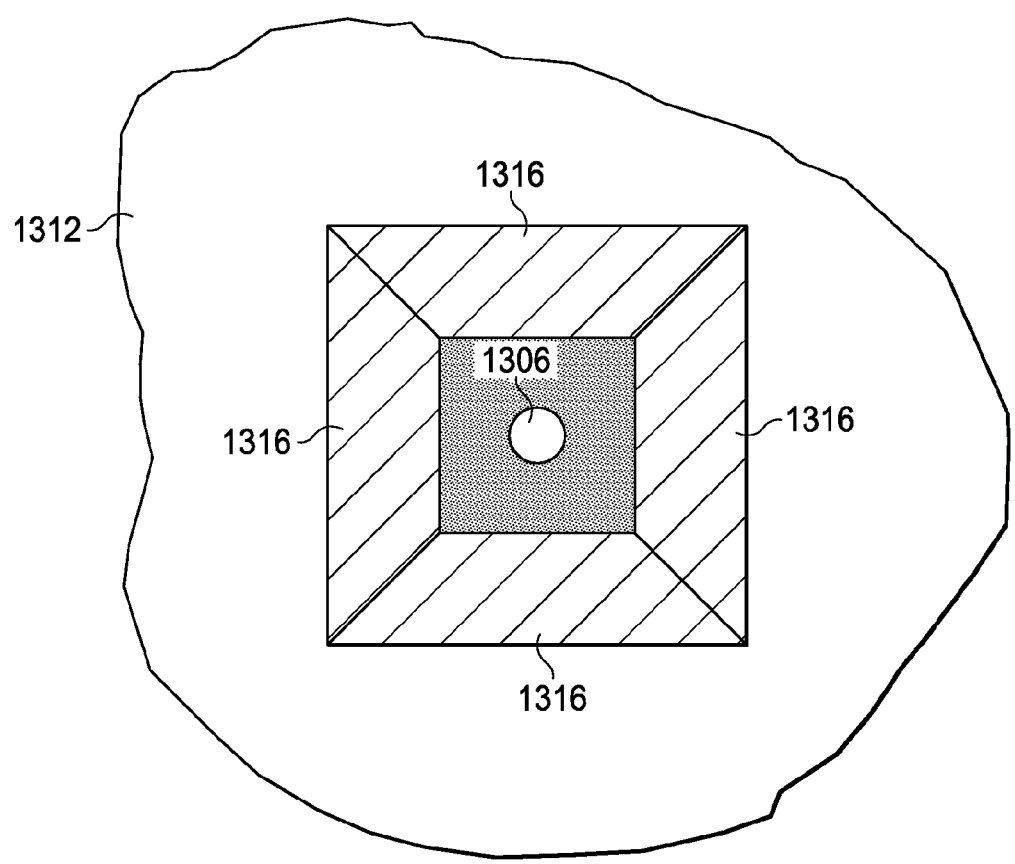

FIGS. 13A-13C shows the plan view of the schematic silicon mold fabricated following the process shown in FIGS. 11A-11D. FIG. 13A is the topside 1300 of the wafer with wafer flat 1302. As shown, the design looks similar to that in FIG. 10 with trenches 1304 and through holes 1306. Two alignment marks 1308 and 1310 are fabricated in this step as shown in FIG. 11A. FIG. 13B shows the backside 1312 of the wafer. Window structures 1314 and through holes 1306 are aligned with the trenches 1304 on the topside. The window structures 1314 correspond to 1111 in FIG. 11C. FIG. 13C shows an enlarged view of a single window structure 1312 in FIG. 13B. Four planes 1316 here correspond to 1113 in FIG. 11C and the through holes 1306 in FIGS. 13A-13C correspond to the hole 1115 in FIG. 11D.

Figure 13D:
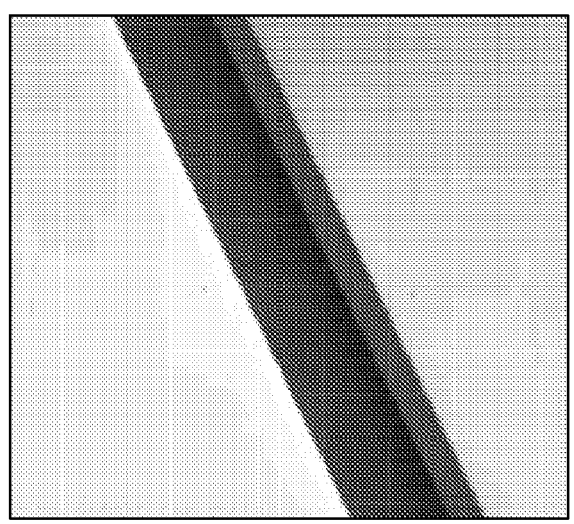

FIG. 13D shows a scanning electron microscopy image of a "U" shaped trench fabricated on a silicon wafer. The width and depth of the trench is about 100 microns and 80 microns, respectively.

After the mold is fabricated, the fabrication of micro-holes in the tubes is rather simple. As shown in FIG. 14A, first the tubes 1402 are inserted into the trenches on the topside of the mold. Adhesives may or may not be applied to part of the trenches to hold the tubes in the trenches. Another substrate 1404 may also be used to push tubes toward the bottom of the trenches. Then the whole assembly is flipped over so that the backside of the mold is facing up as shown in FIG. 14B. An etching step is performed to transfer the through hole patterns of the mold to the tubes and finally holes 1408 on tubes are obtained. In one embodiment, reactive ion etching is used as indicated by the reactive plasma 1406.

The planar substrate can be any material other than a silicon wafer, depending on the structure and the application of interest. Accordingly, the process steps will have to be adjusted. Other trench structures with other shapes can be fabricated if desired, depending on the shape of the non-planar substrates.

In one embodiment, the fabrication of passageways, such as micro-holes, on a non-planar substrate starts with inserting the non-planar substrate into the trench structure of the supporting substrates. In one embodiment, an adhesive is applied in the trench to hold the non-planar substrate in place. In one embodiment, the adhesive is a photo-resist. The assembly of the supporting substrate with the non-planar substrate is then handled as a conventional subject with a planar substrate for subsequent process steps.

In one embodiment, the non-planar substrate is a polymer tube 90 shown in FIGS. 15A-15E. In one embodiment, it was inserted into a "U" shaped trench as shown in FIG. 15A. In one embodiment, a masking layer 100 was deposited on the wafer as well as the surface of the polymer tube 90, as shown in FIG. 15B. In one embodiment, the masking layer 100 is a chromium layer. The alignment marks were protected during the chromium deposition. This was followed with spin-coating of a photo-resist layer 110 on top of the polymer tube as shown in FIG. 15C. After careful alignment, micro-holes 120 were fabricated following a sequence of steps: first, defining the micro-holes using photolithography with a photo-resist layer 110. Then the micro-hole structures were transferred through the chromium layer 100 by reactive ion etching. Finally, a second reactive ion etching step was applied to transfer the micro-hole structure through the tube wall to yield fully penetrated micro-holes 130 on the tube. FIG. 13D shows an optical microscopy image of a polyimide tube with a hole of about 20 microns in diameter fabricated by this method.

Figure 16:
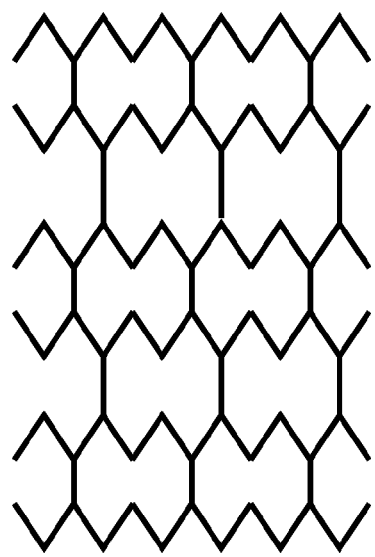
FIG. 16 is a stent structure whose struts can be built using the perforated drug delivery device.
Figure 17:
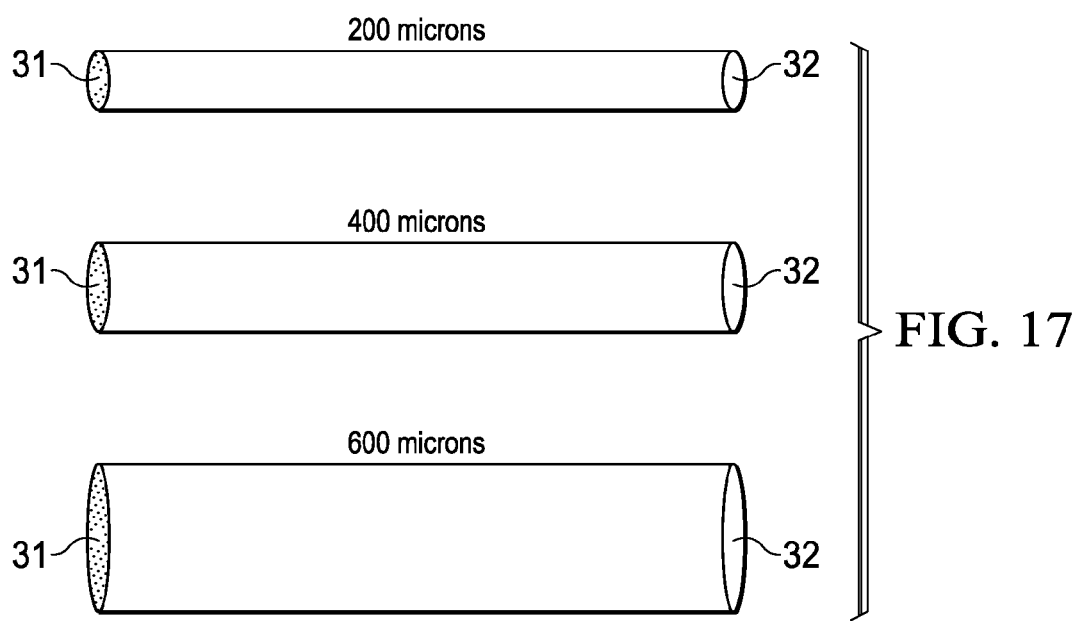
FIG. 17 is drug delivery device in different sizes with no perforations and only one end open for drug release.

FIG. 16 illustrates a schematic of one embodiment of a carrier comprising a skeleton of a bare metal stent. FIG. 17 shows one another embodiment of a therapeutic agent delivery device with different diameters that is 200 microns, 400 microns, and 600 microns. The device comprises of one outlet port 32 without any passageways on the surface of the device. One end of the device 31 is sealed with a heat shrink tube or a biocompatible adhesive. Upper drawing: A device with inside diameter of 200 microns. Middle drawing: A device with inside diameter of 400 microns. Middle drawing: A device with inside diameter of 600 microns.

Figure 18:
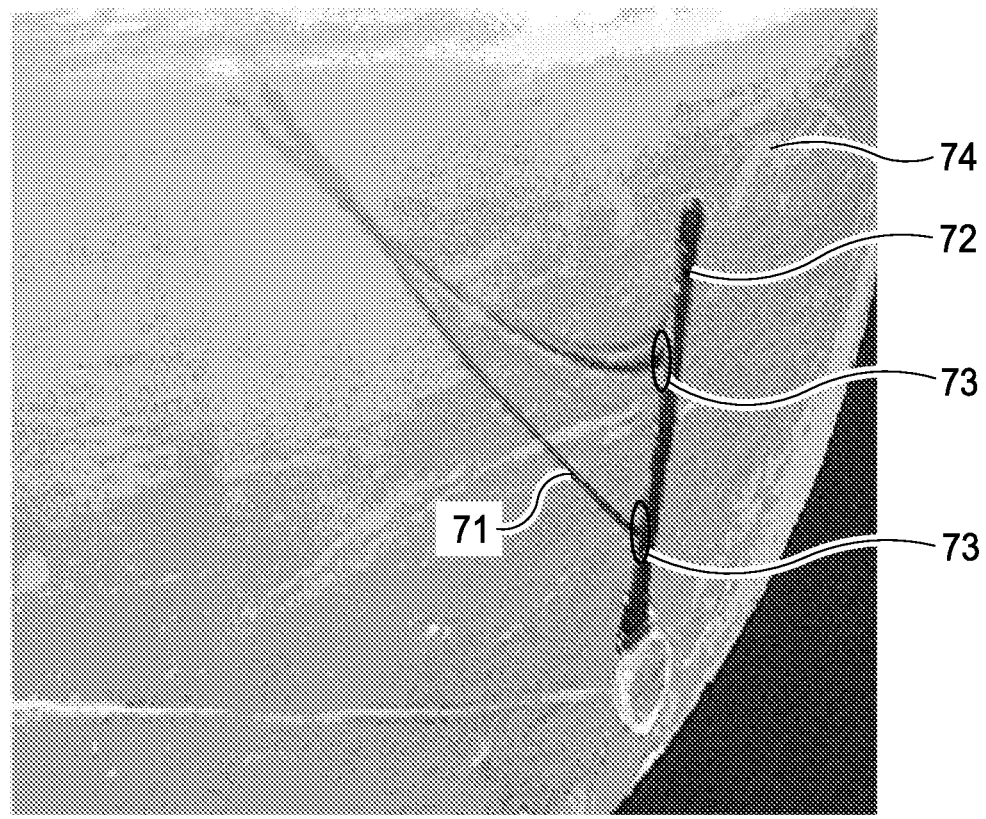
FIG. 18 is a photograph of drug release via the perforations on the drug delivery device into the dissolution medium.
Figure 19:
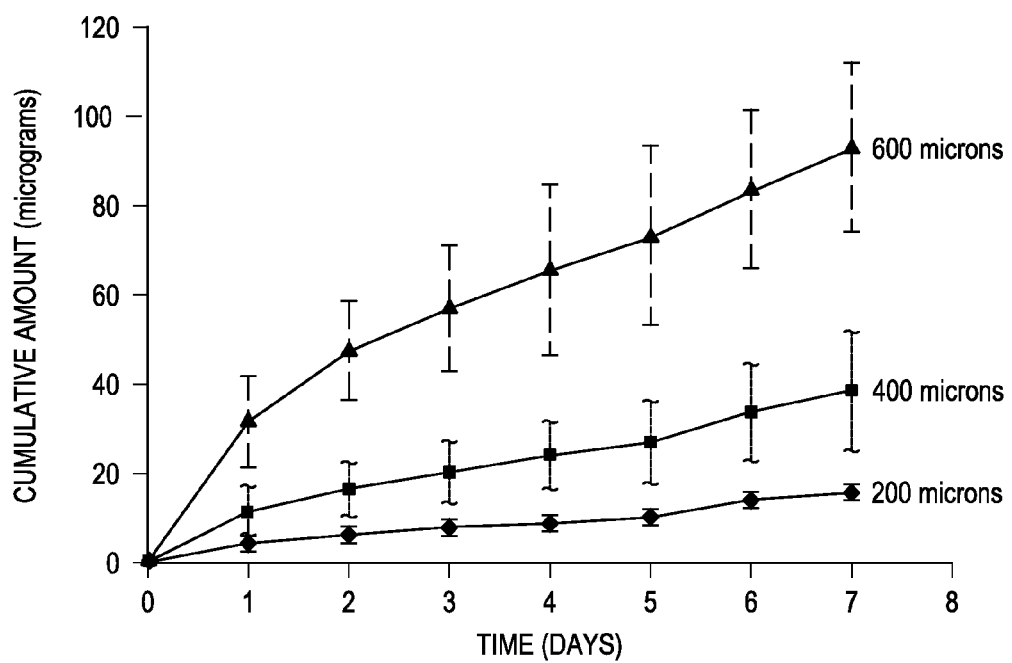
FIG. 19 is a graph illustrating cumulative zero order release of crystal violet from three types of drug delivery device of FIG. 17.
Figure 20:
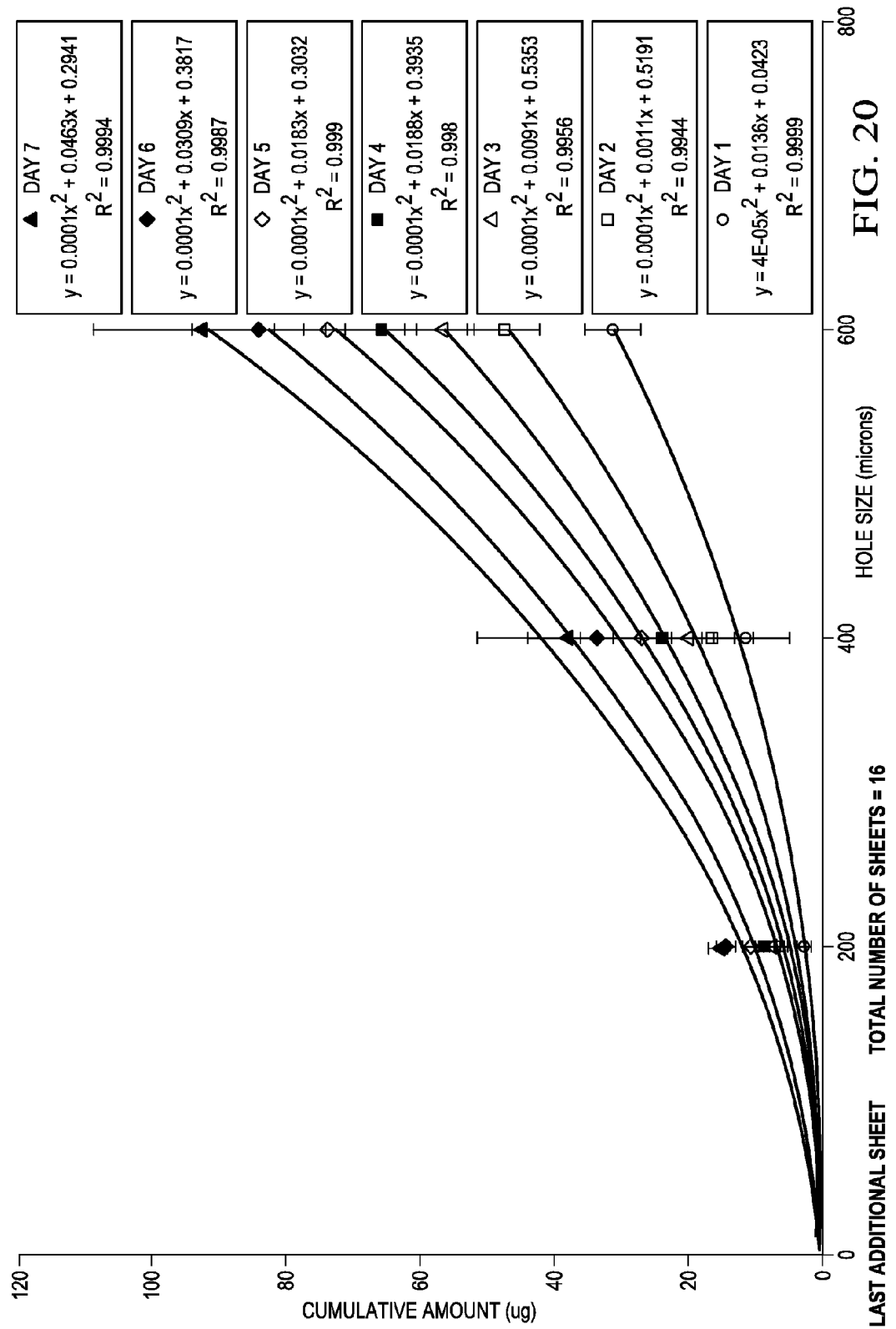
FIG. 20 is a graph comparing the daily drug release from the drug delivery devices of FIG. 17.

FIG. 18 presents an exemplary photomicrograph showing release of crystal violet 71 from a device 72 comprising two passageways 73 into a phosphate buffered saline solution 74. Release of drug from each hole is independent of the other. The dimension of the tube is 1000 microns and the holes size is approximately 400 microns. These bigger sized tubes and holes were selected to visually observe the release mechanism, and are not intended to limit the present invention. FIG. 19 shows exemplary data of zero order release kinetics of crystal violet (e.g., a dye, and anti-fungal agent) for twenty-eight (28) days from three embodiments of the therapeutic drug delivery device. Circles: A device with one outlet port and inside diameter of 200 microns ($R^2$=0.9667). Squares: A device with one outlet port and inside diameter of 400 microns. Triangles: A device with one outlet port and inside diameter of 600 microns ($R^2$=0.9355). FIG. 20 shows exemplary data comparing cumulative amount of crystal violet released from the three groups (200 microns, 400 microns, and 600 microns) for seven days. The release rates follow a quadratic relationship as is evident by the equations of line for each day, which are in the form: $y=a.x^2+bx+c$, and their corresponding $R^2$ values which are close to 1.000. Hence, the rate of release of drug is also proportional to the square of the radius, that is, $$\frac{dM}{dT} \alpha r^2.$$

V. Therapeutic Applications: In one embodiment, the present invention contemplates methods for treating medical conditions and diseases. For example, such conditions may include, but are not limited to, cardiovascular disease, cancer, diabetes, pain, Parkinson's disease, epilepsy, or ocular diseases.

A. Cardiovascular Diseases: In one embodiment, the present invention contemplates a method for treating a cardiovascular disease. In one embodiment, the cardiovascular disease may include, but not limited to, stenosis, restenosis, stroke, myocardial infarction, congestive heart disease, high blood pressure, angina, atherosclerosis, or thrombosis. In many cases, cardiovascular diseases are treated with drug eluting stents (DES). While easily inserted into specific cardiovascular vessels these DESs have encountered significant biocompatibility problems.

1. Clinical Problems Associated with Drug Eluting Stents: Since their inception, DESs have significantly reduced the rate of clinical restenosis as compared to bare metal stents (BMS) and conventional balloon angioplasty. Moses et al., "*Sirolimus-Eluting Stents Versus Standard Stents in Patients with Stenosis in a Native Coronary Artery*" N Engl Med 349:1315-1323 (2003); and Park et al., "*A Paclitaxel-Eluting Stent for the Prevention of Coronary Restenosis*" N Engl Med 348:1537-1545 (2003). An ideal drug eluting stent has been suggested to possess characteristics including, but not limited to: i) polymers allowing ideal drug release; ii) drugs should inhibit vascular smooth cell proliferation and inflammation and prevent restenosis; iii) the stent becomes part of the vasculature to prevent any late inflammations/thrombosis; iv) the stent allows collateral blood vessel circulation. Baffour et al., "*Enhanced Angiogenesis and Growth of Collaterals by In Vivo Administration of Recombinant Basic Fibroblast Growth Factor in Rabbit Model of Acute Lower Limb Ischemia: Dose-Response Effect of Basin Fibroblast Growth Factor*" Vasc Surg 16:181-191 (1992); and Geerts A M, "*Colic I. Angiogenesis in Portal Hypertension: Involvement* in Increased Splenehnic Blood Flow and Collaterals?" *Acta Clin Belg* 62:271-275 (2007). However, even before introduction of the first commercial DES, potential problems were identified that may arise due to "nonerodable thick polymer sleeve, very high concentration of the active drug, extended release kinetics, loose stent architecture, and inhomogeneous drug delivery". Virmani et al., "*Mechanism of Late In-Stent Restenosis After Implantation of Paclitaxel Derivate-Eluting Polymer Stent System in Humans*" *Circulation* 106:2649-2651 (2002).

Studies have shown an increase in the rate of death and myocardial infarction in patients following 18 months to 3 years after stenting with CYPHER® and TAXUS®. Aziz et al., "*Late Stent Thrombosis Associated with Corona Aneurysm Formation After Sirolimus-Eluting Stent Implantation*" *Invasive Cardiol* 19:E96-8 (2007); Camenzind E., "*Treatment of In-Stent Restenosis—Back to the Future?*" *N Engl Med* 355:2149-2151 (2006); Camenzind et al., "*Stent Thrombosis Late After Implantation of First-Generation Drug-Eluting Stents: A Cause for Concern*" *Circulation* 15:1440-1455 (2007); and Pfisterer M. E., "*The BASKET-LATE-Study. Basel Stent Cost-Effectiveness Trial—Late Thrombotic Events Trial*" *Herz* 31:259 (2006). A statement issued by United States Food and Drug Administration also identified adverse cardiac events in patients treated with drug during stents. fda.gov/cdrlVnewslOgl406 (2007).

The reported problems are usually associated with late stent thrombosis (LST) which blocks the arteries increases the risk of myocardial infarction. Interestingly, it has been reported that bare metal stents (BMS) have lower MACE rates as compared to DES. Kim et al., "*Stent-Related Cardiac Events After Non-Cardiac Surgery: Drug-Eluting Stent Bare Metal Stent*" *Int J Cardiol* 123:353-354 (2008); Lagerqvist et al., "*Long-Term Outcomes with Drug-Eluting Stents Versus Bare-Metal Stents in Sweden*" *N Engl Med* 356:1009-1019 (2007); and Steinberg et al., "*Drug-Eluting Stent Thrombosis Bare Metal Stent Restenosis: Finding the Lesser of Two Evils*" *Am Heart Hosp* 5:151-154 (2007). However, the exact nature of drug-eluting stent thrombosis is still unclear, for example, what causes it, how often it occurs, under what circumstances it occurs, or what the risk of occurrence is in a given patient.

2. Late Stent Thrombosis (LST): Polymer coatings have been named as one factor associated with the failure of DES. Under mechanical stress such as during implantation of stents, polymer coatings might crack leading to injury to arterial wall. Injury activates platelet aggregation and blood clotting leading to LST. Generally, it takes 28 days for the bare metal stent to become part of the vasculature (endothelialization). Cracking of polymers may also lead to drug dumping at the injured arterial site delaying the healing of the stent. The incomplete endothelialized stent becomes an attractive site for platelet adhesion increasing the probability of LST. The drug overexposure also prevents collateral blood vessel formation, thereby increasing the stress on the heart. Alternatively, polymer hypersensitivity might incite inflammation reactions. The occurrence of such allergic reactions has supportive evidence such as a marked activation of inflammatory cells (i.e., for example, leukocytes) at the site of a stent. Li et al., "*Is Inflammation Contributor for Coronary Stent Restenosis?*" *Med Hypotheses* 68:945-951 (2007). Leukocytes have also been linked to the formation of neointimal hyperplasia along with platelet adhesion indicating the central role of inflammation in both restenosis and LST. Golino et al., "*Inhibition of Leukocyte and Platelet Adhesion Reduces Neointimal Hyperplasia After Arterial Injury*" *Thromb Haemost* 77:783-788 (1997); Sainani et al., "*The Endothelial Leukocyte Adhesion Molecule. Role in Coronary Artery Disease*" *Aeta Cardiol* 60:501-507 (2005; Wang et al., "*Enhanced Leukocyte Adhesion to Interleukin-I Beta Stimulated Vascular Smooth Muscle Cells is Mainly Through Intercellular Adhesion Molecule-1*" *Cardiovasc Res* 28:1808-1814 (1994).

3. Restenosis: Restenosis is believed to result from mechanisms including, but not limited to, inflammation or cell proliferation at the site of injury in the stented artery. Drugs such as paclitaxel and sirolimus are being currently used in drug eluting stents to prevent scar tissue growth and neointima formation. In general, these drugs were chosen for potency, and general effects on suppressing cellular growth without targeting the underlying vascular disease.

Restenosis is believed to result from injury to an arterial wall during stent implantation and occurs within 6-12 months of the procedure. In contrast, LST mainly occurs when the stent is not able to endothelialize and usually occurs after 12 months of stenting. Classic restenosis occurring with bare metal stents (i.e., for example, non-drug coated) comprises progressive, instead of rapid, symptoms and affects 25-30% of the treated patients. In contrast, LST is believed to result of sudden formation of a blood clot within the stent. Though LST is observed in only 1.5-5% of the patients but morbidity and mortality rates are quite high, making it more dangerous. Holmes D R, Jr., "*Incidence of Late Stent Thrombosis with Bare-Metal, Sirolimus, and Paclitaxel Stents*" *Rev Cardiovasc Med* 8 (Suppl 1): S11-18 (2007).

A. Anti-Restenosis Drugs: Zotarolimus (formerly known as ABT-578) is a sirolimus analogue having cytostatic properties. Buellesfeld et al., ABT-578-eluting stents. "*The Promising Successor of Sirolimus- and Paclitaxel-Eluting Stent Concepts?*" *Herz* 29167-29170 (2004). Zotarolimus may be synthesized by substituting the native hydroxyl group with the tetrazole ring at position 40 in rapamycin. It is believed extremely lipophilic and a very low water solubility, hence very little is released to the circulation.. Seabra-Gomes R., "*Percutaneous Coronary Interventions with Drug Eluting Stents for Diabetic Patients*" *Heart* 2006; 92:410-419 (2006). Everolimus is synthesized from sirolimus by substituting a —$CH_2OH$ group at position 40. Like sirolimus, everolimus also inhibits mammalian target of rapamycin (mTOR). Experimental studies have shown that oral everolimus also inhibits smooth muscle cell proliferation and prevents neointimal thickening and arteriosclerosis. Farb et al., "*Oral Everolimus Inhibits In-Stent Neointimal Growth*" *Circulation* 106:2379-2384 (2002); Waksman et al., "*Optimal Dosing and Duration of Oral Everolimus to Inhibit In-Stent Neointimal Growth in Rabbit Iliac Arteries*" *Cardio-vasc Revasc Med* 7:179-184 (2006). Everolimus has been reported to have a better pharmacokinetic profile and bioavailability compared with sirolimus. Patel et al., "*Everolimus: Immunosuppressive Agent in Transplantation*" *Expert Opin Pharmacother* 7:1347-1355 (2006). Everolimus has also been reported to absorb into tissues more rapidly than sirolimus and may have a longer cellular residence time and activity. Grube et al., "*Everolimus for Stent-Based Intracoronary Applications*" *Rev Cardiovasc Med* 5 (Suppl 2):S3-S8 (2004).

Biolimus A9 (Biosensors International, Singapore) is reported as a highly lipophilic sirolimus analog. Biolimus has been reported as well tolerated and effective having similar immunosuppressive potency as sirolimus. However, it appears that Biolimus A9 is more rapidly absorbed than sirolimus by the vessel wall and enters smooth muscle cell membranes more readily, thereby causing cell cycle arrest at $G_0$. Costa et al., "*Angiographic Results of the First Human*

Experience with the Biolimus A9 Drug-Eluting Stent for De Coronary Lesions" Am Cardiol 98:443-446 (2006). Recently release data indicates that Biolimus A9 showed significantly less neointimal formation as compared with paclitaxel. Chevalier B., "NOBORI 1: Part A Prospective, Randomized Trial of Biolimus A9 and Paclitaxel-Eluting Stents: 9-Month Clinical and Angiographic Follow-Up" Transcatheter Cardiovascular Therapeutics Symposium (2006).

Tacrolimus (also FK-506, Fujimycin, Prograf) is a hydrophobic macrolide immunosuppressant produced by Streptomyces tsukubaensis. Goto et al., "Discovery of FK-506, Novel Immunosuppressant Isolated from Streptomyces Tsukubaensis" Transplant Proc 19:4-8 (1987). Tacrolimus is widely used to prevent allograft rejection after organ transplantation. Although it is not necessary to understand the mechanism of an invention, it is believed that tacrolimus is a noncytotoxic T cell inhibitor, which causes cell apoptosis following growth arrest in the $G_0$ phase of the cell cycle. Gottschalk et al., "Apoptosis in B Lymphocytes: the WEHI-231 Perspective" Immunol Cell Biol 73:8-16 (1995). A protein-engineered nanoparticle albumin bound paclitaxel (nab-paclitaxel) is commercially available and may be useful for the treatment of coronary and peripheral artery restenosis (Coroxane®, Abraxis Bioscience, Inc.). Coroxane®, like its oncology counterpart Abraxane®, is a protein stabilized emulsion that is believed to enhance the solubility of water insoluble paclitaxel. The albumin formulation may also reduce toxicities associated with a solubility enhancing excipient, Cremophor EL®. Green et al., "Abraxane, Novel Cremophor-Free, Albumin-Bound Particle Form of Paclitaxel for the Treatment of Advanced Non-Small Cell Lung Cancer" Ann Oncol 17:1263-1268 (2006). As a result, the solubility of paclitaxel is improved and the non-drug related toxicities are eliminated. A Phase II clinical study tested twenty three (23) patients randomized to one of four doses (10, 30, 70, or 100 mg/m$^2$), wherein doses between approximately 10-30 mg/m$^2$ were found to be safe and effective. Margolis et al., "Systemic Nanoparticle Paclitaxel (Nab-Paclitaxel) for In-Stent Restenosis (SNAPIST-I): First-In-Human Safety and Dose Finding Study" Clin Cardiol 30:165-170 (2007).

Docetaxel is commercially available (Taxotere®, Sanofi-Aventis) and approved as an anti-mitotic drug used for the treatment of breast, ovarian and non-small cell lung cancer. Clarke et al., "Clinical Pharmacokinetics of Docetaxel" Clin Pharmacokinet 36:99-114 (1999). Docetaxel is a semi-synthetic analogue of paclitaxel and differs from paclitaxel at two positions in its chemical structure. For example, docetaxel has a hydroxyl functional group on carbon 10, whereas paclitaxel has an acetate ester and a tert-butyl substitution exists on the phenylpropionate side chain. The carbon 10 functional group change causes docetaxel to be more lipid soluble than paclitaxel. Docetaxel is believed to be a microtubule polymerizing agent, and may have improved antiproliferative properties as compared to paclitaxel. Yasuda et al., "Local Delivery of Low-Dose Docetaxel, Novel Microtubule Polymerizing Agent, Reduces Neointimal Hyperplasia in Balloon Injured Rabbit Iliac Artery Model" Cardiovasc Res 53:481-486 (2002). Docetaxel, however, has been associated with cytotoxicity, which has been reported to occur in a dose-dependant manner. Silvestrini et al., "In Vitro Cytotoxic Activity of Taxol and Taxotere on Primary Cultures and Established Cell Lines of Human Ovarian Cancer" Stem Cells 11:528-535 (1993). Docetaxel has the potential as a therapeutic for preventing restenosis, but more improvement is needed for better safety and efficacy.

Curcumin (diferuloylrnethane) is believed to be a polyphenolic yellow pigment found in the Indian spice, tumeric (a powdered rhizome of Curcurna longa Linn). Huang et al., "Inhibitory Effects of Dietary Curcumin for Stomach, Duodenal, and Colon Carcinogenesis in Mice" Cancer Res 54:5841-5847 (1994). Curcumin is believed to exhibit various biological activities including, but not limited to, anti-proliferative activity, anti-inflammatory, antioxidant activity, wound healing ability, and anti-microbial activity. Dorai et al., "Role of Chemopreventive Agents in Cancer Therapy" Cancer Lett 215:129-140 (2004); Gupta et al., "Dietary Antioxidant Curcumin Inhibits Microtubule Assembly Through Tubulin Binding." FEBS J 273:5320-5332 (2006); and Ruby et al., "Antitumour and Antioxidant Activity of Natural Curcuminoids" Cancer Lett 94:79-83 (1995). Although it is not necessary to understand the mechanism of an invention, it is believed that at least two mechanisms contribute to restenosis including, but not limited to, proliferation of vascular smooth muscle cells and inflammation at the site of injury. It is further believed that inflammation reactions may be initiated by a build-up of reactive oxygen species (i.e., for example, ROS, or free radicals) at an arterial site. Like paclitaxel, curcumin inhibits cell proliferation by stabilizing microtubule assembly through tubulin binding. In addition, curcumin may reduce nitric oxide (NO) levels thereby acting as a suitable antioxidant. Ukil et al., "Dos Curcumin, the Major Component of Food Flavour Turmeric, Reduces Mucosal Injury in Trinitrobenzene Sulphonic Acid-Induced Colitis" Br Pharmacol 139 (2): 209-218 (2003). The natural healing powers of curcumin make it an excellent candidate for treatment and prevention of restenosis.

Resveratrol (trans-3,4,5-trihydroxystilbene).is believed to be a phytoalexin found in grapes and other medicinal plants that protects them against fungal infections. Docherty et al., "Resveratrol Selectively Inhibits Neisseria Gonorrhoea and Neisseria Meningitidis" Antimicrob Chemother 47:243-244 (2001). Resveratrol has been suggested as a possible answer for the observed 'French paradox'. The 'French paradox' refers to the observation that a high consumption of red wine is associated with relatively low incidences of coronary heart diseases. Kopp P., "Resveratrol, Phytoestrogen Found in Red Wine: A Possible Explanation for the Conundrum of the 'French Paradox'?" Eur Endocrinol 138:619-620 (1998). Additionally, resveratrol is also a widely reported anti-fungal, anti-bacterial, anti-viral, anti-oxidant, and an anti-inflammatory agent. de la Lastra et al., "Resveratrol as Antioxidant and Prooxidant Agent: Mechanisms and Clinical Implications" Biochem Soc Trans 35:1156-1160 (2007); Docherty et al., "Resveratrol Inhibition of Herpes Simplex Vires Replication" Antiviral Res 43:145-155 (1999): Elmali et al., "Effects of Resveratrol in Inflammatory Arthritis" Inflammation 30:1-6 (2007); Kasdallah-Grissa et al., "Resveratrol, a Red Wine Polyphenol, Attenuates Ethanol-Induced Oxidative Stress in Rat Liver" Life Sci 80:1033-1039 (2007); and Rahman et al., "Regulation of Inflammation and Redox Signaling by Dietary Polyphenols" Biochem Pharmacol 72:1439-1452 (2006). Resveratrol is also believed to block human platelet aggregation and vascular smooth muscle cell proliferation inhibiting thrombosis and inducing apoptosis which suggests its potential use against restenosis. Mnjoyan et al., "Profound Negative Regulatory Effects by Resveratrol Vascular Smooth Muscle Cells: Role of p53-p21 (WAF1/CIP I) pathway" Biochem Biophys Res Commun 311:546-552 (2003); Olas et al., "Resveratrol, a Phenolic Antioxidant with Effects on Blood Platelet Functions" Platalets 16:251-260 (2005). Pace-Asciak et al., "The Red Wine Phenolics Trans-Resveratrol and Quercetin Block Platelet Aggregation and Eicosanoid Synthesis: Implications for Protection Against Coronary Heart Disease" Clin Chim Acta 235:207-219 (1995). Poussier et al., "*Resveratrol Inhibits Vascular Smooth Muscle Cell Proliferation and Induces Apoptosis*" *Vasc Surg* 42:1190-1197 (2005).

B. Diabetes: In one embodiment, the present invention contemplates a method for treating diabetes using an impermeable therapeutic agent delivery device. In one embodiment, the delivery device provides controlled release of the agent. In one embodiment, the agent comprises insulin. In one embodiment, the device further comprises a glucose sensor. In one embodiment, the glucose sensor readout is transmitted to a remote detector. In one embodiment, the device is implanted within a cardiovascular vessel. One advantage of this method is that a diabetic patient receiving treatment using a delivery device comprising a glucose sensor would not be required to perform routine tests for blood sugar levels.

Diabetes is a chronic (lifelong) disease marked by high levels of sugar in the blood. Insulin is a hormone produced by the pancreas to control blood sugar. Diabetes can be caused by too little insulin, resistance to insulin, or both. People with diabetes have high blood sugar. because: i) their pancreas does not make enough insulin and/or ii) their muscle, fat, and liver cells do not respond to insulin normally.

Type 1 diabetes is usually diagnosed in childhood. Many patients are diagnosed when they are older than age 20. In this disease, the body makes little or no insulin. Daily injections of insulin are needed. The exact cause is unknown. Genetics, viruses, and autoimmune problems may play a role. Type 2 diabetes is far more common than type 1. It makes up most of diabetes cases. It usually occurs in adulthood, but young people are increasingly being diagnosed with this disease. The pancreas does not make enough insulin to keep blood glucose levels normal, often because the body does not respond well to insulin. Many people with type 2 diabetes do not know they have it, although it is a serious condition. Type 2 diabetes is becoming more common due to increasing obesity and failure to exercise. Gestational diabetes is high blood glucose that develops at any time during pregnancy in a woman who does not have diabetes.

There are many risk factors for type 2 diabetes including, but not limited to, age over 45 years, family history, heart disease, high blood cholesterol level, obesity, or lack of exercise. Diabetic symptoms may include, but not be limited to, blurry vision, excessive thirst, fatigue, frequent urination, hunger, or unexplained weight loss Examination and testing for diabetes usually begins with a urine analysis to determine glucose and ketones levels. Diagnosing diabetes may be determined by comparing the following factors: i) fasting blood glucose level—diabetes is diagnosed if higher than 126 mg/dL on two occasions. Levels between 100 and 126 mg/dL are referred to as impaired fasting glucose or pre-diabetes. These levels are considered to be risk factors for type 2 diabetes and its complications, ii) oral glucose tolerance test—diabetes is diagnosed if glucose level is higher than 200 mg/dL after 2 hours. (This test is used more for type 2 diabetes.), iii) random (non-fasting) blood glucose level—diabetes is suspected if higher than 200 mg/dL and accompanied by the classic diabetes symptoms of increased thirst, urination, and fatigue. (This test must be confirmed with a fasting blood glucose test.).

C. Epilepsy: In one embodiment, the present invention contemplates a method for treating epilepsy using an impermeable therapeutic agent delivery device. In one embodiment, the delivery device provides controlled release of the agent. In one embodiment, the agent comprises an anticonvulsant, wherein the anticonvulsant suppresses brain cell firing rates. In one embodiment, the device is implanted within a localized area of the brain that is suspected of having localized cell damage.

Epilepsy is a brain disorder involving repeated seizures of any type. Seizure disorders affect about 0.5% of the population. Approximately 1.5-5.0% of the population may have a seizure in their lifetime. Epilepsy can affect people of any age. Seizures are episodes of disturbed brain function that cause changes in attention or behavior. They are caused by abnormal excited electrical signals in the brain. Sometimes seizures are related to a temporary condition, such as exposure to drugs, withdrawal from certain drugs, or abnormal levels of sodium or glucose in the blood. In such cases, repeated seizures may not recur once the underlying problem is corrected. In other cases, injury to the brain (for example, stroke or head injury) causes brain tissue to be abnormally excitable. In some people, an inherited abnormality affects nerve cells in the brain, which leads to seizures. Some seizures are idiopathic, which means the cause can not be identified. Such seizures usually begin between ages 5 and 20, but they can occur at any age. People with this condition have no other neurological problems, but often have a family history of seizures or epilepsy.

Disorders affecting the blood vessels, such as stroke and TIA, are the most common cause of seizures after age 60. Degenerative disorders such as senile dementia Alzheimer type can also lead to seizures.

Some of the more common causes of seizures include but are not limited to, developmental problems, metabolic abnormalities, brain injury, tumors and brain lesions (such as hematomas), or infections. The severity of symptoms can vary greatly, from simple staring spells to loss of consciousness and violent convulsions. For many patients, the event is the same thing over and over, while some people have many different types of seizures that cause different symptoms each time. The type of seizure a person has depends on a variety of many things, such as the part of the brain affected and the underlying cause of the seizure. An aura consisting of a strange sensation (such as tingling, smell, or emotional changes) occurs in some people prior to each seizure. Seizures may occur repeatedly without explanation. Risk factors include, but are not limited to, a family history of epilepsy, head injury, or other condition that causes damage to the brain.

Epileptic seizures may fall under one of several classifications including, generalized seizures (i.e., for example, petit mal and grand mal), partial seizures (i.e., for example, simple and complex).

The diagnosis of epilepsy and seizure disorders requires a history of recurrent seizures of any type. A physical examination (including a detailed neuromuscular examination) may be normal, or it may show abnormal brain function related to specific areas of the brain. For example, an electroencephalograph (EEG), a reading of the electrical activity in the brain, may confirm the presence of various types of seizures. It may, in some cases, indicate the location of the lesion causing the seizure. EEGs can often be normal in between seizures, so it may be necessary to do prolonged EEG monitoring. Other tests may include various blood tests to rule out other temporary and reversible causes of seizures, including, but not limited to, a complete blood count, blood chemistry, blood glucose, liver function, kidney function, infectious diseases, or cerebrospinal fluid analysis.

Anti-convulsant oral drugs are normally prescribed to control the seizures. As each individual's response to the drug differs, the initial administration is carefully monitored and titrated. The type of medicine used depends on seizure type, and dosage may need to be adjusted from time to time. Some seizure types respond well to one medication and may respond poorly (or even be made worse) by others. Some medications need to be monitored for side effects and blood levels.

Epilepsy that does not respond to the use of several medications is called refractory epilepsy. Certain people with this type of epilepsy may benefit from brain surgery to remove the abnormal brain cells that are causing the seizures. Others may be helped with a vagal nerve stimulator, which is implanted in the chest. This stimulator can help reduce the number of seizures.

D. Macular Degeneration: In one embodiment, the present invention contemplates a method for treating macular degeneration using an impermeable therapeutic agent delivery device. In one embodiment, the delivery device provides controlled release of the agent. In one embodiment, the agent may be selected from the group comprising Macugen®, Avastin®, Lucentis®, or Kenalog®. In one embodiment, the device is implanted within the vitreous humor of the eye, such that the device is free-floating.

Macular degeneration is a disorder that affects the macula (the central part of the retina of the eye) causing decreased vision and possible loss of central vision. The macula is the part of the retina that allows the eye to see fine details at the center of the field of vision. Degeneration results from a partial breakdown of the retinal pigment epithelium (RPE). The RPE is the insulating layer between the retina and the choroid (the layer of blood vessels behind the retina). The RPE acts as a filter to determine what nutrients reach the retina from the choroid. Many components of blood are harmful to the retina and are kept away from the retina by normal RPE.

Breakdown of the RPE interferes with the metabolism of the retina, causing thinning of the retina (the "dry" phase of macular degeneration). These harmful elements may also cause new blood vessel to form and fluid to leak (the "wet" phase of macular degeneration).

Macular degeneration results in the loss of central vision only—peripheral fields usually stay normal. Although loss of ability to read and drive may be caused by macular degeneration, the disease does not lead to complete blindness. The disease becomes increasingly common as people age over 50. By age 75, almost 15% of people have this condition. Other risk factors are family history, cigarette smoking, and being Caucasian.

In general, macular degeneration symptoms usually include, but are not limited to, blurred, distorted, dim, or absent central vision. Testing to evaluate retinal function may include, but is not limited to, visual acuity, refraction test, pupillary reflex response, slit lamp examination, retinal examination, fluorescein angiography, Amsler grid, optical coherence tomography (OCT), a test that creates a color picture of the macula or retina While there is no specific treatment for dry macular degeneration, dietary zinc supplements may slow the progression of the disease. Alternatively, laser photocoagulation (i.e., for example, laser surgery to stop the leaking in choroidal blood vessels) may be useful in the early stages of the wet form of the disease. It involves the use of a thermal laser, which burns the abnormal, leaky blood vessels and stops them from spreading.

Photodynamic therapy may be used in conjunction with verteporfin (Visudyne®), a light-sensitive medication that is conventionally injected into a vein in the patient's arm. When a non-thermal laser is shone into the eyes, verteporfin produces a chemical reaction that destroys abnormal blood vessels. While the treatment is temporary, it can be repeated without adverse effect.

Other drugs used to treat the wet form of macular degeneration include, but is not limited to, Macugen, Avastin, Lucentis, and Kenalog. Conventional administration requires direct injection into the eye at regular intervals.

E. Pain Management: In one embodiment, the present invention contemplates a method for treating acute and/or chronic pain using an impermeable therapeutic agent delivery device. In one embodiment, the delivery device provides controlled release of the agent. In one embodiment, the agent comprises an opioid. In one embodiment, the device is implanted within a spinal disc, wherein the disc is suspected of having localized nerve cell damage. Pain is mediated by the peripheral and central nervous systems to identify to a biological organism the source and severity of an injury or illness. Pain may occur at many different intensities having many different qualitative natures. For example, a pain may be of a minimal intensity but having a stable nature. Alternatively, a pain may be of a maximal intensity but having an unstable nature (i.e., for example, throbbing). Further, the apparent location of a particular pain may not accurately reflect the actual source of the injury or illness (i.e., for example, referred pain).

Pain may occur in almost any part of the body including, but not limited to, abdomen, ankle, anus, back, bones, breast, ear, elbow, eye, finger, foot, groin, head, heel, hip, joints, knee, leg, muscles, neck, rib cage, shins, shoulder, flank, teeth, wrist, or somatoform. Pain medicines are also called analgesics. Every type of pain medicine has benefits and risks. Specific types of pain may respond better to one kind of medication than to another kind. Further, pain medications may also be patient-specific, where a specific pain medication may work in one patient but be ineffective in another. Over-the-counter (OTC) medications are good for many types of pain. OTC medicines include, but are not limited to, acetaminophen and nonsteroidal anti-inflammatory drugs. Acetaminophen is a non-aspirin pain reliever. It can be used to lower a fever and soothe headaches and other common aches and pains. However, acetaminophen does not reduce swelling (inflammation). This medicine is easier on the stomach than other pain medications, and it is safer for children. It can, however, be harmful to the liver if you take more than the recommended dose. NSAIDs include aspirin, naproxen, and ibuprofen. These medicines relieve pain, but they also reduce inflammation caused by injury, arthritis, or fever. NSAIDs work by reducing the production of hormone-like substances that cause pain.

Prescription medications may be needed for other types of pain. COX-2 inhibitors are a type of prescription painkiller that block an inflammation-promoting substance called COX-2. This class of drugs was initially believed to work as well as traditional NSAIDs, but with fewer stomach problems. However, numerous reports of heart attacks and stroke have prompted the FDA to re-evaluate the risks and benefits of the COX-2s. Patients should ask their doctor whether a COX-2 drug is appropriate and safe for them. Narcotic painkillers (i.e., for example, opioids) are very strong, potentially habit-forming medicines used to treat severe pain. They include, but are not limited to, morphine and codeine.

F. Parkinson's Disease: In one embodiment, the present invention contemplates a method for treating Parkinson's disease using an impermeable therapeutic agent delivery device. In one embodiment, the delivery device provides controlled release of the agent. In one embodiment, the agent comprises a dopamine agonist. In one embodiment, the device is implanted within a substantia nigra tissue, wherein the tissue is suspected of having localized cell damage. In one embodiment, the tissue comprises transplanted tissue. In one embodiment, the agent comprises a contrast agent, wherein the agent facilitates high resolution, localized brain imaging.

Parkinson's disease is a disorder of the brain that leads to shaking (tremors) and difficulty with walking, movement, and coordination. The disease affects approximately 2 of every 1,000 people and most often develops after age 50. It is one of the most common neurologic disorders of the elderly. Sometimes Parkinson's disease occurs in younger adults, but is rarely seen in children. It affects both men and women. In some cases, Parkinson's disease occurs within families, especially when it affects young people. Most of the cases that occur at an older age have no known cause.

Parkinson's disease occurs when the nerve cells in the part of the brain that controls muscle movement (i.e., for example, the substantia nigra) are gradually destroyed. The damage gets worse with time. The exact reason that the cells of the brain waste away is unknown. The disorder may affect one or both sides of the body, with varying degrees of loss of function.

Nerve cells within the substantia nigra comprise dopamine as a neurotransmitter. Damage in the area of the brain that controls muscle movement causes a decrease in dopamine production. Too little dopamine disturbs the balance between nerve-signaling substances (transmitters). Without dopamine, the nerve cells cannot properly send messages. This results in the loss of muscle function.

Some people with Parkinson's disease become severely depressed. This may be due to loss of dopamine in certain brain areas involved with pleasure and mood. Lack of dopamine can also affect motivation and the ability to make voluntary movements.

Early loss of mental capacities is uncommon However, persons with severe Parkinson's may have overall mental deterioration (including dementia and hallucinations). Dementia can also be a side effect of some of the medications used to treat the disorder.

Symptoms of Parkinson's disease may include, but be limited to, muscle rigidity, unstable, stooped, or slumped-over posture, loss of balance, abnormal gait, slow movements, voluntary movement initiation difficulty, walking initiation difficulty, standing initiation difficulty, myalgia, shaking, tremors, facial expression abnormalities, speech abnormalities, fine motor skill abnormalities, frequent falls, decline in intellectual function (may occur, can be severe), or gastrointestinal symptoms (i.e., for example, constipation).

Diagnosis usually requires a professional subjective evaluation of the expressed symptomology. Objective tests may be used to rule out other disorders that cause similar symptoms in order to perform a differential diagnosis.

Currently prescribed medications only control symptoms primarily by increasing the levels of dopamine in the brain, and do not provide any curative value. The specific type of medication, the dose, the amount of time between doses, or the combination of medications taken may need to be changed from time to time as symptoms change. Many medications can cause severe side effects, so monitoring and follow-up by the health care provider is important.

Types of medication usually prescribed for Parkinson's disease includes, but is not limited to, deprenyl, amantadine, levodopa, carbidopa, entacapone, pramipexole, ropinirole, rasagiline, or rotigotine. Additional medications to help reduce symptoms or control side effects of primary treatment medications include antihistamines, antidepressants, monoamine oxidase inhibitors (MAOIs), and others.

Transplantation of adrenal gland tissue to the brain has been attempted, with variable results. Such transplants are in an attempt to improve the bioavailability of naturally produced dopamine precursors that may help elevate dopamine levels.

G. Cancer: In one embodiment, the present invention contemplates a method for treating cancer using an impermeable therapeutic agent delivery device. In one embodiment, the delivery device provides controlled release of the agent. In one embodiment, the agent comprises an antiproliferative. In one embodiment, the device is implanted within a tumor or in proximity therewith. In one embodiment, the device is implanted within a cardiovascular vessel.

Cancer is generally defined as an uncontrolled growth of abnormal cells in the body. Cancerous cells may be either malignant or benign. Cancer grows out of normal cells in the body and appears to occur when the growth of cells in the body is out of control and cells divide too rapidly. It can also occur when cells lose the ability to undergo apoptosis.

There are many different kinds of cancers. Cancer can develop in almost any organ or tissue, including, but not limited to the lung, colon, breast, skin, bones, or nerve tissue. Specific types of cancer may include but are not limited to, lung cancer, brain cancer, cervical cancer, uterine cancer, liver cancer, leukemia, Hodgkin's lymphoma, Non-Hodgkin's lymphoma, kidney cancer, ovarian cancer, skin cancer, testicular cancer, thyroid cancer. There are multiple causes of cancers, including but not limited to, radiation, sunlight, tobacco, viruses, chemicals, poisonous mushrooms, or aflatoxins.

The three most common cancers in men in the United States are prostate cancer, lung cancer, and colon cancer. The three most frequently occurring cancers in women in the U.S. are breast, lung and colon cancers. Certain cancers are more common in particular geographic areas. For example, in Japan, there are many cases of gastric cancer, while in the U.S. this type of cancer is relatively rare. Differences in diet may play a role.

Symptoms of cancer depend on the type and location of the tumor. For example, lung cancer can cause coughing, shortness of breath, or chest pain, while colon cancer often causes diarrhea, constipation, and blood in the stool. Some cancers may not have any symptoms at all. In some cancers, such as gallbladder cancer, symptoms often are not present until the disease has reached an advanced stage. In general symptoms that are common with most cancers include, but are not limited to, fever, chills, night sweats, weight loss, loss of appetite, fatigue, or malaise.

Examination and tests to identify and/or diagnose cancers vary based on the type and location of the tumor. Nonetheless, common cancer tests include, but are not limited to, computer tomography scanning, complete blood count, blood chemistries, tissue biopsy, or X-ray radiography. Most cancer diagnoses are confirmed by biopsy. Depending on the location of the tumor, the biopsy may be a simple procedure or a serious operation. Most patients with cancer undergo imaging scans to determine the exact location of the tumor or tumors.

Cancer treatments also vary based on the type, stage and location of a particular cancer and/or cancerous tumor. The stage of a cancer refers to how much it has grown and whether the tumor has spread from its original location. If the cancer is confined to one location and has not spread, the goal for treatment would be surgery and cure. This is often the case with skin cancers. If the tumor has spread to local lymph nodes only, sometimes these can also be removed. If all of the cancer cannot be removed with surgery, the options for treatment include radiation, chemotherapy, or both. Some cancers require a combination of surgery, radiation, and chemotherapy.

H. Fungal Infections: In one embodiment, the present invention contemplates a method for treating a fungus infection using an impermeable therapeutic agent delivery device. In one embodiment, the delivery device provides controlled release of the agent. In one embodiment, the agent comprises an antifungal agent. In one embodiment, the device is implanted underneath a toenail. In one embodiment, the device is implanted underneath a fingernail. In one embodiment, the device is implanted using a twenty-seven (27) gauge needle.

The body normally hosts a variety of bacteria and fungi and some species are useful to the body, while others result in infection. Fungi can live on the dead tissues of the hair, nails, and outer skin layers. Fungal infections may include, but are not limited to, athlete's foot, jock itch, ringworm, or Tinea capitis. Other fungal infections may also include yeast-like fungi such as candida. Candida yeast infections include, but are not limited to, cutaneous candidiasis, diaper rash, oral thrush, or genital rashes.

In particular, fungal nail infections are most often seen in adults and are often quite persistant and refractory to most topical treatments. They often follow fungal infection of the feet. Toenails are affected more often than fingernails. People who frequent public swimming pools, gyms, or shower rooms—and people who perspire a great deal—commonly have mold-like infections. The fungi that cause them thrive in warm, moist areas.

Symptoms of a nail fungal infection include, but are not limited to, brittleness, change in nail shape, crumbling of the nail, debris trapped under the nail, discoloration, detachment, loss of luster and shine, or thickening.

Over-the-counter creams and ointments generally do not help treat this condition. Consequently, prescription antifungal medicines may taken by mouth may help clear the fungus in about 50% of patients. However, such medicines can cause side effects or may interfere with other medications. Further, some of the oral medications used to treat fungal infections of the nail can harm the liver.

EXAMPLE I

Manufacture of a Single Passageway Impermeable Delivery Device

This example describes the manufacture of one embodiment of an impermeable zero order kinetic drug delivery device having a single passageway.

Lengths of polyimide tubes were provided having a length of 20 mm and a diameter of 125 microns. At the centre of each tube, a passageway with a diameter of 30 microns was made using standard chemical procedures.

Seven (7) tubes having the optimal passageways were selected and loaded with a concentrated solution of crystal violet in ethanol by capillary method. The tubes were then allowed to stand for 24 hours at room temperature to evaporate alcohol from the tubes, such that the tube is tightly packed with a solid crystal violet composition.

After taking an initial weight measurement, an average amount of 126 micrograms of crystal violet was estimated inside the tubes. The ends of the tubes were sealed with a bioglue and dried.

EXAMPLE II

Release Kinetics of a Single Passageway Impermeable Delivery Device

This example describes one method that evaluates the release of an agent from a single passageway impermeable delivery device.

Single passageway tubes made according to Example I were placed in microvials containing 0.26 ml of phosphate buffered saline (0.01 M phosphate, pH 7.37). The vials were placed in a USP Disintegration Apparatus having dip rate of 30-32 dips per minute. The apparatus was connected to a waterbath maintained at 37° C. for the entire duration of study. The buffer was changed every 48 hours, sampled, and analyzed for the amount of crystal violet released using a UV-Vis Spectrophotometer for 28 days.

A significant linearity of release of the crystal violet was obtained from this single passageway device (see FIGS. 6 and 7). Additionally, the percentage release when extrapolated to 100% corresponds to the total duration of release of approximately 43 years.

EXAMPLE III

Manufacture of a Double Passageway Impermeable Delivery Device

This example describes the manufacture of one embodiment of an impermeable zero order kinetic drug delivery device having two passageways.

Several drug delivery devices were constructed in accordance with in Example I except that two passageways were made located equidistant from the tube centre. The optimal seven (7) were selected and loaded with crystal violet in accordance with Example I.

EXAMPLE IV

Release Kinetics of a Double Passageway Impermeable Delivery Device

This example describes one method that evaluates the release of an agent from a double passageway impermeable delivery device.

The double passageway tubes made in accordance with Example III were tested for crystal violet release in accordance with Example II. Again, significant linear agent release was obtained from the double passageway embodiment as seen in FIGS. 6 and 7. Additionally, the percentage release when extrapolated to 100% corresponds to the total duration of release of approximately 22 years.

EXAMPLE V

Manufacture of a Triple Passageway Impermeable Delivery Device

This example describes the manufacture of one embodiment of an impermeable zero order kinetic drug delivery device having three passageways.

Several drug delivery devices were constructed in accordance with Example I except that three passageways were made located equidistant from each end of the tube. The optimal seven (7) were selected and loaded with crystal violet in accordance with Example I.

EXAMPLE VI

Release Kinetics of a Triple Passageway Impermeable Delivery Device

This example describes one method that evaluates the release of an agent from a triple passageway impermeable delivery device.

The triple passageway tubes made in accordance with Example III were tested for crystal violet release in accordance with Example II. Again, significant linear agent release was obtained from the triple passageway embodiment (FIGS. 6 and 7). Additionally, the percentage release when extrapolated to 100% corresponds to the total duration of release of approximately 15 years.

EXAMPLE VII

Comparative Release Linearity Between Single, Double, and Triple Passageway Delivery Devices This example compares the linearity data collected in Example II, IV, and VI between the single, double, and triple passageway delivery devices.

The data shows no differences in the linearity of release rates amongst the single, double, and triple passageway devices. This data suggests that each passageway releases the same amount of agent over time regardless of the number of passageways present on the surface of the device. In this experiment, the passageways in each of the three groups have similar dimensions and only differ in number of holes on the surface (FIG. 8).

EXAMPLE VIII

Construction of a Single Outlet Port Impermeable Delivery Device

This example describes the manufacture of one embodiment of an impermeable zero order kinetic drug delivery device having a single outlet port at the end of the device.

Seven (7) lengths of polyimide tubes were provided having a length of 20 mm and a diameter of 125 microns. The tubes were then loaded with a concentrated solution of crystal violet in ethanol by capillary method. The tubes were then allowed to stand for 24 hours at room temperature to evaporate alcohol from the tubes, such that the tube is tightly packed with a solid crystal violet composition. One end of the tube was sealed with a bioglue while the other end was left open.

After taking an initial weight measurement, an average amount of 126 micrograms of crystal violet was estimated inside the tubes.

EXAMPLE IX

Release Kinetics of An Outlet Port Impermeable Delivery Device

This example describes one method that evaluates the release of an agent from a single outlet port impermeable delivery device.

A drug delivery device made in accordance with Example VIII was subjected to release studies as described in Example II. In particular, the device did not have any surface passageways but allowed to release from one open end. A significant linearity of release of the crystal violet was obtained over a period of five (5) days as shown in FIG. 9. The percentage release when extrapolated to 100% corresponds to the total duration of release of approximately 2 years.

EXAMPLE X

Release Kinetics of An Outlet Port Impermeable Delivery Device

Drug delivery devices were made having one outlet port and one sealed end. In particular, the device did not have any surface passageways but allowed to release from one open end. Three different variation of devices were prepared with different inside diameters, as in 200, 400, and 600 microns. Four devices of each type were subjected to release studies as described in Example I. Single passageway tubes were placed in micro vials containing 3.0 ml of phosphate buffered saline (0.01 M phosphate, pH 7.37). The vials were placed in an incubator maintained at 37° C. for the entire duration of study. The buffer was changed every 24 hours, sampled, and analyzed for the amount of crystal violet released using a UV-Vis Spectrophotometer for seven (7) days. A significant linearity of release of the crystal violet was obtained over a period of seven (7) days (FIG. 17).

EXAMPLE XI

Drug Loading of Prednisolone Suspension using Positive Pressure

An ethanolic suspension of prednisolone was prepared by adding 200 mg of prednisolone to 0.5 ml ethanol. A 1 ml syringe, which was attached to the touhy borst adapter, was filled with the high density suspension. The polyimide tube (diameter=125 microns) was screwed tightly to the other end of the adapter, and the prednisolone suspension was injected into the tube. Afterwards, the ethanol was evaporated by allowing the tubes to stand overnight. The final weight was analyzed using TGA-7. A net amount of 87.58±11.70 micrograms of prednisolone was loaded into the tubes. The amount of drug loaded per unit length of the tube was 5.68±0.65 micrograms/mm. The net amount of drug loaded indicates content uniformity amongst all the tubes whereas, amount of drug loaded per unit length indicates the homogeneity of drug distribution inside the tube.

EXAMPLE XII

Drug Loading of Powdered Crystal Violet

A group of polyimide tubes (diameter=1000 microns) were manually loaded with crystal violet powder. The average amount of crystal violet loaded per unit length in the groups was 5.31±0.28 milligrams/cm.

Although the present invention has been described with several embodiments, a myriad of changes, variations, alterations, transformations, and modifications may be suggested to one skilled in the art, and it is intended that the present disclosure encompass such changes, variations, alterations, transformation, and modifications as they fall within the scope of the appended claims.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for making a device for delivery of one or more active agents with zero-order kinetics comprising the steps of:
providing a mold of a non-planer enclosure comprising a first surface and a second surface, wherein the first surface comprises one or more trenches, cavities or depressions, wherein each of the one or more trenches, cavities or depressions comprise one or more holes or perforations;
placing a first substrate in the trenches, cavities or depressions, wherein the substrate may optionally be held in place in the trench by using an adhesive; and
transferring a shape of the holes or the perforations in the one or more trenches, cavities or depressions to the first substrate by one or more microfabrication techniques to make a non-planer enclosure having a series of passageways that connect an outer surface and an inner area for the delivery of the one or more active agents through the series of passageways with a zero order release kinetics.

2. The method of claim 1, wherein the shape of the one or more holes or perforations is selected from the group consisting of a triangle, a polygon, an undecagon, a trapezium or trapezoid, a quadrilateral, an icosagon, a star polygon, an annulus, a circle, a crescent, an ellipse, an oval, an arbelos, a Reuleaux triangle, a semicircle, a sphere, an Archimedean spiral, an astroid, a deltoid, a super ellipse, and a tomahawk.

3. The method of claim 1, wherein the one or more microfabrication techniques are selected from the group consisting of physical etching, chemical etching, reactive ion etching, physical vapor deposition, chemical vapor deposition, liftoff, electroplating, electroless plating, ion milling, laser ablation, plasma torch cutting, lithography, and combinations and modifications thereof.

4. The method of claim 1, further comprising the optional step of pushing the substrate to the bottom of the trench by using a second substrate, wherein the second substrate is selected from the group consisting of silicon, glass, polymer, stainless steel, metals, alloys, ceramics, semiconductors, dielectrics, and combinations and modifications thereof.

5. The method of claim 1, further comprising the optional step of flipping the mold prior to the step of transferring the shape, wherein the flipping results in the second surface facing the one or more microfabrication or etching sources, wherein the etching sources are selected from the group consisting of ions, etching gases, plasma, laser beams, and combinations or modifications thereof.

6. The method of claim 1, wherein the first substrate material is selected from the group consisting of a polymer, a rubber, a metal, a semiconductor, a dielectric, a mineral, a ceramic, and a glass.

7. The method of claim 1, wherein the method further comprising the step of loading an active agent supply in the device by a method selected from the group consisting of capillary action, dipping, injection, and pressure loading using positive or negative pressures.

8. The method of claim 1, wherein the one or more active agents comprise a solid, a liquid dosage, a semi-solid, a powder or a hydrogel.

9. The method of claim 1, wherein the device may optionally be attached to a medical device or a microelectronic circuit, wherein the microelectronic circuit comprises at least one of a sensor, a transmitter, a receiver, a transceiver, a switch, a power supply or a light.

10. The method of claim 9, wherein the medical device is selected from the group consisting of a stent, an urinary catheter, an intravascular catheter, a dialysis shunt, a wound drain tube, a skin suture, a vascular graft, an implantable mesh, an intraocular device, an eye buckle, a heart valve, and combinations and modifications thereof.

11. The method of claim 1, wherein the one or more holes or perforations are circular.

12. The method of claim 11, wherein the circular holes or the perforations range from 1 nanometer-1 centimeter, 100 nanometers-100 microns, 1 micron-50 microns, 10-30 microns, 15-25 microns or 20 microns.

13. The method of claim 1, wherein the first substrate is a polymer tube and the technique is reactive ion etching using a plasma.

14. The method of claim 1, further comprising the optional step of polymer coating the device thereby preventing a release of the one or more active agents until the coating is removed, which then causes release of the one or more active agents at a substantially constant rate.

15. The method of claim 14, wherein the polymer coating is poly(methacrylates), and one or more active agents are selected from the group consisting of drugs, proteins, vitamins, minerals, saccharides, lipids, nucleic acid, peptides, manure, plant nutrients, chemicals, perfumes, fragrances, flavoring agents, animal feed, effervescent gas releasing agents, and combinations and modifications thereof.

16. The method of claim 14, wherein the drugs are selected from the group consisting of an analgesic agent, an antiinflammatory agent, an antihistaminic agent, an antiallergic agent, a central nervous system drug, an antipyretic agent, a respiratory agent, a steroid, a local anesthetic, a sympathomimetic agent, an antihypertensive agent, an antipsychotic agent, a calcium antagonist, a muscle relaxant, a vitamin, a cholinergic agonist, an antidepressant, an antispasmodic agent, a mydriatic agent, an anti-diabetic agent, an anorectic agent, an antiulcerative agent, an anti-tumor agent, or combinations modifications thereof and the proteins are selected from the group consisting of an immunoglobulin or fragments thereof, a hormone, an enzyme, a cytokine, a biomolecule, and combinations and modifications thereof.

17. A method for making a device for delivery of one or more active agents with zero-order kinetics by a reactive ion etching technique comprising the steps of:

provanding a silicon-wafer mold comprising a first surface and a second surface, wherein the first surface comprises one or more trenches, cavities or depressions, wherein each of the one or more trenches, cavities or depressions comprise one or more holes, perforations or patterns wherein the silicon-wafer mold forms a non-planer cylindrical enclosure;

placing a first substrate in the trenches, cavities or depressions, wherein the substrate may optionally be held in place in the trench by using an adhesive, wherein the first substrate comprises a polyimide polymer; and transferring a shape of the holes, the perforations or the patterns in the one or more trenches, cavities or depressions to the first substrate by using a reactive plasma to make a non-planer enclosure having a series of passageways that connect an outer surface and an inner area for the delivery of the one or more active agents through the series of passageways with a zero order release kinetics.

18. The method of claim 17, further comprising the optional step of pushing the first substrate to the bottom of the trenches, cavities or depressions by using a second substrate, wherein the second substrate is selected from the group consisting of silicon, glass, polymer, stainless steel, metals, alloys, ceramics, semiconductors, dielectrics, and combinations and modifications thereof.

19. The method of claim 17, further comprising the optional step of flipping the mold prior to the step of transferring the shape, wherein the flipping results in the second surface facing the reactive plasma.

* * * * *